(12) United States Patent
Aslanian et al.

(10) Patent No.: US 7,408,066 B2
(45) Date of Patent: Aug. 5, 2008

(54) CARBON-LINKED SUBSTITUTED PIPERIDINES AND DERIVATIVES THEREOF USEFUL AS HISTAMINE $H_3$ ANTAGONISTS

(75) Inventors: Robert G. Aslanian, Rockaway, NJ (US); Michael Y. Berlin, Flemington, NJ (US); Ying Huang, Berkeley Heights, NJ (US); Kevin D. McCormick, Basking Ridge, NJ (US); Mwangi W. Mutahi, Nyeri (KE); Neng-Yang Shih, Warren, NJ (US); Pauline C. Ting, New Providence, NJ (US); Wing C. Tom, Cedar Grove, NJ (US); Junying Zheng, Bridgewater, NJ (US)

(73) Assignee: Schering Corproation, Kenilworth, NJ (US)

( * ) Notice: Subject to any disclaimer, the term of this patent is extended or adjusted under 35 U.S.C. 154(b) by 0 days.

(21) Appl. No.: 11/455,873

(22) Filed: Jun. 19, 2006

(65) Prior Publication Data

US 2007/0010513 A1 Jan. 11, 2007

Related U.S. Application Data

(60) Provisional application No. 60/692,175, filed on Jun. 20, 2005.

(51) Int. Cl.
*C07D 401/04* (2006.01)
*C07D 401/14* (2006.01)
*A61K 31/495* (2006.01)

(52) U.S. Cl. .................. 546/184; 546/192; 546/193; 546/194; 544/224; 544/336

(58) Field of Classification Search .......... 546/184, 546/192, 193, 194; 544/224, 336
See application file for complete search history.

(56) References Cited

U.S. PATENT DOCUMENTS

| | | | |
|---|---|---|---|
| 5,869,479 A | 2/1999 | Kreutner et al. | |
| 6,720,328 B2 * | 4/2004 | Aslanian et al. | 514/275 |
| 6,849,621 B2 * | 2/2005 | Rosenblum et al. | 514/217.04 |
| 6,951,871 B2 * | 10/2005 | Aslanian et al. | 514/316 |
| 7,105,505 B2 * | 9/2006 | Zeng et al. | 514/210.21 |
| 7,220,735 B2 * | 5/2007 | Ting et al. | 514/210.21 |
| 2004/0019099 A1 | 1/2004 | Aslanian et al. | |
| 2004/0048843 A1 | 3/2004 | Ting et al. | |
| 2004/0097483 A1 | 5/2004 | Zeng et al. | |
| 2004/0198743 A1 | 10/2004 | Hey et al. | |
| 2004/0224953 A1 | 11/2004 | Cowart et al. | |

FOREIGN PATENT DOCUMENTS

| | | | |
|---|---|---|---|
| WO | WO 01/58891 A2 | 8/2001 | |
| WO | WO 0158891 * | 8/2001 | |
| WO | WO 02/32693 A2 | 4/2002 | |
| WO | WO 02/072570 A | 9/2002 | |
| WO | WO 03/088967 A1 | 10/2003 | |
| WO | WO 03/103669 A1 | 12/2003 | |
| WO | WO 04/000831 A1 | 12/2003 | |
| WO | WO 2004/089373 A1 | 10/2004 | |
| WO | WO 2004/101546 A1 | 11/2004 | |

OTHER PUBLICATIONS

Tashiro, Manabu, et al., "Roles of histamine in regulation of arousal and cognition: functional neuroimaging of histamine H1 receptors in human brain", Life Sciences 72:409-414 (2002).
Leurs, Rob, et al., "The Histamine H3 Receptor: From Gene Cloning to H3 Receptor Drugs", Nature Reviews, Drug Discovery 4:107-120, (2005).
Hancock, Arthur A. and Fox, Gerard B., "Cognitive enhancing effects of drugs that target histamine receptors", Cognitive Enhancing Drugs, (ed. J. J. Buccafusco), 97-114 (2004).
PCT International Search Report dated Sep. 28, 2006 for corresponding PCT Application No. PCT/US2006/023937.

* cited by examiner

*Primary Examiner*—D. Margaret Seaman
*Assistant Examiner*—Nizal S Chandrakumar
(74) *Attorney, Agent, or Firm*—Jeffrey P. Bergman; Mark W. Russell

(57) ABSTRACT

Disclosed are compounds of the formula

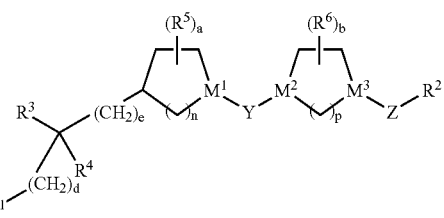

or a pharmaceutically acceptable salt thereof, wherein:
$M^1$ and $M^3$ are CH or N;
$M^2$ is CH, CF or N;
Y is $-C(=O)-$, $-C(=S)-$, $-(CH_2)_q-$, $-C(=NOR^7)-$ or $-SO_{1-2}-$;
Z is a bond or optionally substituted alkylene or alkenylene;
$R^1$ is H, alkyl, alkenyl, or optionally substituted cycloalkyl, aryl, heteroaryl, heterocycloalkyl or a group of the formula:

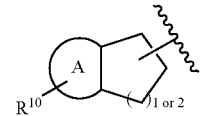

where ring A is a monoheteroaryl ring;
$R^2$ is optionally substituted alkyl, alkenyl, aryl, heteroaryl, cycloalkyl or heterocycloalkyl;
and the remaining variables are as defined in the specification; compositions and methods of treating allergy-induced airway responses, congestion, obesity, metabolic syndrome nonalcoholic fatty liver disease, hepatic steatosis, nonalcoholic steatohepatitis, cirrhosis, hepatacellular carcinoma or cognition deficit disorders using said compounds, alone or in combination with other agents.

9 Claims, No Drawings

CARBON-LINKED SUBSTITUTED PIPERIDINES AND DERIVATIVES THEREOF USEFUL AS HISTAMINE H₃ ANTAGONISTS

RELATED APPLICATIONS

This application claims priority to provisional application U.S. Ser. No. 60/692,175, filed Jun. 20, 2005, herein incorporated by reference.

FIELD OF THE INVENTION

The present invention relates to carbon-linked substituted piperidines and derivatives thereof useful as histamine $H_3$ antagonists. The invention also relates to pharmaceutical compositions comprising said compounds and their use in treating inflammatory diseases, allergic conditions, obesity, metabolic syndrome, cognition deficit disorders, cardiovascular and central nervous system disorders. The invention also relates to the use of a combination of histamine $H_3$ antagonists of this invention with histamine $H_1$ compounds for the treatment of inflammatory diseases and allergic conditions, as well to the use of a combination of an histamine $H_3$ antagonist of this invention with other actives useful for treating obesity, metabolic syndrome or cognition deficit disorders. Pharmaceutical compositions comprising a combination of one or more novel histamine $H_3$ antagonist compounds of the invention with one or more histamine $H_1$ compounds or one or more compounds useful for treating obesity, metabolic syndrome or cognition deficit disorders are also contemplated.

BACKGROUND OF THE INVENTION

The histamine receptors, $H_1$, $H_2$, $H_3$ and $H_4$ have been characterized by their pharmacological behavior. The $H_1$ receptors are those that mediate the response antagonized by conventional antihistamines. $H_1$ receptors are present, for example, in the ileum, the skin, and the bronchial smooth muscle of humans and other mammals. The most prominent $H_2$ receptor-mediated responses are the secretion of gastric acid in mammals and the chronotropic effect in isolated mammalian atria. $H_4$ receptors are expressed primarily on eosinophils and mast cells and have been shown to be involved in the chemotaxis of both cell types.

In the periphery, $H_3$ receptor sites are found on sympathetic nerves, where they modulate sympathetic neurotransmission and attenuate a variety of end organ responses under control of the sympathetic nervous system. Specifically, $H_3$ receptor activation by histamine attenuates norepinephrine outflow to resistance and capacitance vessels, causing vasodilation. In addition, in rodents, peripheral $H_3$ receptors are expressed in brown adipose tissue, suggesting that they may be involved in thermogenesis regulation.

$H_3$ receptors are also present in the CNS. $H_3$ receptor expression is observed in cerebral cortex, hippocampal formation, hypothalamus and other parts of the human and animal brain. $H_3$ receptors are expressed on histaminergic neurons and, as heteroreceptors, on neurons involved in other neurotransmitter systems, where $H_3$ receptor activation results in presynaptic inhibition of neurotransmitter release. In the particular case of histaminergic neurons, $H_3$ receptors have been implicated in the regulation of histamine hypothalamic tone, which in turn has been associated with the modulation of sleeping, feeding and cognitive processes in the human brain (see, for example, Leurs et al., Nature Reviews, Drug Discovery, 4, (2005), 107).

It is also known and has been described in the literature that histamine is involved in regulation of cognitive and memory processes in the human brain (see, for example, Life Sciences, 72, (2002), 409-414). Consequently, indirect modulation of histaminergic brain function through the central $H_3$ receptors may be a means to modulate these processes. Different classes of $H_3$ receptor ligands have been described and their use for neurological and psychiatric diseases has been suggested (see, e.g., US 20040224953, WO2004089373, WO2004101546). $H_3$ receptor antagonists may be useful in treating various neuropsychiatric conditions, where cognitive deficits are an integral part of the disease, specifically ADHD, schizophrenia and Alzheimer's disease (see, for example, Hancock, A.; Fox, G. in Drug Therapy (ed. Buccafusco, J. J.). (Birkhauser, Basel, 2003).

Imidazole $H_3$ receptor antagonists are well known in the art. More recently, non-imidazole $H_3$ receptor antagonists have been disclosed in U.S. Pat. Nos. 6,720,328 and 6,849,621 and in and 2004/0019099. WO 2003/103669 and WO 2003/088967 (US Published Applications 2004/0097483 and 2004/0048843) disclose 1-(4-piperidinyl)-benzimidazolone and 1-(4-piperidinyl)benzimidazole derivatives; these compounds are excluded from this application. All these patents or publications are incorporated by reference.

U.S. Pat. No. 5,869,479 discloses compositions for the treatment of the symptoms of allergic rhinitis using a combination of at least one histamine $H_1$ receptor antagonist and at least one histamine $H_3$ receptor antagonist.

SUMMARY OF THE INVENTION

The present invention provides novel compounds of formula I:

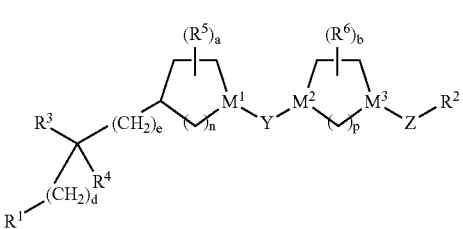

or a pharmaceutically acceptable salt thereof, wherein:

a is 0, 1 or 2;

b is 0, 1 or 2;

d is 0 or 1;

e is 0 or 1 n is 1, 2 or 3;

p is 1, 2 or 3;

$M^1$ is CH or N;

$M^2$ is CH, CF or N;

$M^3$ is CH or N with the proviso that when $M^2$ and $M^3$ are each N, p is 2 or 3;

Y is —C(=O)—, —C(=S)—, —(CH$_2$)$_q$—, —C(=NOR$^7$)— or —SO$_{1-2}$—;

q is 1 to 5, provided that when $M^1$ and $M^2$ are both N, q is 2 to 5;

Z is a bond, —[C(R$^8$)(R$^{8'}$)]$_n$·, —CH(R$^{20}$)—CH(R$^{20}$)—O—, —CH(R$^{20}$)—CH(R$^{20}$)—N—, —CH(R$^{20}$)—[C(R$^{21}$)

$(R^{21'})_{1-5}$—, —$CH(R^{20})$—$C(R^{20})$=$C(R^{20})$—, —$CH(R^{20})$—$C(R^{20})$=$C(R^{20})$—$[C(R^{21})(R^{21'})]_{1-3}$— or —$[C(R^8)(R^{8'})]_{n'}$ wherein at least one $C(R^8)(R^{8'})$ is interrupted by a cycloalkylene or heterocycloalkylene group, provided that when $M^3$ is N and Z is $R^8$-alkylene interrupted by a heterocycloalkylene group bonded through a ring nitrogen, the alkylene portion of the Z group has 2-4 carbon atoms between $M^3$ and said nitrogen;

n' is an integer from 1 to 6

$R^1$ is H, alkyl, alkenyl, $R^{10}$-cycloalkyl, $R^{10}$-aryl, $R^{10}$-monoheteroaryl, preferably $R^{10}$-pyridyl or $R^{10}$-quinolyl, $R^{10}$-heterocycloalkyl, or a group of the formula:

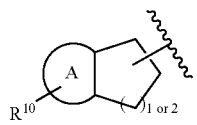

where ring A is a monoheteroaryl ring, said monoheteroaryl or monoheteroaryl ring is a moncyclic ring having 1 to 4 heteroatoms selected from O, S, and N, said heteroatoms interrupting an aromatic carbocyclic ring structure having from 1 to 6 carbon atoms, provided that there are no adjacent oxygen and/or sulfur atoms present, with monoheteroaryl rings such as isothiazole, isoxazole, oxazole, triazole, tetrazole, thiazole, thiophene, furane, pyrrole, pyrazole, pyrane, pyrimidine, pyrazine, furazanyl, pyridazine and pyridine (including pyridine N-oxide) being preferred;

and $R^3$ and $R^4$ are independently selected from the group consisting of H, halo, alkyl, haloalkyl, hydroxyalkyl, alkoxyalkyl, hydroxyalkoxy, alkoxyalkoxy, aryl, arylalkyl, cycloalkyl, heterocycloalkyl, heteroaryl, heteroarylalkyl, —$OR^{12}$, —CN, —$(CH_2)_f$—$N(R^{12})_2$, —$(CH_2)_f$—$N(R^{19})$—$SO_2R^{12}$, —$(CH_2)_f$—$N(R^{19})$—$C(O)R^{12}$, —$(CH_2)_f$—NHC(O)NHR$^{12}$, —$(CH_2)_f$—NHC(O)OR$^{12}$, —O—C(O)NHR$^{12}$, —$(CH^2)_f$—C(O)OR$^{12}$ and —O—$(CH_2)_f$—C(O)OR$^{12}$, provided that when one of $R^3$ and $R^4$ is a heteroatom-linked substituent, the other is H;

f is 0, 1 or 2;

or $R^3$ and $R^4$, together with the carbon to which they are attached, form —C(=C(R^{15})(R^{18}))—, a 3-7 membered cycloalkyl ring substituted by $R^{13}$, a 3-7-membered heterocycloalkyl ring substituted by $R^{13}$, a $R^{13}$-phenyl ring, or a 5-6-membered heteroaryl ring substituted by $R^{13}$; or when d is 1, or e is 1, or both d and e are 1, $R^3$ and $R^4$, together with the carbon to which they are attached, form —C(O)—;

or $R^1$—$(CH_2)_d$—$C(R^3)(R^4)$—$(CH_2)_e$— forms

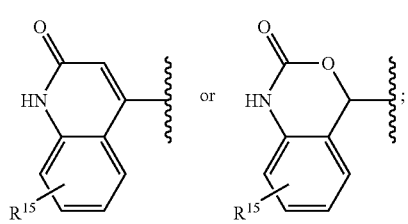

$R^2$ is $R^{16}$-alkyl, $R^{16}$-alkenyl, $R^{16}$-aryl, $R^{16}$-heteroaryl, $R^{16}$-cycloalkyl or $R^{16}$-heterocycloalkyl;

$R^5$ and $R^6$ are each independently selected from the group consisting of halo, alkyl, —OH, alkoxy, haloalkyl, preferably —$CF_3$ and —CN; or two $R^5$ substituents on the same carbon atom form =O;

$R^7$ is H, alkyl, haloalkyl, $R^{10}$-aryl or $R^{10}$-heteroaryl;

$R^8$ and $R^{8'}$ independently are 1, 2 or 3 substituents independently selected from the group consisting of H, $R^{10}$-cycloalkyl, $R^{10}$-heterocycloalkyl, $R^{10}$-aryl, $R^{10}$-heteroaryl and haloalkyl, preferably —$CF_3$;

each $R^9$ is independently selected from the group consisting of H and alkyl;

$R^{10}$ is 1 to 4 substituents independently selected from the group consisting of H, halo, alkyl, —OH, alkoxy, $R^{10'}$-cycloalkyl, $R^{10'}$-aryl, $R^{10'}$-heteroaryl, $R^{10'}$-aryloxy, haloalkyl, preferably —$CF_3$, —$CHF_2$, —, haloalkoxy, preferably $OCF_3$, —$NO_2$, —$CO_2R^{11}$, —$N(R^{11})_2$, —$CON(R^{11})_2$, —$NHC(O)R^{11}$, —$NHC(O)OR^{11}$, —$NHSO_2R^{11}$, —$SO_2N(R^{11})_2$ and —CN;

each $R^{10'}$ is 1 to 4 substituents independently selected from the group consisting of H, halo, alkyl, —OH, alkoxy, aryl, heteroaryl, aryloxy, haloalkyl, preferably —$CF_3$, or —$CHF_2$, —, haloalkoxy, preferably $OCF_3$, —$NO_2$, —$CO_2R^{11}$, —$N(R^{11})_2$, —$CON(R^{11})_2$, —$NHC(O)R^{11}$, —$NHC(O)OR^{11}$, —$NHSO_2R^{11}$, —$SO_2N(R^{11})_2$ and —CN;

each $R^{11}$ is independently selected from the group consisting of H, alkyl, haloalkyl, $R^{18}$-aryl, $R^{18}$-heteroaryl, $R^{18}$-arylalkyl, $R^{18}$-cycloalkyl and $R^{18}$-heterocycloalkyl;

each $R^{12}$ is independently selected from the group consisting of H, alkyl, alkenyl, haloalkyl, $R^{18}$-aryl, $R^{18}$-arylalkyl, $R^{18}$-heteroaryl, $R^{18}$-heteroarylalkyl, $R^{18}$-cycloalkyl, $R^{18}$-cycloalkylalkyl and $R^{18}$-heterocycloalkyl;

$R^{13}$ is 1 to 4 substituents independently selected form the group consisting of H, halo, alkyl, —OH, alkoxy, hydroxyalkyl, alkoxyalkyl, —$CO_2R^{14}$, —$C(O)N(R^{14})_2$, haloalkyl, preferably —$CF_3$, and —CN; or two $R^{13}$ substituents on the same carbon atom form =O;

each $R^{14}$ is independently selected from the group consisting of H and alkyl;

$R^{15}$ is H, alkyl, halo, aryl or haloalkyl, preferably —$CF_3$;

$R^{16}$ is 1 to 3 substituents independently selected from the group consisting of H, halo, alkyl, —OH, alkoxy, $R^{10}$-aryl, $R^{10}$-aryloxy, haloalkyl, preferably —$CF_3$, haloalkoxy, preferably —$OCF_3$, —$NO_2$, —$CO_2R^{17}$, —$N(R^{17})_2$, —$CON(R^{17})_2$, —$NHC(O)R^{17}$, —$NHC(O)OR^{17}$, —$NHSO_2R^{17}$, —$SO_2N(R^{17})_2$ and —CN;

each $R^{17}$ is independently selected from the group consisting of H, alkyl, haloalkyl, $R^{10}$-aryl, $R^{10}$-heteroaryl, $R^{10}$-cycloalkyl and $R^{10}$-heterocycloalkyl;

$R^{18}$ is H, alkyl, halo, aryl, haloalkyl, preferably —$CF_3$, alkoxy, heteroaryl, —O—$C(O)R^{12}$, —$C(O)N(R^{12})_2$, —$C(O)OR^{12}$, —$NO_2$, —CN or —C(O)-heterocycloalkyl;

$R^{19}$ is H, alkyl or $R^{10}$-heterocycloalkylalkyl, preferably $R^{10}$-pyridylmethyl, with pyridylmethyl being most preferred;

$R^{20}$ is independently selected from the group consisting of H and alkyl; and $R^{21}$ independently is 1, 2 or 3 substituents independently selected from the group consisting of H, $R^{10}$-cycloalkyl, $R^{10}$-heterocycloalkyl, $R^{10}$-aryl, $R^{10}$-heteroaryl, haloalkyl, preferably —$CF_3$, halo, —CN, —OH, alkoxy, haloalkoxy, preferably —$OCF_3$, —$NO_2$, and —$N(R^9)_2$; and $R^{21'}$ is independently are 1, 2 or 3 substituents independently selected from the group consisting of H, $R^{10}$-cycloalkyl, $R^{10}$-heterocycloalkyl, $R^{10}$-aryl, $R^{10}$-heteroaryl, haloalkyl, preferably —$CF_3$—OH, alkoxy, haloalkoxy, preferably —$OCF_3$, —$NO_2$, and —$N(R^9)_2$.

This invention also provides a pharmaceutical composition comprising an effective amount of at least one compound of formula I and a pharmaceutically acceptable carrier.

This invention further provides a method of treating: allergy, allergy-induced airway (e.g., upper airway) responses (e.g., pruritis, sneezing, rhinorrhea, mucosal inflammation; see, for example, McLeod, *JPET*, 305 (2003) 1037), congestion (e.g., nasal congestion), hypotension, cardiovascular disease, diseases of the GI tract, hyper- and hypomotility and acidic secretion of the gastro-intestinal tract, metabolic syndrome, obesity, sleeping disorders (e.g., hypersomnia, somnolence, and narcolepsy), hypo- and hyperactivity of the central nervous system (for example, agitation and depression), cognition deficit disorders (such as attention deficit hyperactivity disorder (ADHD), Alzheimer's Disease (AD) and schizophrenia), nonalcoholic fatty liver disease (NAFLD), hepatic steatosis, nonalcoholic steatohepatitis (NASH), cirrhosis, hepatacellular carcinoma and/or other CNS disorders (such as migraine), comprising administering to a patient in need of such treatment an effective amount of at least one compound of formula I. "Patient" means a mammal, typically a human, although veterinary use is also contemplated.

In particular, compounds of this invention are particularly useful for treating congestion, metabolic syndrome, obesity, and cognition deficit disorders.

This invention further provides a pharmaceutical composition comprising an effective amount of a combination of at least one compound of formula I and at least one $H_1$ receptor antagonist in combination with a pharmaceutically acceptable carrier.

This invention further provides a method of treating allergy, allergy-induced airway responses, and/or congestion comprising administering to a patient in need of such treatment an effective amount of a combination of at least one compound of formula I and at least one $H_1$ receptor antagonist.

This invention further provides a pharmaceutical composition comprising an effective amount of a combination of at least one compound of formula I and at least one other compound useful in treating obesity, metabolic syndrome, cognition deficit disorders, NAFLD, hepatic steatosis, NASH, cirrhosis, or hepatacellular carcinoma in combination with a pharmaceutically acceptable carrier.

This invention further provides a method of treating obesity, metabolic syndrome or cognition deficit disorders comprising administering to a patient in need of such treatment an effective amount of a combination of at least one compound of formula I and at least one other compound useful in treating obesity, metabolic syndrome, cognition deficit disorders, NAFLD, hepatic steatosis, NASH, cirrhosis, or hepatacellular carcinoma.

Kits comprising a compound of formula I in a pharmaceutical composition, and a separate $H_1$ receptor antagonist in a pharmaceutical composition in a single package are also contemplated, as are kits comprising a compound of formula I in a pharmaceutical composition, and a separate compound useful in treating obesity, metabolic syndrome cognition deficit disorders, NAFLD, hepatic steatosis, NASH, cirrhosis, or hepatacellular carcinoma in a pharmaceutical composition in a single package.

DETAILED DESCRIPTION OF THE INVENTION

Preferred definitions of the variables in the structure of formula I are as follows: $R^1$ is preferably $R^{10}$-aryl or $R^{10}$-heteroaryl. More preferably, $R^1$ is $R^{10}$-phenyl or $R^{10}$-heteroaryl wherein heteroaryl is a 6-membered ring, especially $R^{10}$-pyridyl. $R^{10}$ is preferably 1 or 2 substituents independently selected from H, alkyl, halo, —$CF_3$, —$CHF_2$ and —CN.

Variables d and e are preferably each 0.

$M^1$ is preferably N. $M^2$ is preferably CH or CF, more preferably CF. $M^3$ is preferably N.

Variables n and p are preferably each 2.

Variables a and b are preferably each independently 0 or 1, more preferably 0.

Y is preferably —C(=O)—.

Z is preferably $C_1$-$C_3$ alkylene, —CH($R^{20}$)—[C($R^{21}$)($R^{23}$)]$_{1-5}$—, —CH($R^{20}$)—C($R^{20}$)=C($R^{20}$)—, —($CH_2$)$_2$—O— or $C_1$-$C_3$ alkylene interrupted by a cycloalkylene group, wherein $R^{20}$ is preferably H and $R^{21}$ is halo. More preferably, Z is one of the following: —$CH_2$—, —($CH_2$)$_3$—, —$CH_2$—CH=CH—, —($CH_2$)$_2$—CH(F)—, —$CH_2$—CH(F)—$CH_2$—, —($CH_2$)$_2$—O— or

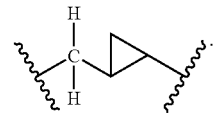

$R^2$ is preferably $R^{16}$-heteroaryl, more preferably a 5 or 6 membered $R^{16}$-heteroaryl, especially $R^{16}$-pyridyl, $R^{16}$-pyrimidyl, $R^{16}$-pyradazinyl or $R^{16}$-thiazolyl. Also preferred are compounds wherein $R^2$ is $R^{16}$-heterocycloalkyl, with $R^{16}$-azetidinyl or $R^{16}$-tetrahydropyranyl being more preferred. $R^{16}$ is preferably 1 or 2 substituents independently selected from H, —$CH_3$, —$NH_2$ and —$NHCH_3$. Most preferred is 2-amino pyridine.

When $R^3$ and $R^4$ are not joined together, preferably, $R^3$ is hydrogen and $R^4$ is hydrogen, halo, —OH, alkoxyalkyl or —($CH_2$)$_f$—N($R^{19}$)$SO_2R^{12}$, wherein $R^{19}$ is H and f is 0; more preferably $R^3$ is H and $R^4$ is alkoxyalkyl.

When $R^3$ and $R^4$ are joined together with the carbon to which they are attached, they preferably form —C(=C($R^{15}$)($R^{18}$)—, wherein $R^{15}$ and $R^{18}$ are each H, or wherein $R^{15}$ is H and $R^{18}$ is halo or alkoxy, more preferably methoxy or fluoro. Also preferred are compounds wherein $R^3$, $R^4$ and the carbon to which they are attached form an $R^{13}$-substituted cycloalkyl ring, preferably $R^{13}$-cyclopropyl.

$R^5$ and $R^6$ are independently preferably selected from H, alkyl, OH or fluoro.

Preferred compounds among those exemplified below are examples 1, 2, 3, 5, 8, 9, 10, 12, 13, 14, 17, 26, 27, 28, 30, 33, 34, 35, 41, 58, 60, 63, 66, 68, 77, 81, 86, 87, 90, 91, 94, 95, 96, 97, 99, 100, 101, and 108.

More preferred are compounds of examples 1, 2, 5, 8, 9, 10, 13, 14, 27, 28, 30, 34, 35, 60, 66, 77, 81, 86, 87 and 91.

As used herein, the following terms have the following meanings, unless indicated otherwise:

the left side of all divalent radicals is attached to the left portion of formula I and the right side of all divalent radicals is attached the the right side of formula I based upon where the variable is in formula I; e.g; when Z is —CH($R^{20}$)—C($R^{20}$)=C($R^{20}$)—, the "—CH($R^{20}$)" portion of the variable is attached to $M^3$ and the "C($R^{20}$)=C($R^{20}$)—" portion is attached to $R^2$.

alkyl (including, for example, the alkyl portions of arylalkyl and alkoxy) represents straight and branched carbon chains and contains from one to six carbon atoms;

alkylene represents a divalent straight or branched alkyl chain, e.g., ethylene (—$CH_2$—) or propylene (—$CH_2CH_2CH_2$—);

alkenyl represents a straight or branched $C_1$ to $C_6$ carbon chain comprising one or two carbon-carbon double bonds;

alkenylene represents a divalent alkenyl group;

haloalkyl or haloalkoxy represent alkyl or alkoxy chains as defined above wherein one or more hydrogen atoms are replaced by halogen atoms, e.g., —CF$_3$, CF$_3$CH$_2$CH$_2$—, CF$_3$CF$_2$— or CF$_3$O—;

aryl (including the aryl portion of arylalkyl) represents a monocyclic or multicyclic carbocyclic group containing from 6 to 15 carbon atoms and having at least one aromatic ring (e.g., aryl is a phenyl or naphthyl ring), with all available substitutable carbon atoms of the carbocyclic group being intended as possible points of attachment;

arylalkyl represents an aryl group, as defined above, bound to an alkyl group, as defined above, wherein said alkyl group is the point of attachment;

cycloalkyl represents a saturated carbocyclic ring of from 3 to 6 carbon atoms;

cycloalkylene represens a divalent cycloalkyl ring, e.g.

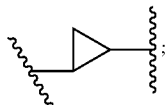

halogen (halo) represents fluoro, chloro, bromo and iodo;

heteroaryl represents a cyclic group having 1 to 4 heteroatoms selected from O, S or N, said heteroatom interrupting a carbocyclic ring structure and having a sufficient number of delocalized pi electrons to provide aromatic character, with the aromatic heterocyclic groups preferably containing from 2 to 14 carbon atoms. The rings do not contain adjacent oxygen and/or sulfur atoms. Examples include but are not limited to isothiazolyl, isoxazolyl, oxazolyl, furazanyl, triazolyl, tetrazolyl, thiazolyl, thienyl, furanyl (furyl), pyrrolyl, pyrazolyl, pyranyl, pyrimidinyl, pyrazinyl, pyridazinyl, pyridyl (e.g., 2-, 3-, or 4-pyridyl), pyridyl N-oxide (e.g., 2-, 3-, or 4-pyridyl N-oxide), triazinyl, pteridinyl, indolyl (benzopyrrolyl), pyridopyrazinyl, isoquinolinyl, quinolinyl, naphthyridinyl; all available substitutable carbon and nitrogen atoms can be substituted as defined;

heterocycloalkyl represents a saturated carbocylic ring containing from 3 to 15 carbon atoms, preferably from 4 to 6 carbon atoms, which carbocyclic ring is interrupted by 1 to 3 hetero atoms selected from —O—, —S—, —SO—, —SO$_2$— or —NR$^{40}$— wherein R$^{40}$ represents H, C$_1$ to C$_6$ alkyl, arylalkyl, —C(O)R$^{30}$, —C(O)OR$^{30}$, or —C(O)N(R$^{30}$)$_2$ (wherein each R$^{30}$ is independently selected from the group consisting of H, alkyl, phenyl and benzyl); examples include but are not limited to 2- or 3-tetrahydrofuranyl, 2- or 3-tetrahydrothienyl, 2-, 3- or 4-piperidinyl, 2- or 3-pyrrolidinyl, 2- or 3-piperizinyl, 2- or 4-dioxanyl, 1,3-dioxolanyl, 1,3,5-trithianyl, pentamethylene sulfide, perhydroisoquinolinyl, decahydroquinolinyl, trimethylene oxide, azetidinyl, 1-azacycloheptanyl, 1,3-dithianyl, 1,3,5-trioxanyl, morpholinyl, thiomorpholinyl, 1,4-thioxanyl, and 1,3,5-hexahydrotriazinyl, thiazolidinyl, tetrahydropyranyl; heterocycloalkylene represens a divalent heterocycloalkyl ring;

heterocycloalkylalkyl represents a heterocycloalkyl group, as defined above, bound to an alkyl group, as defined above, wherein said alkyl group is the point of attachment.

Also, as used herein, "upper airway" usually means the upper respiratory system—i.e., the nose, throat, and associated structures.

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

A line drawn into a ring means that the indicated bond may be attached to any of the substitutable ring carbon atoms.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycloalkyl, R$^5$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of formula I or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyl-oxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$) alkyl, and the like.

Similarly, if a compound of formula I contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)-ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1$-$C_6$)alkyl)$_2$ or glycosyl (the radical resulting from the removal of a hydroxyl group of the hemiacetal form of a carbohydrate), and the like.

If a compound of formula I incorporates an amine functional group, a prodrug can be formed by the replacement of a hydrogen atom in the amine group with a group such as, for example, R"-carbonyl, R"O-carbonyl, NR"R"'-carbonyl where R" and R"' are each independently ($C_1$-$C_{10}$)alkyl, ($C_3$-$C_7$)cycloalkyl, benzyl, or R"-carbonyl is a natural α-aminoacyl or natural α-aminoacyl, —C(OH)C(O)OY$^1$ wherein Y$^1$ is H, ($C_1$-$C_6$)alkyl or benzyl, —C(OY$^2$)Y$^3$ wherein Y$^2$ is ($C_1$-$C_4$)alkyl and Y$^3$ is ($C_1$-$C_6$)alkyl, carboxy($C_1$-$C_6$)alkyl, amino ($C_1$-$C_4$)alkyl or mono-N— or di-N,N—($C_1$-$C_6$)alkylaminoalkyl, —C(Y$^4$)Y$^5$ wherein Y$^4$ is H or methyl and Y$^5$ is mono-N— or di-N,N-($C_1$-$C_6$)alkylamino morpholino, piperidin-1-yl or pyrrolidin-1-yl, and the like.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is H$_2$O.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

One or more compounds of the invention may also exist as, or optionally converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

Compounds of Formula I, and salts, solvates, esters and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

Polymorphic forms of the compounds of Formula I, and of the salts, solvates, esters and prodrugs of the compounds of Formula I, are intended to be included in the present invention.

The compounds of this invention can be combined with an $H_1$ receptor antagonist (i.e., the compounds of this invention can be combined with an $H_1$ receptor antagonist in a pharmaceutical composition, or the compounds of this invention can be administered with an $H_1$ receptor antagonist).

Numerous chemical substances are known to have histamine $H_1$ receptor antagonist activity and can therefore be used in the methods of this invention. Representative $H_1$ receptor antagonists include, without limitation: astemizole, azatadine, azelastine, acrivastine, brompheniramine, cetirizine, chlorpheniramine, clemastine, cyclizine, carebastine, cyproheptadine, carbinoxamine, descarboethoxyloratadine, diphenhydramine, doxylamine, dimethindene, ebastine, epinastine, efletirizine, fexofenadine, hydroxyzine, ketotifen, loratadine, levocabastine, meclizine, mizolastine, mequitazine, mianserin, noberastine, norastemizole, picumast, pyrilamine, promethazine, terfenadine, tripelennamine, temelastine, trimeprazine and triprolidine. Other compounds can readily be evaluated to determine activity at $H_1$ receptors by known methods, including specific blockade of the contractile response to histamine of isolated guinea pig ileum. See for example, WO98/06394 published Feb. 19, 1998.

Those skilled in the art will appreciate that the $H_1$ receptor antagonist is used at its known therapeutically effective dose, or the $H_1$ receptor antagonist is used at its normally prescribed dosage.

Preferably, said $H_1$ receptor antagonist is selected from: azatadine, brompheniramine, cetirizine, chlorpheniramine, carebastine, descarboethoxy-loratadine, diphenhydramine, ebastine, fexofenadine, loratadine, or norastemizole. More preferably, said $H_1$ antagonist is selected from loratadine, descarboethoxyloratadine, fexofenadine or cetirizine.

Preferably, in the above combinations of $H_3$ and $H_1$ antagonists, nasal congestion is treated.

The term "metabolic syndrome" refers to a combination of risk factors for cardiovascular disease (CVD) identified in the National Cholesterol Education Program's Adult Treatment Panel III report. See for example the discussion by Grundy et al in *Circulation*, 109 (2004), 433438. The components of metabolic syndrome are: 1) abdominal obesity; 2) atherogenic dyslipidemia; 3) raised blood pressure; 4) insulin resistance; 5) proinflammatory state; and 6) prothrombotic state.

Weight loss drugs include appetite suppressants, metabolic rate enhancers and nutrient absorption inhibitors. Appetite suppressant agents useful for treating obesity or metabolic syndrome include cannabinoid receptor 1 ($CB_1$) antagonists or inverse agonists (e.g., rimonabant); Neuropeptide Y (NPY1, NPY2, NPY4 and NPY5) antagonists; metabotropic glutamate subtype 5 receptor (mGluR5) antagonists (e.g., 2-methyl-6-(phenylethynyl)-pyridine and 3[(2-methyl-1,4-thiazol-4-yl)ethynyl]pyridine); melanin-concentrating hormone receptor (MCH1R and MCH2R) antagonists; melanocortin receptor agonists (e.g., Melanotan-II and Mc4r agonists); serotonin uptake inhibitors (e.g., dexfenfluramine and fluoxetine); serotonin (5HT) transport inhibitors (e.g., paroxetine, fluoxetine, fenfluramine, fluvoxamine, sertaline and imipramine); norepinephrine (NE) transporter inhibitors (e.g., desipramine, talsupram and nomifensine); ghrelin antagonists; leptin or derivatives thereof; opioid antagonists (e.g., nalmefene, 3-methoxynaltrexone, naloxone and nalterxone); orexin antagonists; bombesin receptor subtype 3 (BRS3) agonists; Cholecystokinin-A (CCK-A) agonists; ciliary neurotrophic factor (CNTF) or derivatives thereof (e.g., butabindide and axokine); monoamine reuptake inhibitors (e.g., sibutramine); glucagons-like peptide 1 (GLP-1) agonists; topiramate; and phytopharm compound 57. Metabolic rate enhancers include acetyl-CoA carboxylase-2 (ACC2) inhibitors; beta adrenergic receptor 3 (β3) agonists; diacylglycerol acyltransferase inhibitors (DGAT1 and DGAT2); fatty acid synthase (FAS) inhibitors (e.g., Cerulenin); phosphodiesterase (PDE) inhibitors (e.g., theophylline, pentoxifylline, zaprinast, sildenafil, amrinone, milrinone, cilostamide, rolipram and cilomilast); thyroid hormone β agonists; uncoupling protein activators (UCP-1, 2 or 3) (e.g., phytanic acid, 4-[(E)-2-(5,6,7,8-tetramethyl-2-naphthalenyl)-1-propenyl]benzoic acid and retinoic acid); acyl-estrogens (e.g., oleoyl-estrone); glucocorticoid antagonists; 11-beta hydroxyl steroid dehydrogenase type 1 (11β HSD-1) inhibitors; melanocortin-3 receptor (Mc3r) agonists; and stearoyl-CoA desaturase-1 (SCD-1) compounds. Nutrient absorption inhibitors include lipase inhibitors (e.g., orlistat, lipstatin, tetrahydrolipstatin, teasaponin and diethylumbelliferyl phosphate); fatty acid transporter inhibitors; dicarboxylate transporter inhibitors; glucose transporter inhibitors; and phosphate transporter inhibitors.

Specific compounds for use in the combination for treating obesity and metabolic syndrome include rimonabant, 2-methyl-6-(phenylethynyl)-pyridine, 3[(2-methyl-1,4-thiazol-4-yl)ethynyl]pyridine, Melanotan-II, dexfenfluramine, paroxetine, fluoxetine, fenfluramine, fluvoxamine, sertaline, imipramine, desipramine, talsupram, nomifensine, leptin, nalmefene, 3-methoxynaltrexone, naloxone, nalterxone, butabindide, axokine, sibutramine, topiramate, phytopharm compound 57, Cerulenin, theophylline, pentoxifylline, zaprinast, sildenafil, amrinone, milrinone, cilostamide, rolipram, cilomilast, phytanic acid, 4-[(E)-2-(5,6,7,8-tetramethyl-2-naphthalenyl)-1-propenyl]benzoic acid, retinoic acid, oleoyl-estrone, orlistat, lipstatin, tetrahydrolipstatin, teasaponin and diethylumbelliferyl phosphate.

Preferred compounds for use in the combination for treating obesity and metabolic syndrome include rimonabant, dexfenfluramine, fenfluramine, phentermine, leptin, nalmefene, axokine, sibutramine, topiramate, phytopharm compound 57, oleoyl-estrone and orlistat.

Also preferred are combinations of one or more compounds of formula I and one or more HMG-CoA reductase inhibitors and/or one or more substituted azetidinone or substituted α-lactam sterol absorption inhibitors for treating metaolic syndrome or obesity.

Typical HMG-CoA reductase inhibitors include statins such as lovastatin, simvastatin, pravastatin, atorvastatin, fluvastatin, resuvastatin, cerivastatin, rivastatin and pitavastatin.

As used herein, "sterol absorption inhibitor" means a compound capable of inhibiting the absorption of one or more sterols, including but not limited to cholesterol, phytosterols (such as sitosterol, campesterol, stigmasterol and avenosterol), 5α-stanols (such as cholestanol, 5α-campestanol, 5α-sitostanol), and/or mixtures thereof, when administered in a therapeutically effective (sterol and/or 5α-stanol absorption inhibiting) amount to a mammal or human.

Non-limiting examples of suitable substituted azetidinones and methods of making the same include those disclosed in U.S. Pat. Nos. RE 37,721, 5,306,817, 5,561,227, 5,618,707, 5,624,920, 5,631,365, 5,656,624, 5,627,176, 5,633,246, 5,661,145, 5,688,785, 5,688,787, 5,688,990, 5,698,548, 5,728,827, 5,739,321, 5,744,467, 5,756,470, 5,767,115, 5,846,966, 5,856,473, 5,886,171, 5,919,672, 6,093,812, 6,096,883, 6,133,001, 6,207,822, 6,627,757, 6,632,933, U.S. Patent Publication Nos. 2003/0105028, 2004/0180860, 2004/0180861, and 2004/0198700, N-sulfonyl-2-azetidinones such as are disclosed in U.S. Pat. No. 4,983,597, ethyl 4-(2-oxoazetidin-4-yl)phenoxy-alkanoates such as are disclosed in Ram et al., Indian J. Chem. Sect. B. 29B, 12 (1990), p. 1134-7, and diphenyl azetidinones and derivatives disclosed in U.S. Patent Publication Nos. 2002/0039774, 2002/0128252, 2002/0128253 and 2002/0137689, and PCT Published Application Nos. WO 2002/066464, WO 04/000805, WO 04/005247, WO 04/000804, WO 04/000803, WO 04/014947, WO 04/087655, WO 05/009955, WO 05/023305, WO 05/021495, WO 05/021497, WO 05/044256, WO 05/042692, WO 05/033100, WO 05/030225, WO 05/047248, WO 05/046662, WO 05/061451, WO 05/061452, WO 05/062824, WO 05/02897, WO 05/000353, each of which is incorporated by reference herein.

An example of a suitable substituted azetidinone compound is represented by Formula (A) (ezetimibe) below:

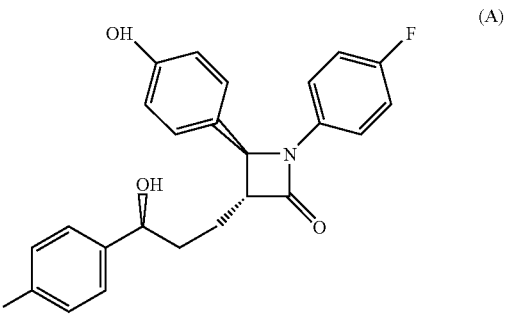

or pharmaceutically acceptable salts or solvates of the compound of Formula (A). The compound of Formula (A) can be in anhydrous or hydrated form. A product containing ezetimibe compound is commercially available as ZETIA® ezetimibe formulation from MSP Pharmaceuticals.

Typical compounds for use in combination with an $H_3$ antagonist of this invention for the treatment of cognition deficit disorders are atomoxetine and dexmethylphenidate for the treatment of ADHD, olanzapine, risperidone or aripiprazole for treatment of schizophrenia, and donepezil, heptylphysostigmine, tacrine, rivastigmine or galantamine for the treatment of Alzheimer's Disease.

In the methods of this invention wherein a combination of an $H_3$ antagonist of this invention is administered with an $H_1$ antagonist or another compound useful for treating obesity, metabolic syndrome or cognition deficit disorders, the $H_3$ antagonist and other compound can be administered simultaneously (at the same time, in a single dosage form or in separate dosage forms) or sequentially (first one and then the other over a period of time).

The preparation of compounds of Formula I can be realized in many ways known to those skilled in the art. Following are typical procedures for preparing various compounds; other procedures may also be applicable and the procedures may be modified to prepare other compounds within the scope of Formula I. One skilled in the art will recognize that one route will be optimal depending on the choice of appendage substituents. Additionally, one skilled in the art will recognize that in some cases the order of steps has to be controlled to avoid functional group incompatibilities.

The compounds of this invention can be prepared through one of the two general approaches outlined below in Schemes 1 and 2; in the structures shown, d and e are each 0, Y is —C(O)— and $M^1$ is N. Scheme 1 shows a convergent synthesis in which AB and CD portions of the molecule are joined together: AB+CD=ABCD.

Scheme 1

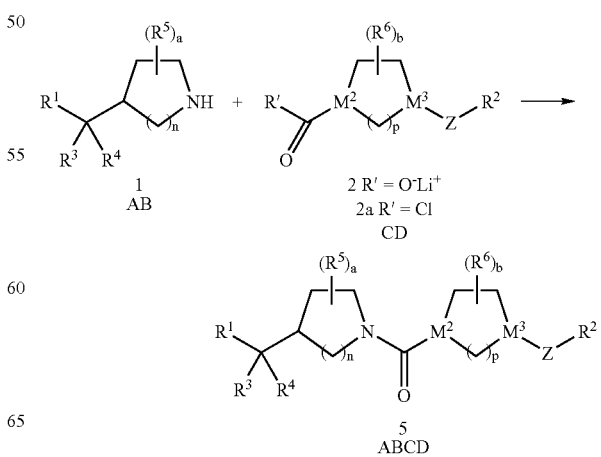

Alternatively, in Scheme 2, the compounds are prepared in a linear synthesis by assembling ABC portion through the coupling of AB and C parts (PG is a protecting group), and then adding on the D fragment (Hal is a halo atom): AB+C=ABC; ABC+D=ABCD.

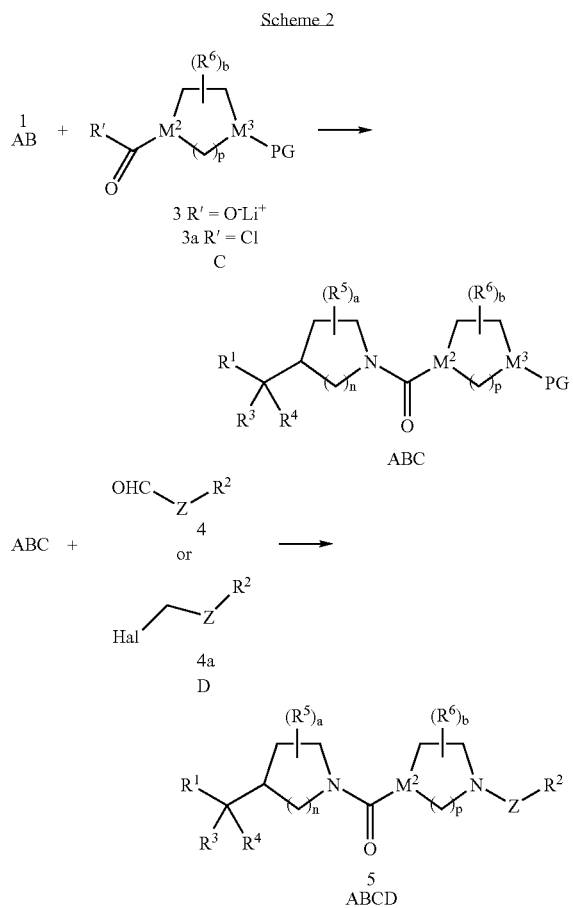

In particular, specific examples of these approaches, where $M^1$—Y constitutes an amide fragment as shown in the schemes, include amide coupling between secondary amine 1, representative of the AB fragment, and carboxylic acid lithium salt 2 or 3, representative of the CD or C fragment, respectively. Alternatively, carboxylic acid lithium salt 2 or 3 is converted into the corresponding acid chloride 2a or 3a and then coupled with amine 1. Conversion of the ABC intermediate into the final compound is accomplished, for example, in the particular case when $M^3$ represents N, through deprotection of the secondary amine, followed by its reaction with an electrophilic D fragment, which most typically is an aldehyde 4 (reductive amination) or a halide 4a (alkylation) (Scheme 2), but also can be represented by an epoxide or other electrophile. Depending on the nature of groups $R^1$, $R^2$, $R^3$ and $R^4$, the last step in either synthetic sequence will involve cleavage of the protecting groups present in the molecule to yield final compounds 5.

In cases, where $M^1$—Y-$M^2$ constitutes a ketone (i.e., $M^1$ is CH, Y is —C(O)— and $M^2$ is CH), connection between B and C fragments may be established through the reaction of appropriate B ring-based carbon nucleophile (e.g., Grignard reagent or a transition metal-based reagent (Zn, Pd, Sn)), derived from the corresponding B-ring cycloalkyl halide, with a C ring-based Weinreb amide or aldehyde, generated from acid 3 (see Scheme 2), or any other suitable electrophile, such as, for example, a vinyl halide. Those skilled in the art will recognize that this approach may need to be followed by well-known synthetic procedures to finish elaboration of the ketone functionality, such as oxidation of an alcohol, or ozonolysis of an alkene.

Various examples of C and D fragments, as well as methods employed in the synthesis of the CD portion, the C and D parts separately, and the addition of C and then D fragments onto the initial AB fragment have been previously described, e.g., in U.S. Pat. No. 6,720,378 and US 2004/0097483.

Assembly of the AB portion of the molecule is achieved as shown in Scheme 3.

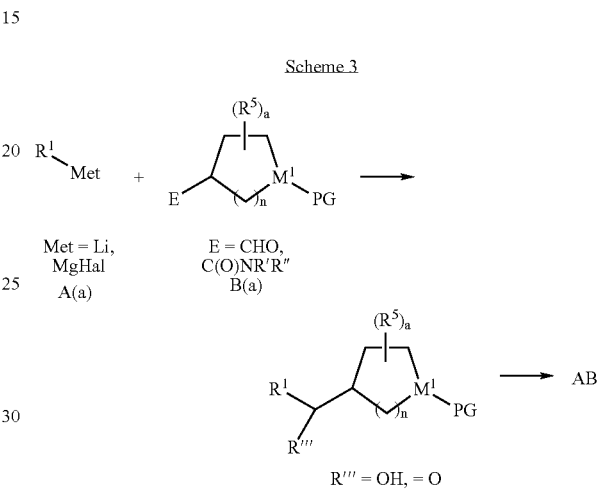

Intermediates AB are prepared through the reaction of an organometallic reagent of the type A(a), derived from $R^1$ where, most typically, Met is Li or MgCl, but can also be mediated by a transition metal, e.g. Pd, with an appropriate electrophile of the type B(a), which most typically is an aldehyde or an amide, but can also be an alkylborane or other common electrophile. The reaction between A(a) and B(a) is then followed by functional transformations to install the desired groups $R^3$ and $R^4$. Detailed procedures employed in the synthesis of various AB fragments are described in the examples below.

The starting material and reagents used in preparing compounds described are either available from commercial suppliers such as Aldrich Chemical Co. (Wisconsin, USA) and Acros Organics Co. (New Jersey, USA) or were prepared by literature methods known to those skilled in the art.

Compounds of formula I can be prepared by the general methods outlined above. Specifically exemplified compounds were prepared as described in the examples below, from starting materials known in the art or prepared as described below. These examples are being provided to further illustrate the present invention. They are for illustrative purposes only; the scope of the invention is not to be considered limited in any way thereby.

Unless otherwise stated, the following abbreviations have the stated meanings in the Examples below:
Me=methyl; Et=ethyl; Bu=butyl; Pr=propyl; Ph=phenyl; t-BOC or BOC=tert-butoxycarbonyl; and Ac=acetyl
9-BBN=9-borabucyclo[3.3.1]nonane
DAST=diethylaminosulfur trifluoride
DCM=dichloromethane
DIBAL=diisobutylaluminium hydride
DIPEA=diisopropylethylamine DMAP=4-dimethylaminopyridine
DMF=dimethylformamide
DMSO=dimethyl sulfoxide
EDCl=1-(3-dimethylaminopropyl)-3-ethylcarbodiimide
HOBT=1-hydroxybenzotriazole
rt=room temperature
TBSCl=tert-butyldimethylsilyl chloride
TFA=trifluoroacetic acid
THF=tetrahydrofuran
TEMPO=2,2,6,6-tetramethyl-1-piperidinyloxy, free radical
TLC=thin layer chromatography
HRMS=High Resolution Mass Spectrometry
LRMS=Low Resolution Mass Spectrometry
nM=nanomolar
Ki=Dissociation Constant for substrate/receptor complex
pA2=−logEC$_{50}$, as defined by J. Hey, *Eur. J. Pharmacol.*, (1995), Vol. 294, 329-335.
Ci/mmol=Curie/mmol (a measure of specific activity)

EXAMPLE 1

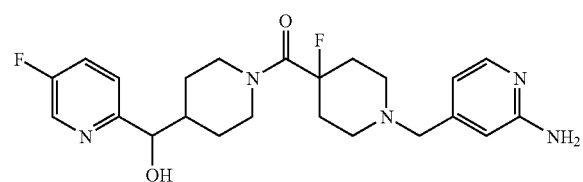

Step 1:

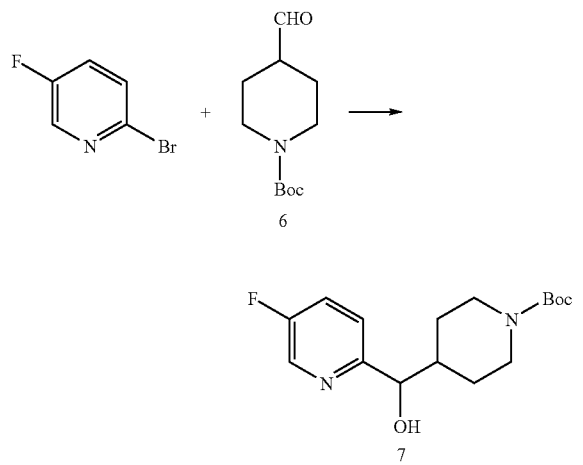

A solution of 2-bromo-5-fluoropyridine (2.0 g, 11.4 mmol) in toluene (20 ml) was added slowly to a solution of n-BuLi (5.0 ml, 12.5 mmol) in toluene (80 ml) cooled to −78° C. and the mixture was stirred at −78° C. for 30 min. A solution of aldehyde 6 (3.64 g, 17.0 mmol) in toluene (20 ml) was added and the reaction mixture was stirred at −78° C. for 2 h. It was quenched with AcOH at −78° C. and diluted with water. The product was extracted with CH$_2$Cl$_2$ and the organic layer was dried over Na$_2$SO$_4$. Purification by flash chromatography (0-1% 2N NH$_3$ in MeOH/CH$_2$Cl$_2$) provided 3.50 g (99%) of alcohol 7 as a yellowish oil.

Step 2:

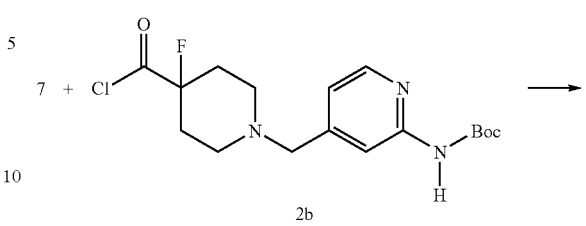

A solution of amine 7 (315 mg, 1.02 mmol) in TFA/CH$_2$Cl$_2$ (10 ml of 25%) was stirred for 6 h at rt. The mixture was concentrated under vacuum and the residue was subjected to flash chromatography (4% 2N NH$_3$ in MeOH/CH$_2$Cl$_2$) to yield the free amine (176 mg, 0.84 mmol). The amine was combined with the acid chloride 2d (see step 2 of Example 2 (452 mg; 1.26 mmol) in CH$_2$Cl$_2$ (15 ml) with 1 drop of DMF, stirring for 1 h at rt and concentrating to dryness under vacuum] and DIPEA (0.51 ml; 2.93 mmol) in CH$_2$Cl$_2$ (20 ml). The mixture was stirred for 2 h at rt, subjected to aqueous NaHCO$_3$ work-up —CH$_2$Cl$_2$ extraction, followed by flash chromatography (1-2% 2N NH$_3$ in MeOH/CH$_2$Cl$_2$), to produce the coupled product (153 mg, 0.28 mmol) as an off-white solid. The solid was dissolved in TFA/CH$_2$Cl$_2$ (10 ml of 25%) and the solution was stirred for 6 h at rt. The mixture was concentrated under vacuum and the residue was subjected to aqueous NaHCO$_3$ work-up —CH$_2$Cl$_2$ extraction, followed by flash chromatography (24% 2N NH$_3$ in MeOH/CH$_2$Cl$_2$) to yield 94 mg (0.21 mmol) of the title compound as white solid. MS (M+H): 446.

EXAMPLE 2

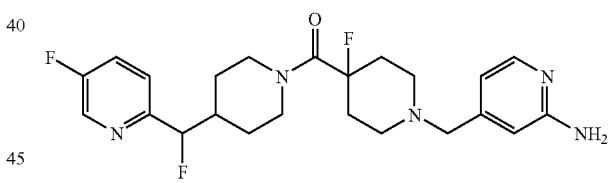

Step 1:

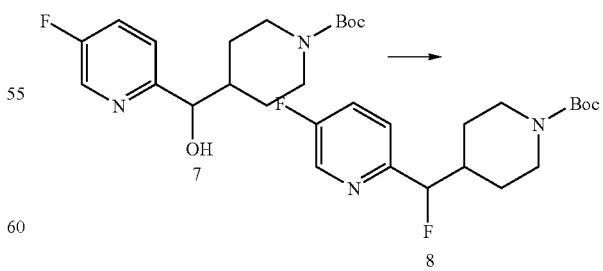

To a solution of alcohol 7 (1.0 g, 3.22 mmol) in CH$_2$Cl$_2$ (15 ml) cooled to −78° C. was added DAST (0.51 ml, 3.87 mmol) and the reaction mixture was stirred at −78° C. for 1 h. It was warmed up to rt and stirred for 1 h. Water was added, followed by saturated aqueous NaHCO₃ solution. The product was extracted with CH₂Cl₂ and the organic layer was dried over Na₂SO₄. Purification by flash chromatography (1-2% EtOAc/CH₂Cl₂) provided 8 (0.614 g, 1.97 mmol) as a yellowish oil.

Step 2:

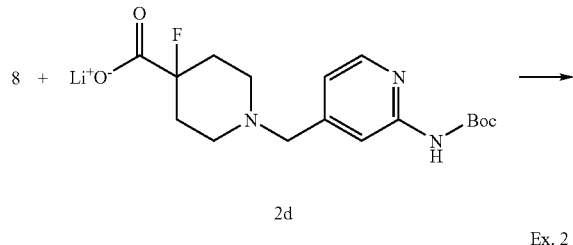

The solution of Boc-protected amine 8 in TFA/CH₂Cl₂ (20 ml of 25%) was stirred for 6 h at rt. The mixture was concentrated under vacuum and the residue was subjected to aqueous NaHCO₃ work-up —CH₂Cl₂ extraction to produce crude free amine (417 mg) as yellowish oil. For the amide coupling, crude amine (83 mg) was combined with N-Boc-acid lithium salt 2d (167 mg, 0.47 mmol) [prepared as described in steps 14 of Example 31 of WO2002/032893, herein incorporated by reference], HOBT (79 mg, 0.58 mmol), Et₃N (0.13 ml, 0.97 mmol) and EDCl 112 mg, 0.58 mmol) in CH₂Cl₂-DMF (10 ml of 1:1 mixture). The mixture was stirred for 8 h at 70° C. and then at rt overnight. Aqueous NaHCO₃ work-up, CH₂Cl₂ extraction and flash chromatography (1-2% MeOH/CH₂Cl₂) provided coupled product (145 mg) as a white solid. Subsequent deprotection with TFA/CH₂Cl₂, as described in Example 1, yielded 118 mg (0.26 mmol) of the title compound as yellowish foam. MS (M+H): 448.

EXAMPLE 3

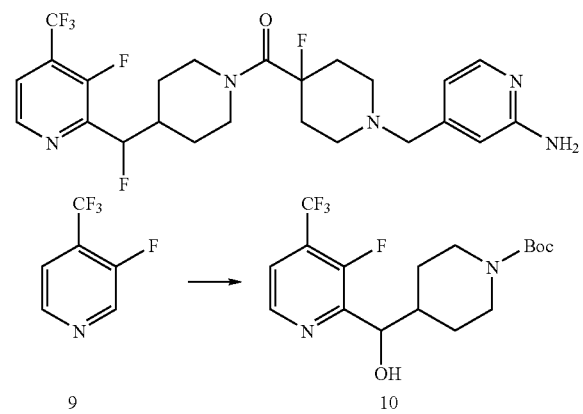

To a −78° C. solution of pyridine 9 (1.00 g, 6.06 mmol) in of THF (40 ml) was added BuLi solution (2.4 ml of 2.5M) in hexanes (6.00 mmol), and the reaction mixture was stirred for 1 h at −78° C. A solution of aldehyde 6 (1.90 g; 8.91 mmol) in THF was then added, and reaction mixture was stirred at −78° C. for additional 2 h. The reaction mixture was quenched with water and AcOH to pH 7, then extracted with CH₂Cl₂. The organic phase was concentrated and the residue was flash chromatographed (1% MeOH/CH₂Cl₂) to produce 10 (660 mg, 1.74 mmol) as a yellow oil.

BOC-deprotection and amide coupling steps as described in Example 2 were used to obtain the title compound MS (M+H): 516.

EXAMPLE 4

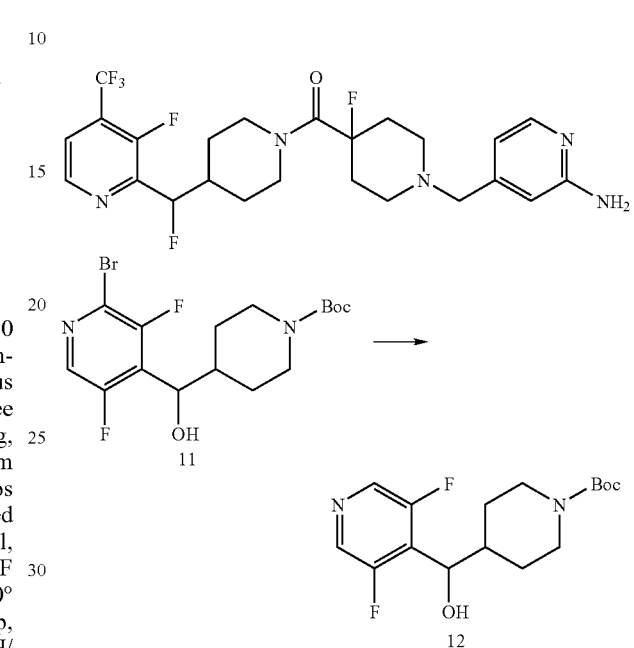

To a solution of alcohol 11 (0.40 g, 0.98 mmol) [prepared as described in Example 3] in 1,4-dioxane (5 ml) was added aqueous NaOH (0.08 g, 2.00 mmol) solution (5 ml) followed by zinc powder (0.18 g, 2.75 mmol), and the reaction mixture was stirred at rt overnight. The mixture was neutralized with saturated aqueous NH₄Cl solution, and the product was extracted with CH₂Cl₂. Purification by flash chromatography (0-1% MeOH/CH₂Cl₂) provided 12 (0.26 g, 0.79 mmol) as a clear oil.

Subsequent conversion into the title compound was effected as described in previous examples. MS (M+H): 451.

EXAMPLE 5

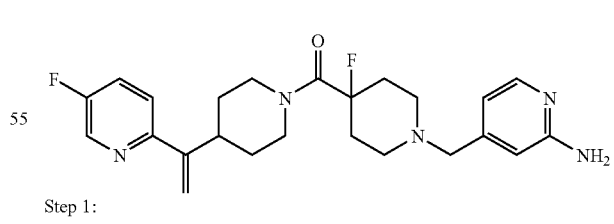

Step 1:

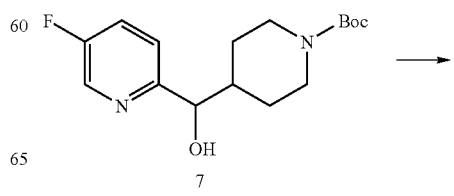

-continued

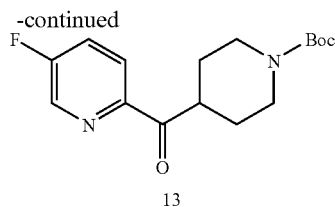

13

To a solution of alcohol 7 (9.0 g, 29.0 mmol) in CH$_2$Cl$_2$ (200 ml) was added saturated aqueous solution of NaHCO$_3$ (3.0 g, 35.6 mmol) and NaBr (0.15 g, 1.49 mmol). The mixture was cooled to 0° C. and TEMPO (0.05 g, 0.32 mmol) was added followed by commercial bleach (NaOCl) (0.7 M, 85 ml, 59.5 mmol) in portions over 15 min. The reaction mixture was stirred at 0° C. for 30 min and then quenched with saturated aqueous Na$_2$S$_2$O$_3$ solution. The product was extracted with CH$_2$Cl$_2$ and the organic layer was dried over Na$_2$SO$_4$. Purification by flash chromatography (CH$_2$Cl$_2$) provided 6.31 g of 13 as a yellowish oil.

Step 2:

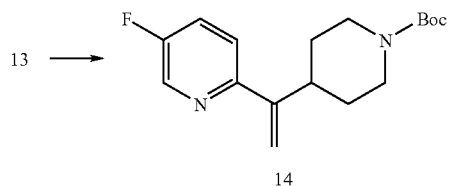

14

To a suspension of methyltriphenylphosphonium bromide (6.08 g, 17.0 mmol) in THF (60 ml), cooled to −78° C., was added n-BuLi (6.48 ml of 2.5M soln. in hexanes; 16.2 mmol), and the mixture was stirred at −78° C. for 30 min and then at 0° C. for 45 min. It was cooled back to −78° C. and a solution of ketone 13 (2.50 g, 8.1 mmol) in THF (20 ml) was added. The reaction mixture was stirred at −78° C. for 30 min and warmed up to rt. It was quenched with water, and the product was extracted with CH$_2$Cl$_2$. The organic layer was dried over Na$_2$SO$_4$ and purified by flash chromatography (1:9:10 EtOAc/hexanes/CH$_2$Cl$_2$) to provide 1.45 g of 14 as a yellow oil.

BOC-deprotection and amide coupling steps as described in Example 2 were used to obtain the title compound MS (M+H): 442.

EXAMPLE 6

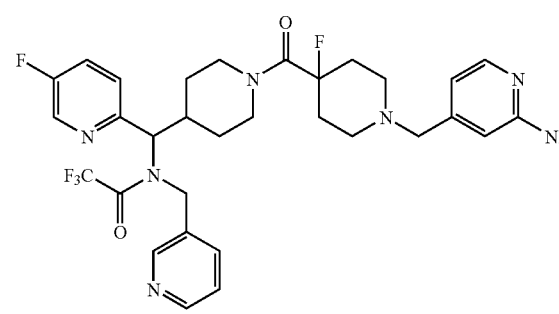

Step 1:

13 →

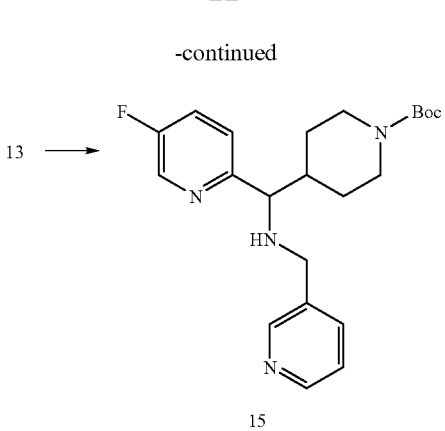

15

To a solution of ketone 13 (0.60 g, 1.95 mmol) and 3-(aminomethyl)pyridine (0.24 ml, 2.34 mmol) in CH$_2$Cl$_2$ (2 ml) was added Ti(Oi—Pr)$_4$ (1.16 ml, 3.89 mmol), and the mixture was stirred at rt overnight. It was then cooled to 0° C. and a solution of NaBH$_3$CN (0.37 g, 5.84 mmol) in MeOH (4 ml) was added. The reaction mixture was stirred at rt for 5 h and neutralized with 1 N aqueous NaOH solution. The product was extracted with CH$_2$Cl$_2$ and the organic layer was dried over Na$_2$SO$_4$. Purification by flash chromatography (1-3% MeOH/CH$_2$Cl$_2$) provided 0.35 g of 15 as a yellowish oil.

Step 2:

15 →

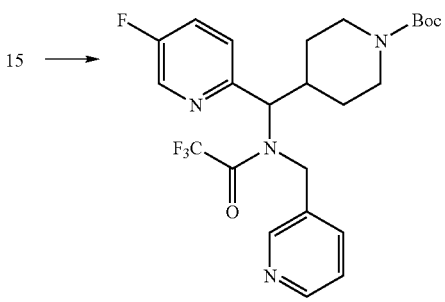

To a solution of amine 15 (0.076 g, 0.19 mmol) in CH$_2$Cl$_2$ (3 ml) was added trifluoroacetic anhydride (0.04 ml, 0.28 mmol) followed by Et$_3$N (0.08 ml, 0.57 mmol); the reaction mixture was stirred at rt for 3 h. It was quenched with saturated aqueous NaHCO$_3$ solution and the product was extracted with CH$_2$Cl$_2$. The organic layer was dried over Na$_2$SO$_4$ and concentrated to provide 0.094 g of 16 as a yellowish oil.

BOC-deprotection and amide coupling steps as described in Example 2 were used to obtain the title compound MS (M+H): 632.

EXAMPLE 7

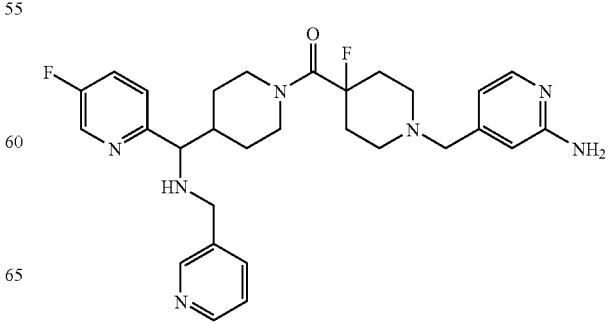

A solution of Example 6 (0.010 g, 0.016 mmol) in EtOH (1 ml) was treated with NaBH$_4$ (0.006 g, 0.16 mmol) at 60° C. for 3 hr. The reaction mixture was quenched with saturated aqueous NaHCO$_3$ solution and the product was extracted with CH$_2$Cl$_2$. The organic layer was dried over Na$_2$SO$_4$ and purified by prep. TLC (10% MeOH/CH$_2$Cl$_2$) to provide the title compound (0.004 g) as a yellowish solid. MS (M+H): 536.

EXAMPLE 8

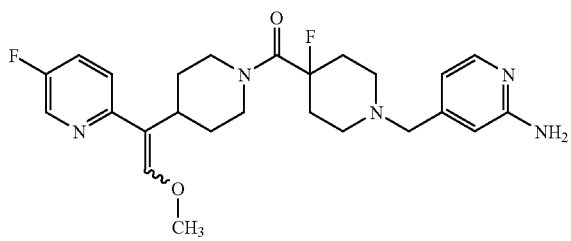

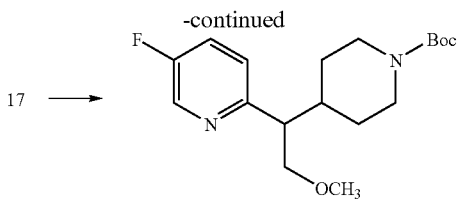

To a suspension of (methoxymethyl)triphenylphosphonium chloride (3.50 g, 10.2 mmol) in THF (30 ml), cooled to −78° C., was added slowly n-BuLi (3.89 ml of 2.5M soln. in hexanes, 9.73 mmol), and the orange mixture was stirred at −78° C. for 30 min and then at 0° C. for 45 min. It was cooled back to −78° C. and a solution of ketone 13 (1.50 g, 4.86 mmol) in THF (20 ml) was added. The reaction mixture was stirred at −78° C. for 30 min and warmed up to rt. It was quenched with water and the product was extracted with CH$_2$Cl$_2$. The organic layer was dried over Na$_2$SO$_4$ and purified by flash chromatography (0–1% EtOAC/CH$_2$Cl$_2$) to provide 1.36 g (83%) of 17 as a yellowish oil.

BOC-deprotection and amide coupling steps as described in Example 2 were used to obtain the title compound MS (M+H): 472.

EXAMPLE 9

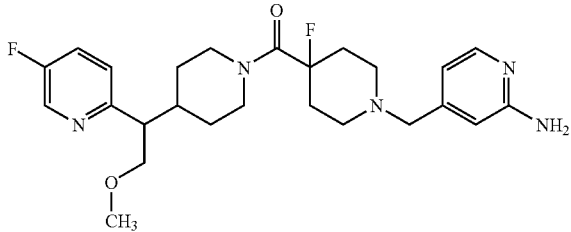

To a solution of 17 (0.15 g, 0.46 mmol) in MeOH (5 ml) was added 10% Pd/C (0.05 g, 0.047 mmol), and the reaction mixture was stirred at rt under H$_2$ (1 atm.) overnight. The catalyst was filtered off on celite and washed with MeOH. The filtrate was concentrated to provide 0.15 g of 18 as a yellowish oil.

BOC-deprotection and amide coupling steps as described in Example 2 were used to obtain the title compound MS (M+H): 474.

EXAMPLE 10

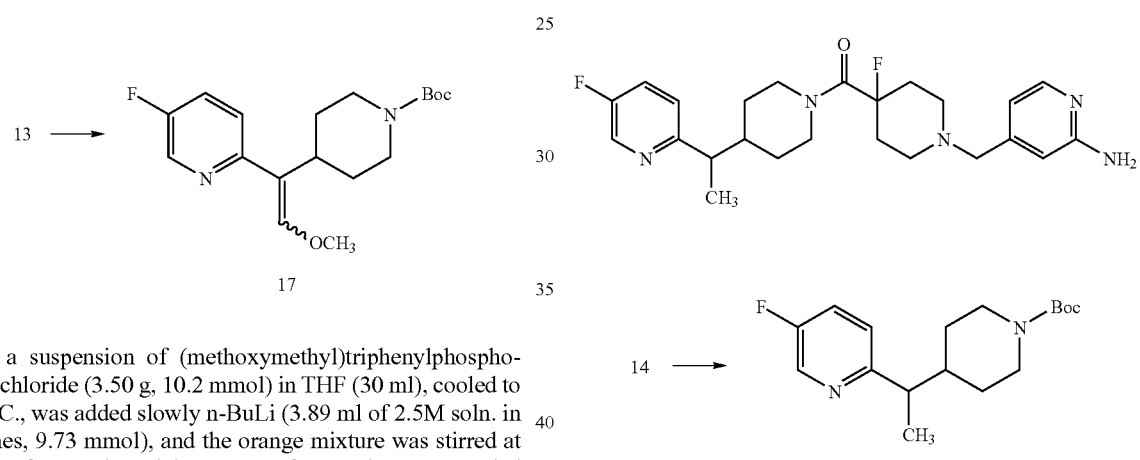

Compound 19 was prepared from compound 14 using the same procedure as in Example 9.

BOC-deprotection and amide coupling steps as described in Example 2 were used to obtain the title compound MS (M+H): 444.

EXAMPLE 11

Step 1:

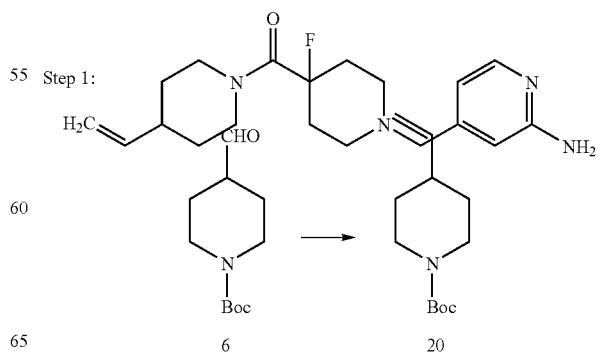

To a suspension of methyltriphenylphosphonium bromide (1.76 g, 4.93 mmol) in THF (30 ml), cooled to −78° C., was added n-BuLi (1.88 ml of 2.5M soln. in hexanes; 4.68 mmol), and the mixture was stirred at −78° C. for 30 min and then at 0° C. for 45 min. It was cooled back to −78° C., and a solution of aldehyde 6 (0.50 g, 2.34 mmol) in THF (5 ml) was added. The reaction mixture was stirred at −78° C. for 30 min and warmed up to rt. It was quenched with water, and the product was extracted with $CH_2Cl_2$. The organic layer was dried over $Na_2SO_4$ and purified by flash chromatography (0.5% MeOH/ $CH_2Cl_2$) to provide 0.24 g of 20 as a clear oil.

Step 2: BOC-deprotection and amide coupling steps as described in Example 2 were used to obtain the title compound MS (M+H): 347.

EXAMPLE 12

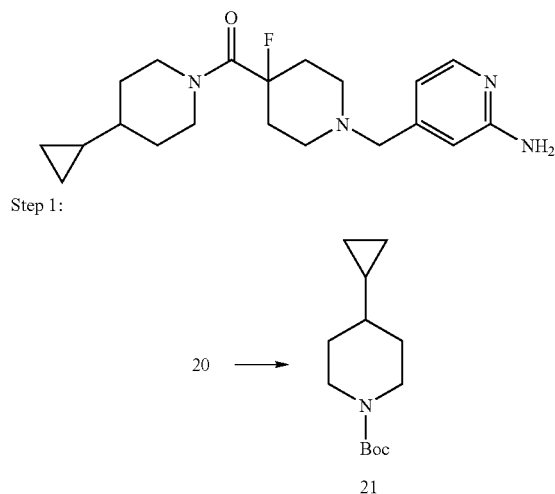

1-Methyl-3-nitro-1-nitrosoguanidine (3.00 g, 20.4 mmol) was added in small portions with agitation to a mixture of 5M aqueous NaOH solution (14 ml) and ether (70 ml), cooled to 0° C. The yellow ether layer was decanted into a flask precooled in an ice bath and containing a few KOH pellets for drying. To a solution of olefin 20 (0.20 g, 0.95 mmol) in ether (5 ml) cooled to 0° C. was added Pd(OAc)$_2$ (0.006 g, 0.03 mmol), followed by the ethereal $CH_2N_2$ solution in portions (prepared as described above), and the reaction mixture was stirred at rt for 5 hr. It was quenched with AcOH and diluted with saturated aqueous NaHCO$_3$ solution. The product was extracted with $CH_2Cl_2$ and the organic layer was dried over $Na_2SO_4$. Purification by flash chromatography ($CH_2Cl_2$) provided 0.16 g of 21 as a clear liquid.

Step 2: BOC-deprotection and amide coupling steps as described in Example 2 were used to obtain the title compound MS (M+H): 361.

EXAMPLE 13

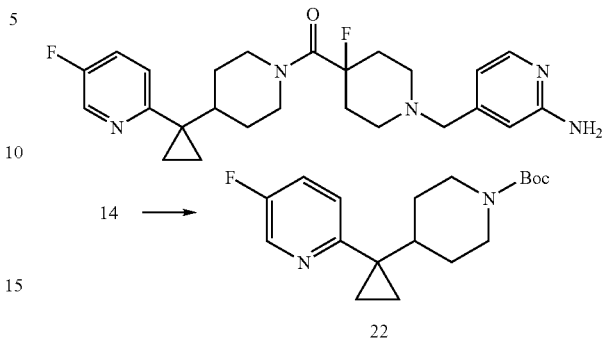

Compound 22 was prepared by the same procedure as in the first paragraph of Example 12. BOC-deprotection of 22 and amide coupling steps as described in Example 2 were used to obtain the title compound MS (M+H): 456.

EXAMPLE 14

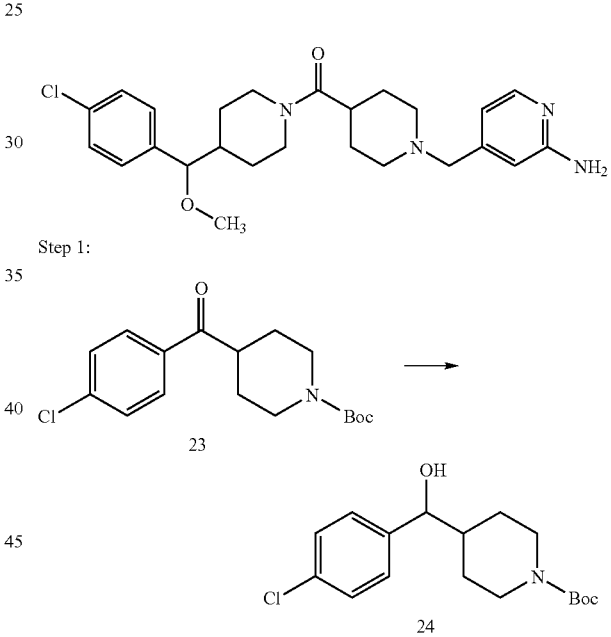

To a suspension of compound 23 (6.20 g, 19.2 mmol) in isopropanol (250 ml) was added NaBH$_4$ (0.91 g, 24.0 mmol). The reaction mixture was stirred at rt for 16 h. The solvent was evaporated, the crude product was dissolved in $CH_2Cl_2$ (200 ml) and washed with water. The organic extract was dried (MgSO$_4$), filtered and concentrated to give 6.10 g (18.7 mmol, 98%) of the product 24 as a white solid.

Step 2:

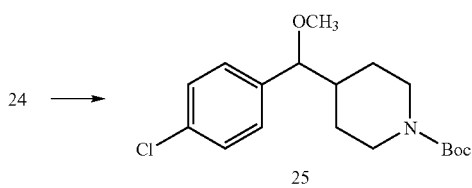

To a solution of compound 24 (1.00 g, 3.07 mmol) dissolved in dry DMF (20 ml) and cooled to 0° C. under N₂, was added KN(TMS)₂ (0.5 M in toluene, 7.4 ml, 3.68 mmol) via syringe. The reaction mixture was stirred at 0° C. for 30 mins then CH₃I (0.65 g, 0.29 ml, 4.60 mmol) was added. The resulting solution was stirred at rt for 16 h. The solvent was evaporated, water (50 ml) was added, and the product was extracted with CH₂Cl₂. The combined organic extract was dried (MgSO₄), filtered and concentrated. Purification by silica gel chromatography (5% EtOAc/CH₂Cl₂) gave 0.80 g (2.35 mmol, 80%) of the product 25 as an oil.

Step 3:

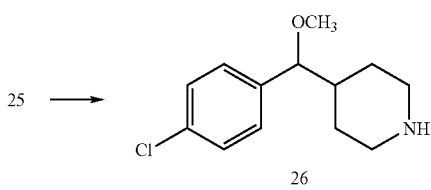

To a solution of compound 25 (0.80 g, 2.35 mmol) dissolved in CH₂Cl₂ (15 ml) was added 4 N HCl in dioxane (3.5 ml, 14.1 mmol). The reaction mixture was stirred at rt for 6 h, and then concentrated to give 0.65 g (2.35 mmol, 100%) of the product 26 as a white foam.

Step 4:

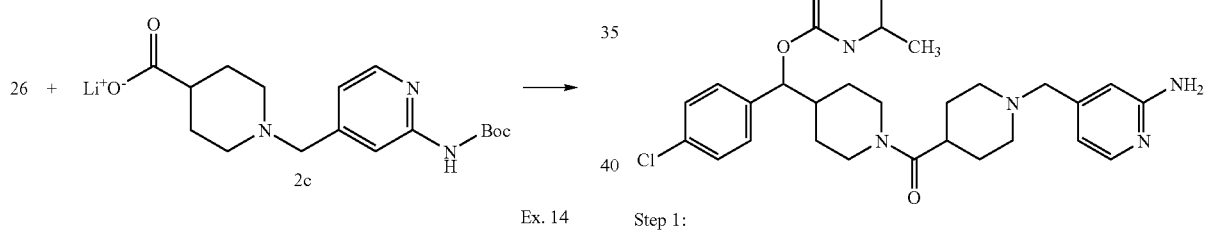

The amine 26 was coupled with N-Boc-carboxylic acid lithium salt 2c [prepared following the procedure described in steps 1-5 of Example 1 in WO2002/032893], was prepared in a manner similar to that described in Example 2 to obtain the title compound. MS (M+H): 457

EXAMPLE 15

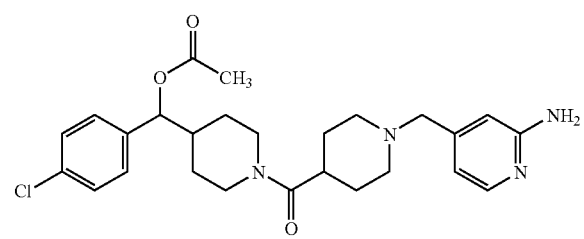

Step 1:

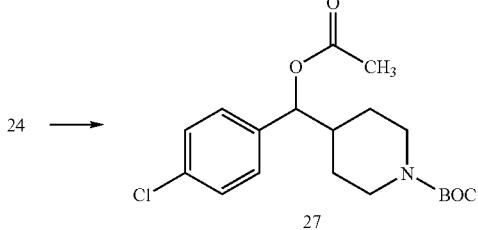

To a solution of compound 24 (1.00 g, 3.07 mmol) dissolved in CH₂Cl₂ (20 ml) was added Et₃N (0.93 g, 1.3 ml, 9.21 mmol) and acetyl chloride (0.48 g, 0.44 ml, 6.14 mmol). The reaction mixture was heated at reflux for 16 h. Water (30 ml) was added, and the product was extracted with CH₂Cl₂. The combined organic extract was dried (MgSO₄), filtered, and concentrated. Purification by silica gel chromatography (5% EtOAc/CH₂Cl₂) gave 0.60 g (1.63 mmol, 53%) of the product 27 as a colorless oil.

Step 2: The amine 27 was deprotected and coupled with carboxylic acid lithium salt 2c in a manner similar to that described in Example 2 to obtain the title compound.
MS (M+H): 485.

EXAMPLE 16

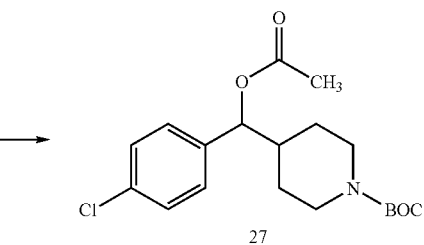

Step 1:

To a solution of compound 24 (0.60 g, 1.84 mmol) dissolved in dry THF (10 ml) was added isopropylisocyanate (0.36 g, 0.41 ml, 4.14 mmol). The reaction mixture was heated at reflux for 16 h. The solvent was evaporated, water (30 ml) was added, and the product was extracted with CH₂Cl₂. The combined organic extract was dried (MgSO₄), filtered, and concentrated. Purification by silica gel chromatography (1:2 EtOAc:hexane) gave 0.75 g (1.863 mmol, 99%) of the product 28 as a white foam.

Step 2: The amine 28 was deprotected and coupled with carboxylic acid lithium salt 2c in a manner similar to that described in Example 2 to obtain the title compound.
MS (M+H): 528.

EXAMPLE 17

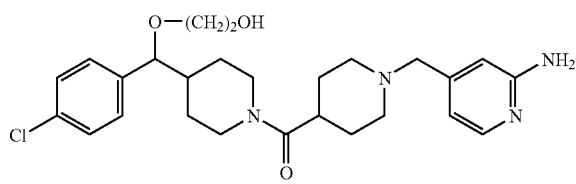

Step 1:

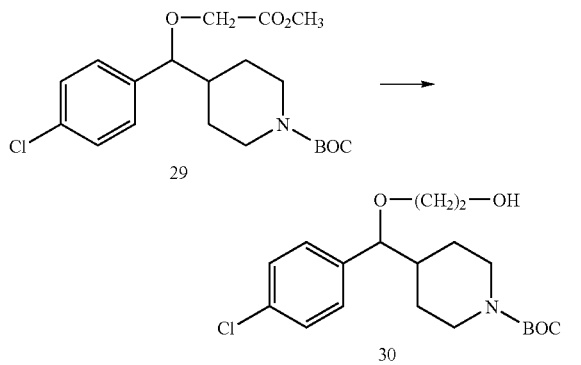

To a solution of compound 29 (1.00 g, 2.51 mmol) [prepared from alcohol 24 and methyl bromoacetate as described in Example 14] dissolved in dry THF (20 ml) and cooled to 0° C., was added LiAlH$_4$ (0.095 g, 2.51 mmol). The reaction mixture was stirred at 0° C. for 30 min then at rt for 3 h. Water (0.1 ml) was carefully added, then 1 N NaOH (0.1 ml), then water (0.3 ml). CH$_2$Cl$_2$ was added and stirred at rt for 30 min. Aluminum salts were filtered and the solid was washed with CH$_2$Cl$_2$. The filtrate was concentrated, and purification by silica gel chromatography (eluant: 1:1 EtOAc:hexane) gave 0.70 g (1.89 mmol, 75%) of the product 30 as a colorless oil.

Step 2: The amine 30 was deprotected and coupled with carboxylic acid lithium salt 2c in a manner similar to that described in Example 2 to obtain the title compound.

MS (M+H): 487.

EXAMPLE 18

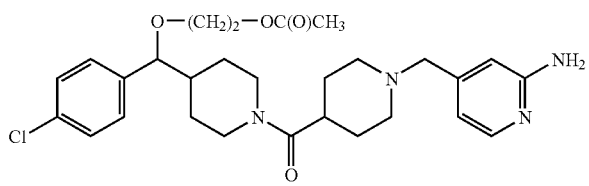

Step 1:

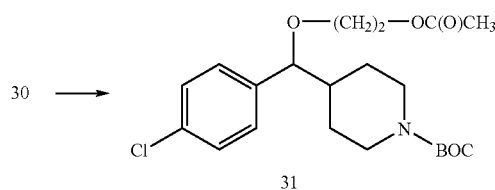

Compound 31 was prepared form compound 30 using the procedure described in Example 15.

Step 2: The amine 31 was deprotected and coupled with carboxylic acid lithium salt 2c in a manner similar to that described in Example 2 to obtain the title compound.

MS (M+H): 529.

EXAMPLE 19

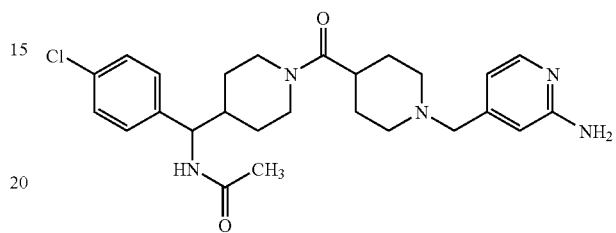

Step 1:

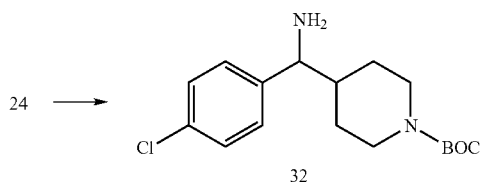

To a solution of compound 24 (5.28 g, 16.2 mmol) dissolved in CH$_2$Cl$_2$ (75 ml) and cooled to 0° C., was added Et$_3$N (3.28 g, 4.5 ml, 32.4 mmol) and then CH$_3$SO$_2$Cl (2.32 g, 1.6 ml, 20.3 mmol) dropwise via syringe. The reaction mixture was stirred at 0° C. for 1 h and then at rt for 1 h. Water (100 ml) was added, and the product was extracted with CH$_2$Cl$_2$. The combined organic extract was dried (MgSO$_4$), filtered, and concentrated to give 6.54 g (16.2 mmol, 100%) of the mesylate intermediate as a white solid.

To a solution of mesylate (6.54 g, 16.2 mmol) in DMF (60 ml) was added NaN$_3$ (2.10 g, 32.4 mmol). The reaction mixture was heated at 80° C. for 3 h. The solvent was evaporated, water was added, and the product was extracted with CH$_2$Cl$_2$. The combined organic extract was dried (MgSO$_4$), filtered, and concentrated to give 5.68 g (16.2 mmol, 100%) of the azide intermediate as a yellow oil.

To a solution of azide (5.68 g, 16.2 mmol) in THF (80 ml) and water (8 ml) was added triphenylphosphine (25.5 g, 97.2 mmol). The reaction mixture was heated at reflux for 16 h. The solvent was evaporated, water was added, and the product was extracted with CH$_2$Cl$_2$. The combined organic extract was dried (MgSO$_4$), filtered, and concentrated. Purification by silica gel chromatography (eluant: 5%-10% MeOH —CH$_2$Cl$_2$) gave 4.15 g (12.8 mmol, 79%) of the product 32 as a yellow oil.

Step 2:

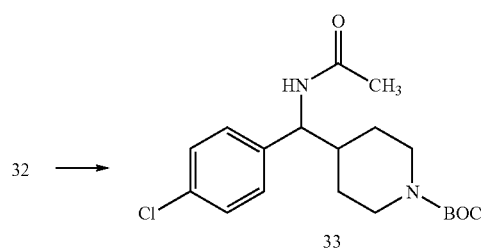

Compound 33 was prepared from compound 32 using the procedure of EXAMPLE 15.

Step 3:

The Boc-protected amine 33 was deprotected and coupled with carboxylic acid lithium salt 2c in a manner similar to that described in Example 2 to obtain the title compound. MS (M+H): 485.

EXAMPLE 20

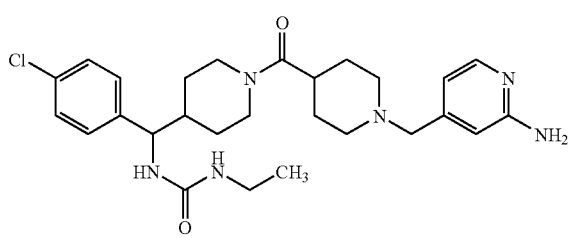

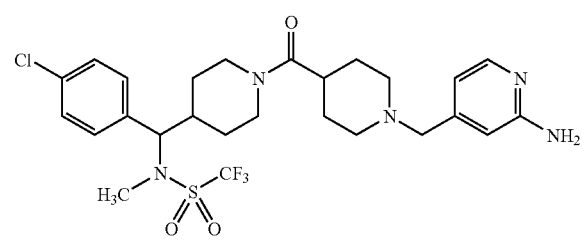

Using the procedure of Example 15, compound 34 was prepared form compound 32.

The amine 34 was deprotected and coupled with carboxylic acid lithium salt 2c in a manner similar to that described in Example 2 to obtain the title compound. MS (M+H): 513.

EXAMPLE 21

-continued

Step 1:

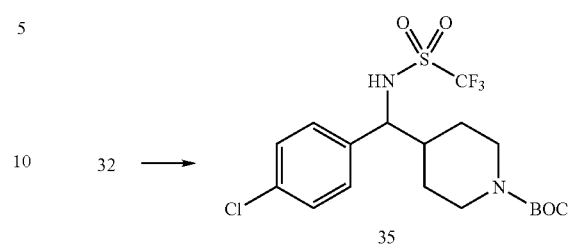

Compound 35 was prepared from compound 32 using the procedure of EXAMPLE 16.

Step 2:

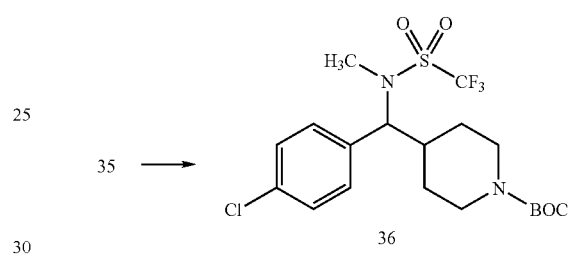

Compound 36 was prepared from compound 35 using the procedure of Example 14 for preparing compound 25.

Step 3:

The amine 36 was deprotected and coupled with carboxylic acid lithium salt 2c in a manner similar to that described in Example 2 to obtain the title compound. MS (M+H): 588.

EXAMPLES 22 AND 22A

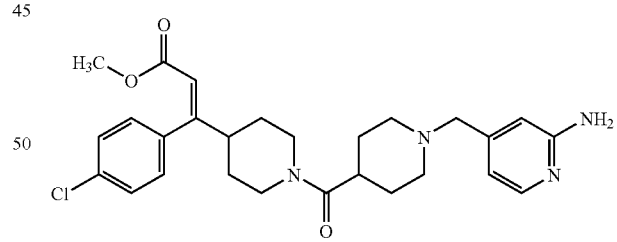

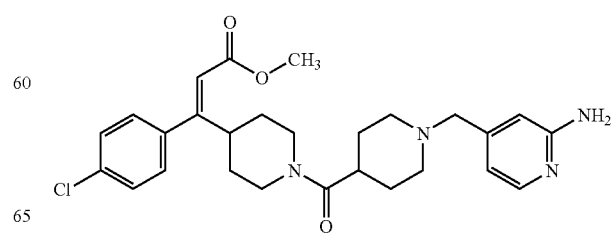

Step 1:

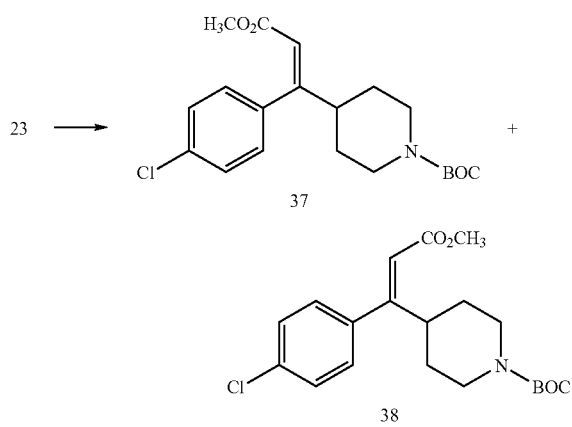

To a suspension of NaH (60 wt % in oil, 2.17 g, 54.3 mmol) in dry DMF (30 ml) cooled to 0° C., was added trimethyl phosphonoacetate (9.90 g, 54.3 mmol). The reaction mixture was stirred at rt for 15 min, then compound 23 (5.86 g, 18.1 mmol) in 50 ml of dry DMF was added dropwise via addition funnel. The resulting solution was heated at 80° C. for 16 h. The solvent was evaporated, water was added, and the product was extracted with EtOAc. The combined organic extract was dried (MgSO$_4$), filtered, and concentrated. Purification by silica gel chromatography (eluant: 10% EtOAc-hexane) gave 1.01 g (2.66 mmol, 15%) of the cis product 37, 3.36 g (8.85 mmol, 49%) of the cis and trans mixture of 37 and 38, and 2.05 g (5.40 mmol, 30%) of the trans product of 38.

Step 2: The amines 37 and 38 were deprotected and coupled with carboxylic acid lithium salt 2c in a manner similar to that described in Example 2 to obtain the title compounds. MS (M+H): 497.

EXAMPLE 23 AND 23A

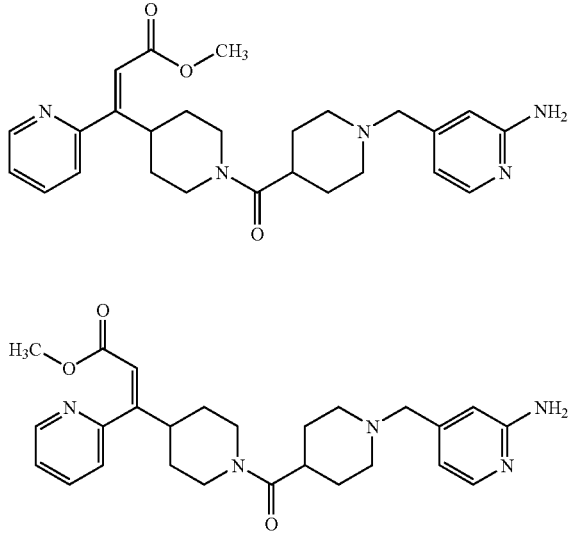

Step 1:

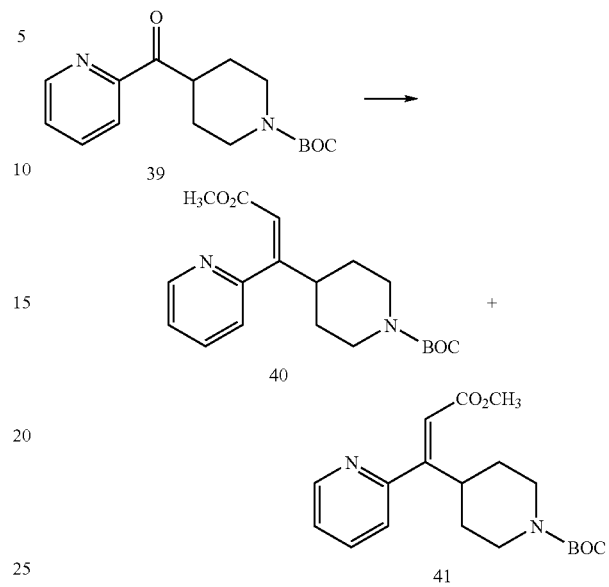

Ketone 39 was prepared as described in WO2002032893. The ketone was converted to the carboxylates as described in Example 22.

Step 2: The amines 40 and 41 were deprotected and coupled with carboxylic acid lithium salt 2c in a manner similar to that described in Example 2 to obtain the title compounds. MS (M+H): 464.

EXAMPLE 24

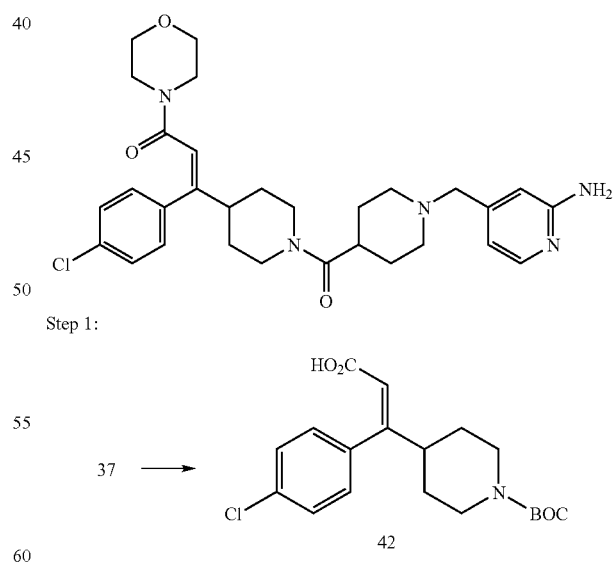

Step 1:

37 →

To a solution of compound 37 (530 mg, 1.40 mmol) dissolved in 30 ml of 1:1 methanol:water was added LiOH (117 mg, 2.79 mmol). The reaction mixture was heated at reflux for 16 h. The solvent was evaporated to give 553 mg (1.40 mmol, 100%) of the product 42 (with one equivalent of LiOH) as a white solid.

Step 2:

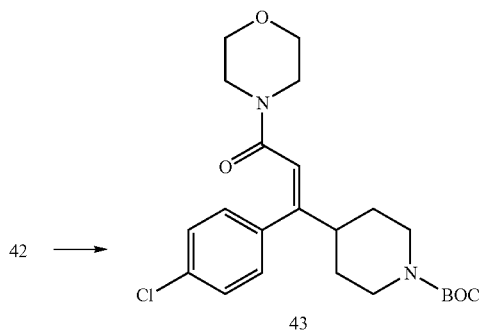

To a solution of compound 42 (500 mg, 1.35 mmol) dissolved in 20 ml of 1:1 DMF:CH$_2$Cl$_2$ was added morpholine (0.152 ml, 1.74 mmol), HOBT (275 mg, 2.03 mmol), and EDCl—HCl (390 mg, 2.03 mmol). The reaction mixture was stirred at rt for 16 h. The solvent was evaporated, 0.5 N NaOH was added, and the product was extracted with CH$_2$Cl$_2$. The combined organic extract was dried (MgSO$_4$), filtered, and concentrated. Purification by silica gel chromatography (eluant: 2%-5% MeOH —CH$_2$Cl$_2$) gave 184 mg (0.423 mmol, 31%) of the product 43.

Step 3:

The amine 43 was deprotected and coupled with carboxylic acid lithium salt 2c in a manner similar to that described in Example 2 to obtain the title compound. MS (M+H): 552.

EXAMPLE 25

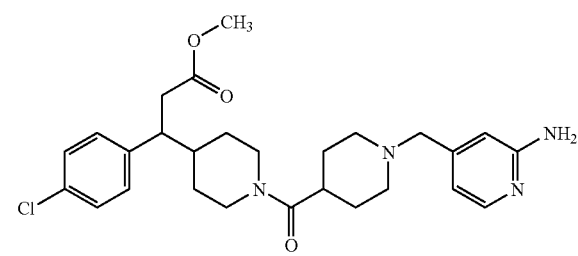

Step 1:

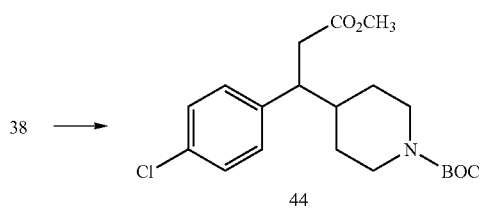

To a solution of compound 38 (5.70 g, 15.0 mmol) dissolved in MeOH (50 ml) was added 0.40 g of PtO$_2$ catalyst. The reaction mixture was shaken on the Parr apparatus at 50 psi of hydrogen pressure for 16 h. The catalyst was removed by filtration and washed with MeOH. The filtrate was concentrated, and purification by silica gel chromatography (eluant: 10% EtOAc-hexane) gave 1.40 g (3.67 mmol, 24%) of the product 44 as a colorless oil.

Step 2: The amine 44 was deprotected and coupled with carboxylic acid lithium salt 2c in a manner similar to that described in Example 2 to obtain the title compound.

MS (M+H): 499.

EXAMPLE 26

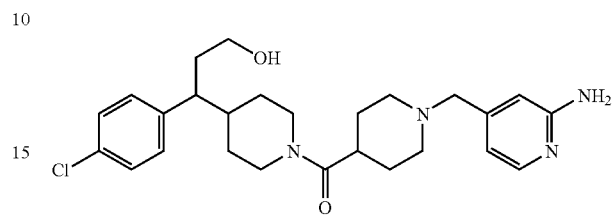

Step 1:

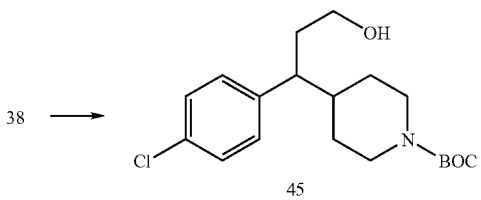

Compound 45 was prepared using the procedure of Example 17 for preparing compound 30.

Step 2: The amine 45 was deprotected and coupled with carboxylic acid lithium salt 2c in a manner similar to that described in Example 2 to obtain the title compound.

MS (M+H): 471.

EXAMPLE 27

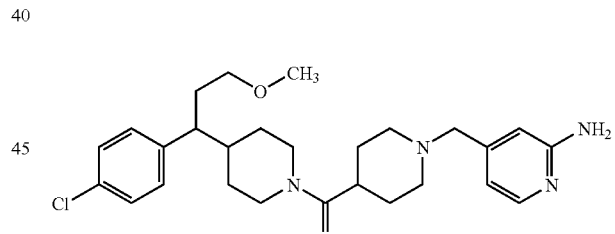

Step 1:

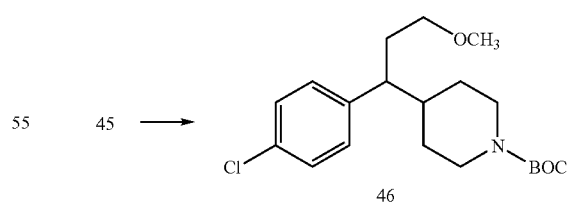

Compound 46 was prepared using the procedure of Example 14 for preparing compound 25.

Step 2: The amine 46 was deprotected and coupled with carboxylic acid lithium salt 2c in a manner similar to that described in Example 2 to obtain the title compound.

MS (M+H): 485.

EXAMPLE 28

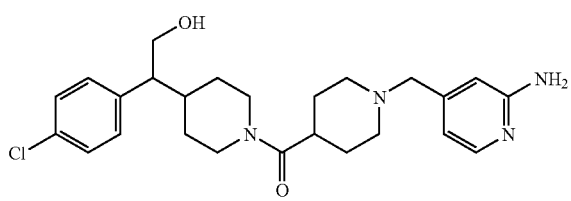

Step 1:

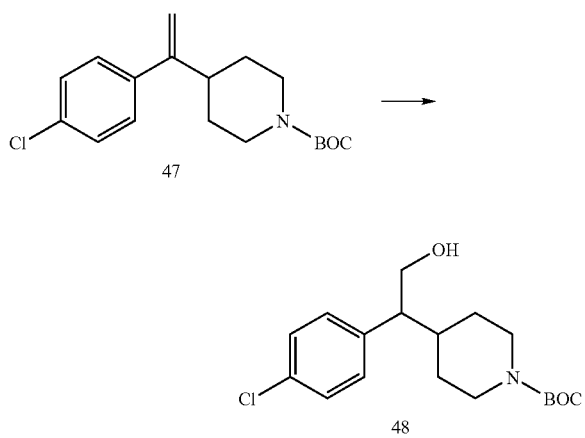

To compound 47 (4.82 g, 15.0 mmol) [prepared using procedure described in Example 5 for the synthesis of compound 14] was added 9-BBN (0.5 M in THF, 90 ml, 44.9 mmol). The reaction mixture was heated at reflux for 2 h then cooled to 0° C. EtOH (25 ml) was added carefully, and the resulting solution was stirred at rt for 60 min then recooled to 0° C. H$_2$O$_2$ (30%, 50 ml) was added carefully, and the resulting solution was stirred at rt for 16 h. The solvent was evaporated, water (100 ml) was added, and the product was extracted with CH$_2$Cl$_2$. The combined organic extract was dried (MgSO$_4$), filtered, and concentrated. Purification by silica gel chromatography (eluant: 2%-7% MeOH—CH$_2$Cl$_2$) gave 5.09 g (15.0 mmol, 100%) of the product 48 as a colorless oil.

Step 2: The amine 48 was deprotected and coupled with carboxylic acid lithium salt 2c in a manner similar to that described in Example 2 to obtain the title compound.

MS (M+H): 457.

EXAMPLE 29

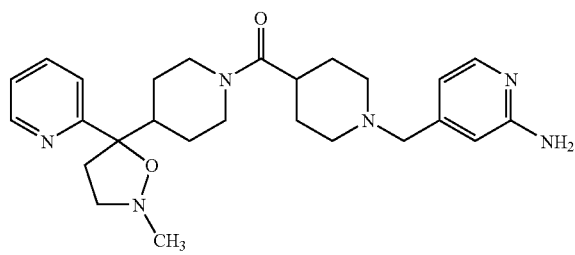

-continued

Step 1:

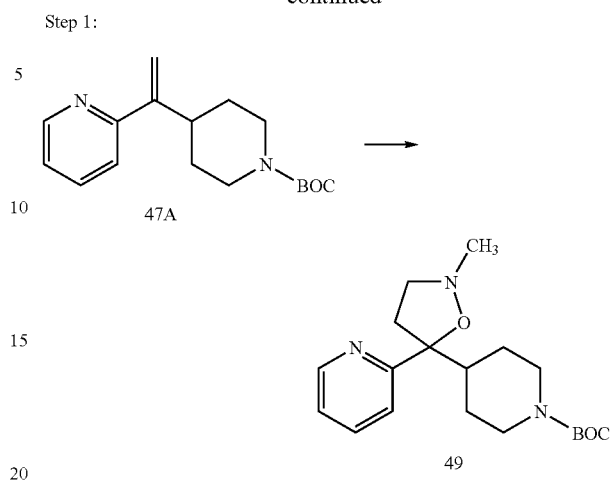

To a solution of compound 47A (1.85 g, 6.42 mmol) dissolved in EtOH (30 ml) was added N-methylhydroxylamine hydrochloride (1.18 g, 14.1 mmol), formaldehyde (0.42 g, 14.1 mmol), and Et$_3$N (1.40 g, 1.9 ml, 13.8 mmol). The reaction mixture was heated at reflux for 16 h. The solvent was evaporated, 1 N NaOH (50 ml) was added, and the product was extracted with CH$_2$Cl$_2$. The combined organic extract was dried (MgSO$_4$), filtered, and concentrated. Purification by silica gel chromatography (eluant: EtOAc) gave 1.80 g (5.18 mmol, 81%) of the product 49 as a yellow oil.

Step 2: The amine 49 was deprotected and coupled with carboxylic acid lithium salt 2c in a manner similar to that described in Example 2 to obtain the title compound.

MS (M+H): 465.

EXAMPLE 30

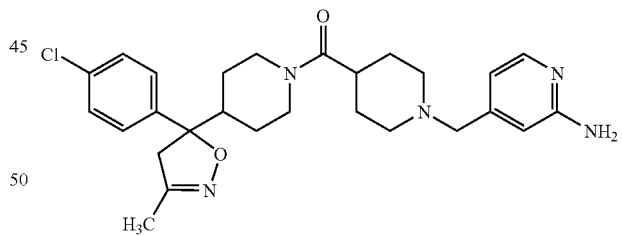

Step 1:

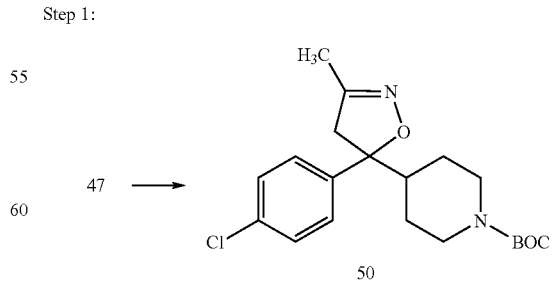

A solution of nitroethane (0.3 ml, 4.2 mmol) and Et$_3$N (0.66 ml, 4.7 mmol) in toluene (2 ml) was added to a solution of olefin 47 (0.51 g, 1.6 mmol) and phenylisocyanate (0.6 ml, 3.31 mmol) in toluene (8 ml) at 85° C. via a syringe at 0.01 ml/min. The resulting mixture was refluxed overnight, cooled to rt, then 1 N aqueous NH₄Cl (10 ml) was added and the mixture stirred for 1 h. The aqueous layer was separated and extracted with Et₂O. The organic extracts were combined, dried (MgSO₄), filtered and concentrated. The residue was purified by column chromatography (eluted with EtOAc/hexanes, 1:3) to give desired adduct 50 (0.47 g, 78%) as a yellow foam.

Step 2: The amine 50 was deprotected and coupled with carboxylic acid lithium salt 2c in a manner similar to that described in Example 2 to obtain the title compound.

MS (M+H): 496.

EXAMPLE 31

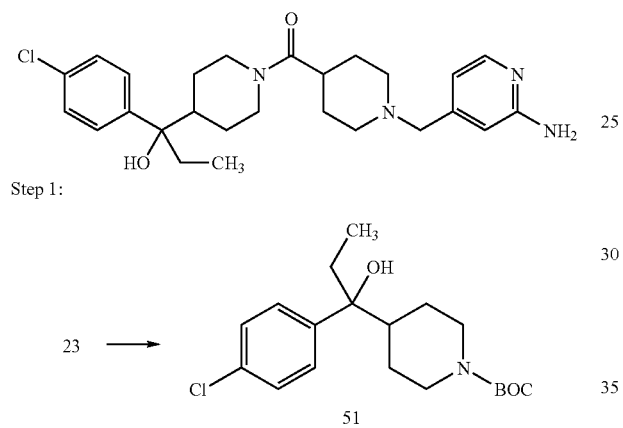

Step 1:

To a solution of compound 23 (3.54 g, 10.9 mmol) dissolved in dry THF (30 ml) and cooled to 0° C., was added ethylmagnesium chloride (2.0 M in THF, 11 ml, 21.9 mmol) dropwise via syringe. The reaction mixture was heated at reflux for 3 h. The solvent was evaporated, saturated NH₄Cl was added, and the product was extracted with EtOAc. The combined organic extract was dried (MgSO₄), filtered, and concentrated. Purification by silica gel chromatography (eluant: 10%-20% EtOAc-hexane) gave 2.34 g (6.62 mmol, 60%) of the product 51 as a white foam.

Step 2: The amine 51 was deprotected and coupled with carboxylic acid lithium salt 2c in a manner similar to that described in Example 2 to obtain the title compound.

MS (M+H): 471.

EXAMPLE 32 AND 32A

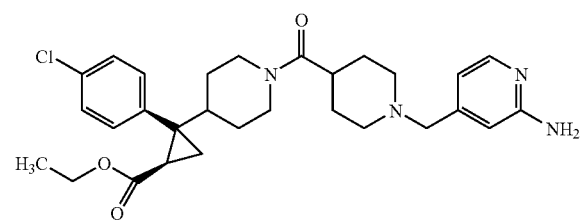

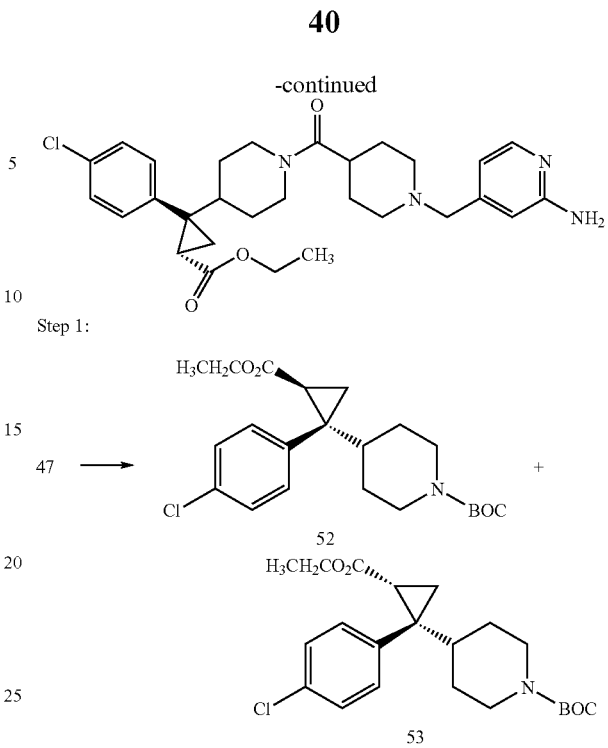

Step 1:

A solution of ethyl diazoacetate in DCM (0.45 M, 150 ml, 67.5 mmol) was added to a slurry of olefin 44 (13.0 g, 40.2 mmol), and Rh₂(OAc)₄ (1.37 g, 3.10 mmol) in DCM (80 ml) via syringe at 1.5 ml/h. The resulting mixture was filtered through Celite, and the filtrate was concentrated in vacuo. The residue was purified by column chromatography (eluted with EtOAc/hexanes, 1:12) to give cis adduct 52 (3.63 g, 24%) as a white solid and trans adduct 53 (4.40 g, 25%) as a yellow foam.

Step 2: The amines 52 and 53 were deprotected and coupled with carboxylic acid lithium salt 2c in a manner similar to that described in Example 2 to obtain the title compounds. MS (M+H): 525.

EXAMPLE 33

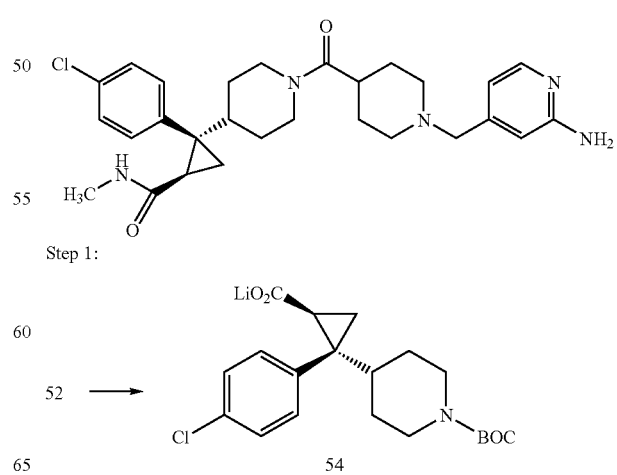

Step 1:

LiOH (0.48 g, 11.4 mmol) was added to a solution of ester 52 (2.32 g, 5.70 mmol) in MeOH—H₂O (v/v, 1:1; 24 ml). The mixture was heated at 80° C. overnight, cooled to rt, then MeOH was added and the mixture concentrated. The resulting light yellow solid was dried under high vacuum to give desired product 54 (2.38 g, 100%) as a white solid.

Step 2:

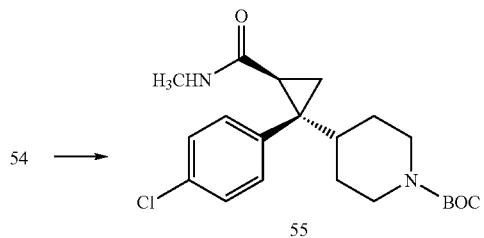

A mixture of lithium salt 54 (0.52 g, 1.3 mmol), EDCl (0.50 g, 2.6 mmol), HOBt (0.39 g, 2.9 mmol) and a of solution 2N MeNH₂ in THF (2 ml, 4.0 mmol) were mixed in DMF (10 ml). The mixture was stirred at rt overnight. The mixture was diluted with DCM and washed with 0.3 N NaOH, the aqueous layer was separated and extracted with DCM. The combined organic layer was washed with brine, dried (MgSO₄), filtered and concentrated in vacuo. The residue was purified by column chromatography (eluted with EtOAc/hexanes, 1:1) to give desired product 55 (0.35 g, 63%) as a white solid.

Step 3:

The amine 55 was deprotected and coupled with carboxylic acid lithium salt 2c in a manner similar to that described in Example 2 to obtain the title compound. MS (M+H): 510.

EXAMPLE 34

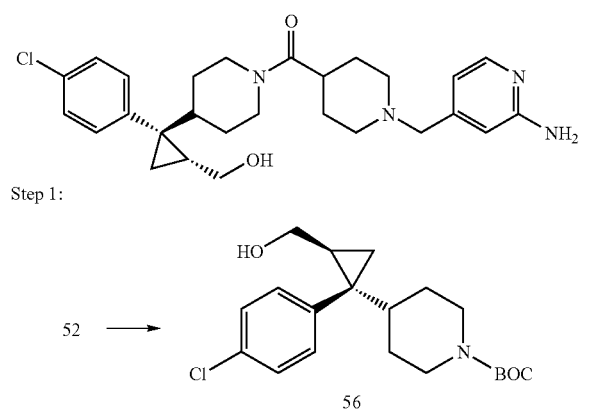

A solution of ester 52 (1.19 g, 2.92 mmol) in THF (30 ml) was cooled to −78° C. DIBAL (1.0 M in DCM, 10 ml) was added. The resulting solution was stirred at −78° C. to 0° C. for 1.5 h. MeOH (2 ml) was added, followed by 10% sodium potassium tartrate solution (30 ml). The cold bath was removed and the mixture was stirred at rt overnight and filtered through Celite. The aqueous layer was separated and extracted with DCM. The organic extracts were combined, dried (MgSO₄) and concentrated in vacuo. The residue was purified by column chromatography (eluted with EtOAc/hexanes, 1:1) to give desired alcohol 56 (0.58 g, 54%) as a white solid.

Step 2: The amine 56 was deprotected and coupled with carboxylic acid lithium salt 2c in a manner similar to that described in Example 2 to obtain the title compound.
MS (M+H): 483.

EXAMPLE 35

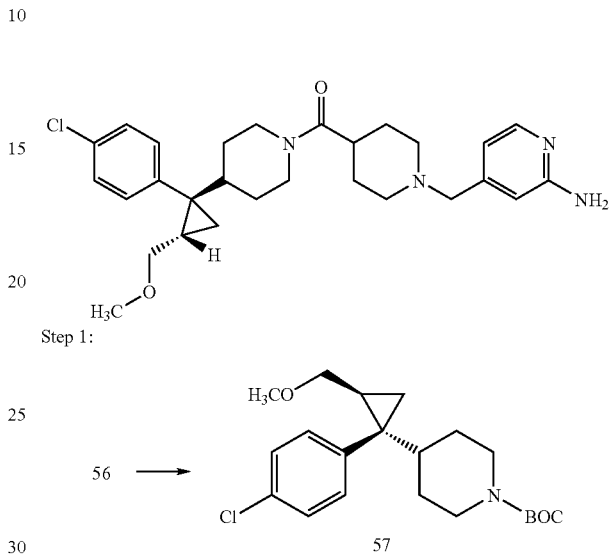

NaH (47 mg, 1.2 mmol) was added to a solution of starting alcohol 56 (0.30 g, 0.80 mmol) in DMF (8 ml) at 0° C. CH₃I (0.10 ml, 1.6 mmol) was added. The slurry was stirred at rt overnight. The mixture was concentrated and purified by column chromatography (eluted with EtOAc/hexanes, 1:3) to give desired ether 57 (0.22 g, 71%) as a colorless oil.

Step 2: The amine 57 was deprotected and coupled with carboxylic acid lithium salt 2c in a manner similar to that described in Example 2 to obtain the title compound.
MS (M+H): 497.

EXAMPLE 36

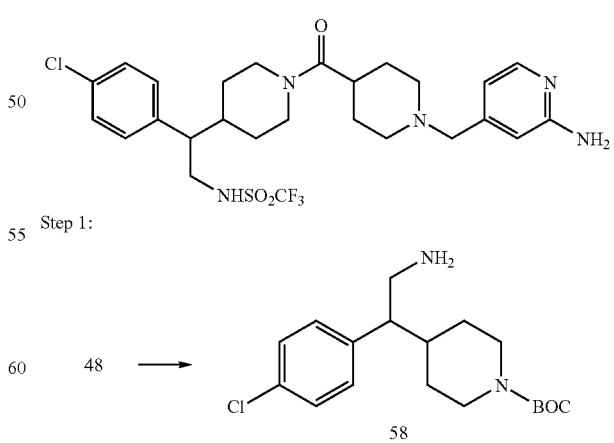

The alcohol 48 (2.08 g, 6.14 mmol) was dissolved in DCM (25 ml) and cooled with an ice-bath. Et₃N (2 ml, 14 mmol) and CH₃SO₂Cl (0.67 ml, 8.7 mmol) were added sequentially.

The mixture was stirred for 0.5 h, diluted with DCM and washed with 1 N HCl (25 ml). The aqueous layer was separated and extracted with DCM. The organic layers were combined, dried (MgSO₄), filtered and concentrated. The resulting solid was dissolved in DMF (25 ml), and NaN₃ (0.80 g, 12.3 mmol) was added. The slurry was heated at 80° C. overnight, cooled to rt and diluted with Et₂O (100 ml). The mixture was washed with water (4×25 ml) and the combined aqueous layer was extracted with Et₂O. The organic extracts were combined, dried (MgSO₄), filtered and concentrated. The residue was purified by column chromatography (eluted with EtOAc/hexanes, 1:5) to give desired azide (1.32 g, 59%) as a colorless oil.

The azide was dissolved in THF (25 ml)—H₂O (2.5 ml) and Ph₃P (2.03 g, 7.74 mmol) was added. The mixture heated at 70° C. overnight, cooled to rt, diluted with EtOAc and washed with brine. The organic layer was separated, dried (MgSO₄), filtered and concentrated. The residue was purified by column chromatography (eluted with MeOH/DCM, 1:10) to give desired amine 58 (0.91 g, 74%) as a yellow oil.

Step 2:

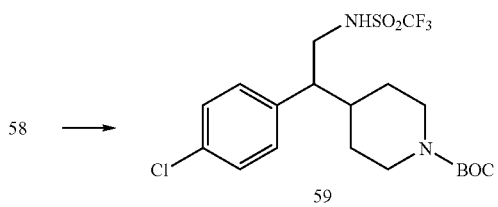

Amine 58 (0.55 g, 1.6 mmol) was dissolved in DCM (10 ml) and cooled to 0° C. Et₃N (0.45 ml, 3.6 mmol), and Tf₂O (0.38 ml, 2.3 mmol) were added sequentially and the mixture stirred from 0° C. to rt for 4 h. Water was added and extracted with DCM. The organic extracts were combined, dried (MgSO₄) and concentrated. The residue was purified by column chromatography (eluted with EtOAc/hexanes, 1:2) to give desired product 59 (0.47 g, 62%) as a yellow oil.

Step 3:

The amine 59 was deprotected and coupled with carboxylic acid lithium salt 2c in a manner similar to that described in Example 2 to obtain the title compound. MS (M+H): 588.

EXAMPLE 37

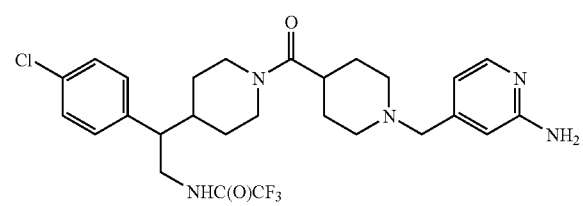

-continued

Step 1:

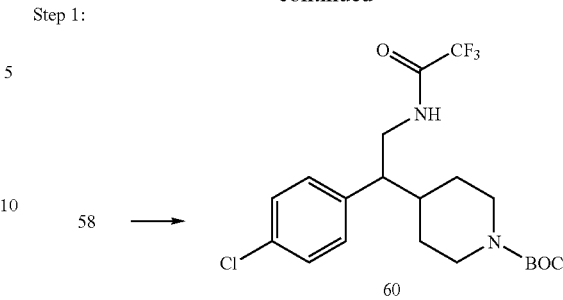

Amine 58 (0.51 g, 1.5 mmol) was dissolved in DCM (10 ml) and cooled to 0° C. Et₃N (0.52 ml, 3.7 mmol), TFAA (0.32 ml, 2.3 mmol) and DMAP (48 mg, 0.39 mmol) were added and stirred at rt for 4 h. Water was added and extracted with DCM. The organic extracts were combined, dried (MgSO₄) and concentrated. The residue was purified by column chromatography (eluted with EtOAc/hexanes, 1:2) to give desired product 60 (0.50 g, 76%) as a white foam.

Step 2: The amine 60 was deprotected and coupled with carboxylic acid lithium salt 2c in a manner similar to that described in Example 2 to obtain the title compound.
MS (M+H): 552.

EXAMPLE 38

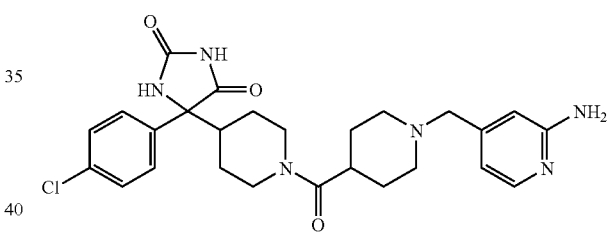

Step 1:

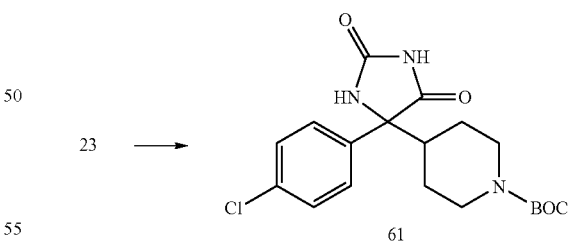

To a solution of 23 (1.0 g, 3.1 mmol) in 10 ml of EtOAc and H₂O (1:1) was added KCN (0.3 g, 4.6 mmol) and (NH₄)₂CO₃ (1.0 g, 10.8 mmol). After stirring at 100° C. for 20 h under N₂, the mixture was cooled to 25° C. Ice/H₂O was added to the mixture, and after stirring at 0° C. for 0.5 h, the products were extracted with EtOAc and H₂O, washed with brine, dried over Na₂SO₄, filtered. The filtrate was concentrated under vacuum and purified by flash chromatography to give 671 mg (55%) of 61.

Step 2: The amine 61 was deprotected and coupled with carboxylic acid lithium salt 2c in a manner similar to that described in Example 2 to obtain the title compound.

MS (M+H): 511.

EXAMPLE 39

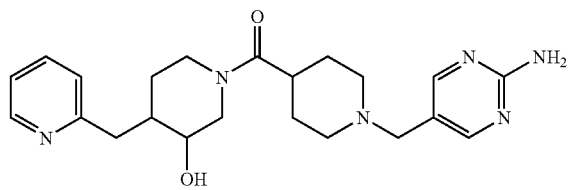

Step 1:

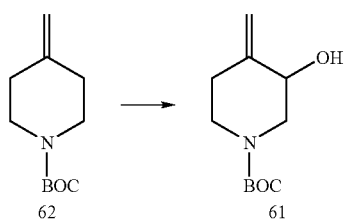

To a suspension of SeO$_2$ (2.8 g, 25.3 mmol) in CH$_2$Cl$_2$ (150 ml) was added t-butyl peroxide (14 ml, 10.1 mmol) at 0° C. After stirring at 0° C. for 15 min, 62 (10.0 g, 50.6 mmol) in 20 CH$_2$Cl$_2$ (20 ml) was added dropwise. The mixture was stirred at 0° C. under N$_2$ for 1 h, then at rt 20 h. The products were poured into 250 ml of 10% aqueous NaHSO$_4$ solution, extracted with CH$_2$Cl$_2$, washed with brine, dried over Na$_2$SO$_4$, and filtered. The filtrate was concentrated under vacuum and purified by flash chromatography to give 63 (4.8 g, 44%).

Step 2:

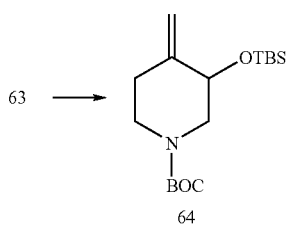

To a solution of 63 (4.8 g, 22.3 mmol) in CH$_2$Cl$_2$ (100 ml) was added TBSCI (4.0 g, 26.7 mmol), Et$_3$N (4.7 ml, 33.6 mmol), and DMAP (0.5 g, 4.5 mmol). After stirring at rt under N$_2$ for 20 h, NaOH (0.5N) aqueous solution was added, the mixture was extracted with CH$_2$Cl$_2$, washed with brine, dried over Na$_2$SO$_4$, and filtered. The filtrate was concentrated under vacuum and purified by flash chromatography to give 64 (5.6 g, 77%).

Step 3:

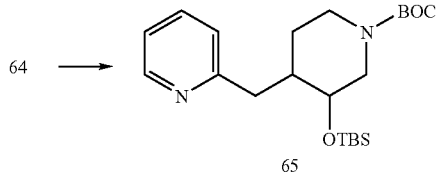

To 64 (4.5 g, 13.7 mmol) was added THF (9 ml) and 9-BBN (0.5M in THF, 41.2 ml, 20.6 mmol) under N$_2$ After stirring at 70° C. under N$_2$ for 3 h, the mixture was cooled to rt, Pd(dppf)Cl$_2$ (1.0 g, 1.2 mmol), 2-iodopyridine (3.4 g, 16.4 mmol), K$_2$CO$_3$ (2.8 g, 20.6 mmol), DMF (30 ml) and H$_2$O (3 ml) were added. After stirring at 80° C. under N$_2$ for 20 h, the mixture was concentrated under vacuum, and the products were poured into H$_2$O. NaOH (10%) aqueous solution was added to adjust the pH of the solution to 11. The mixture was extracted with EtOAc, washed with H$_2$O and brine, dried over Na$_2$SO$_4$, and filtered. The filtrate was concentrated under vacuum and purified by flash chromatography to give 65 (5.0 g, 90%).

Step 4:

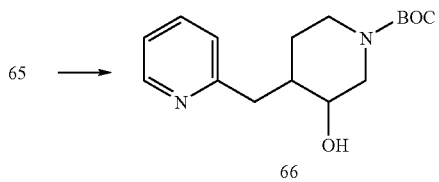

To a solution of 65 (5.0 g, 12.3 mmol) in THF (50 ml) was added tetra-n-butyl ammonium fluoride (1 M in THF, 18.4 ml, 18.4 mmol). After stirring at 50° C. for 20 h, the solvent was removed, the products were dissolved in CH$_2$Cl$_2$, washed with H$_2$O and brine, dried over Na$_2$SO$_4$, and filtered. The filtrate was concentrated under vacuum and purified by flash chromatography to give 66 (2.5 g, 70%).

Step 5:

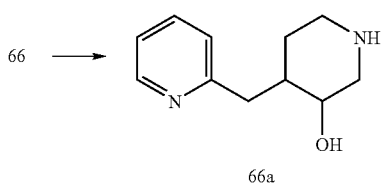

To a solution of 66 (0.7 g, 2.4 mmol) in 5 ml of CH$_2$Cl$_2$ was added 5 ml of TFA, After stirring at rt for 1.5 h, concentrated NH$_4$OH was added to the mixture. The products were extracted with CH$_2$Cl$_2$, washed with brine, dried over Na$_2$SO$_4$ and filtered. The filtrate was concentrated under vacuum to give 0.42 g of 66a.

Step 6:

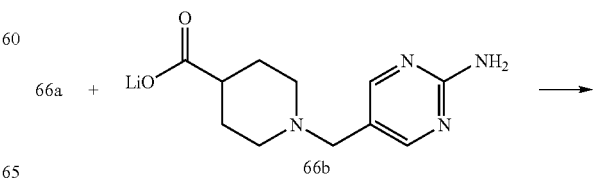

Ex. 39

To a solution of 66a (0.19 g, 1.0 mmol) and acid lithium salt. 66 (0.3 g, 1.2 mmol) in 10 ml of DMF was added n-ethylmorpholine (0.7 ml, 5.0 mmol) and 1-propanephosphonic acid cyclic anhydride (1.0 ml of 50 wt. % soln. in EtOAc, 1.7 mmol).; compound 66b was prepare from aldehyde 66c

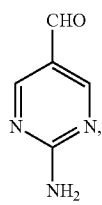

66c which is described in JP 63-227573, herein incorporated by reference, by using procedures analogous to those described in steps 4 and 5 of Example 1 in WO2002/032893

After stirring at 50° C. for 20 h under $N_2$, the solvent was removed under vacuum, the products were purified by flash chromatography (24% 2N $NH_3$ in MeOH/$CH_2Cl_2$) to give 0.12 g of Example 39. MS (M+H): 411.

EXAMPLE 40

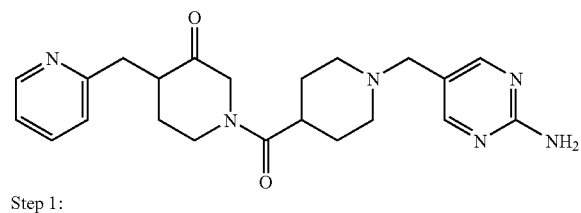

Step 1:

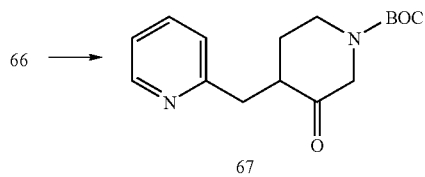

67

To a solution of oxayl chloride (0.6 ml, 7.3 mmol) in $CH_2Cl_2$ (30 ml) at −78° C. was added DMSO (1.0 ml, 14.5 mmol) in $CH_2Cl_2$ (5 ml). After stirring at −78° C. for 15 min, 66 (1.7 g, 5.8 mmol) in $CH_2Cl_2$ (10 ml) was added and the mixture was stirred at −78° C. for 2 h. $Et_3N$ in $CH_2Cl_2$ (2.4 ml in 5 ml) was added, and stirring was continued at −78° C. for another 0.5 h. The mixture slowly warmed up to rt, saturated $NaHCO_3$ aqueous solution was added, and the products were extracted with $CH_2Cl_2$, washed with brine, dried over $Na_2SO_4$, and filtered. The filtrate was concentrated under vacuum and purified by flash chromatography to give 67 (1.5 g, 89%).

Step 2: The amine 67 was deprotected and coupled with carboxylic acid lithium salt 2d in a manner similar to that described in Example 39 to obtain the title compound.
MS (M+H): 409.

EXAMPLE 41

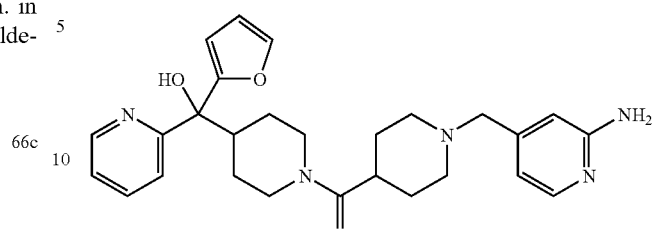

Step 1:

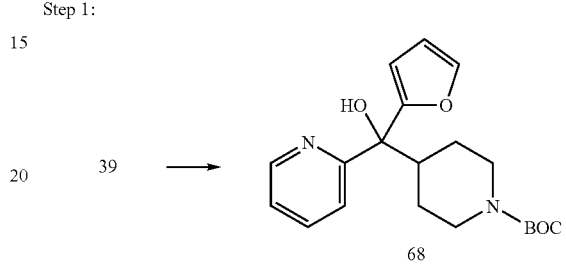

68

A solution of furan (0.30 g, 4.5 mmol) in $Et_2O$ (5 ml) was treated with nBuLi (2.8 ml, 1.6M/hexanes) while maintaining the temperature of −10° C. to −5° C. The reaction was stirred at 20° C. for 1 h, cooled to 0° C. and treated slowly with a solution of 39 (0.86 g, 3.0 mmol) in $Et_2O$ (10 ml). The mixture was then stirred overnight, quenched with sat'd aqueous $NH_4Cl$, and extracted with ether twice. The combined organic extracts were then concentrated to give 68 as an oily yellow solid (1.1 g).

Step 2: The amine 68 was deprotected and coupled with carboxylic acid lithium salt 2c in a manner similar to that described in Example 2 to obtain the title compound.
MS (M+H): 476.

EXAMPLE 42

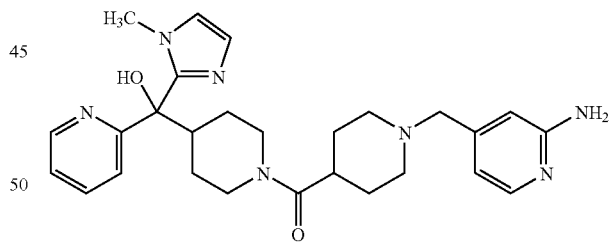

Step 1:

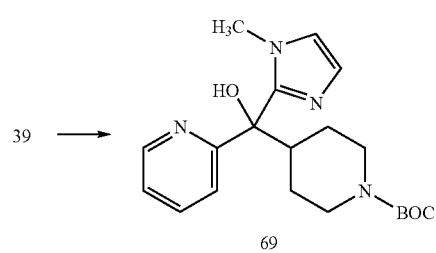

69

A solution of N-methylimidazole (0.73 ml, 9.2 mmol) in THF (5 ml) was treated with nBuLi (5.7 ml, 1.6M/hexanes) at −78° C., stirred for 1 h (−78° C.), and then treated slowly with a solution of 39 (1.8 g, 6.1 mmol) in THF (30 ml). The mixture was then stirred overnight, quenched with saturated aqueous NH₄Cl, extracted with CH₂Cl₂ twice, dried over MgSO₄, and concentrated. Chromatography (2-5% 1 N NH₃-MeOH/EtOAc) provided 69 as a white solid (2.13 g, 94%).

Step 2: The amine 69 was deprotected and coupled with carboxylic acid lithium salt 2c in a manner similar to that described in Example 2 to obtain the title compound.

MS (M+H): 490.

Step 3:

A solution of 71 (0.26 g, 0.5 mmol) in toluene (5 ml) was treated with azidotributyltin (0.28 ml, 1 mmol) and then heated at 110° C. for 3 days. The resulting solution was treated with 10% aqueous NaOH and stirred for 4 h. Following acidification with 3N HCl to pH 3, the aqueous layer was washed with hexanes (2×) and concentrated. The residue was taken up in MeOH and filtered to provide the title compound (0.058 g, 25%). MS (M+H): 462.

EXAMPLE 43

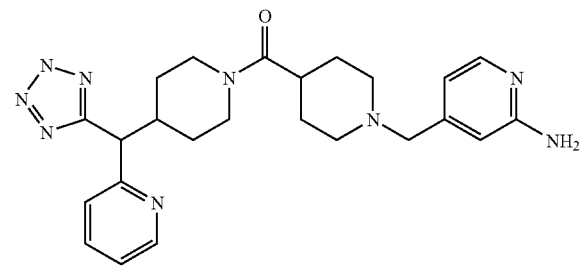

Step 1:

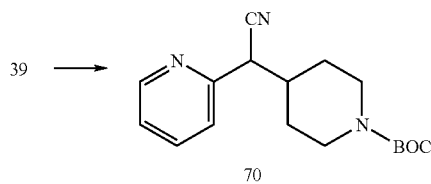

A solution of 39 (1.2 g, 4.1 mmol) in THF (10 ml) was treated with diethyl cyanophosphonate (2.1 ml, 12.4 mmol) and LiCN (24.7 ml, 0.5 M) and stirred for 3 h at 20° C. The reaction mixture was diluted with water, extracted with EtOAc, dried over MgSO₄, and concentrated. SmI₂ (165 ml, 0.1 M/THF) and tBuOH (0.59 ml, 6.2 mmol) were added and the mixture was stirred at 20° C. overnight. The reaction was quenched with 1 N HCl, neutralized with 10% NaOH, and extracted with CH₂Cl₂ (2×). The combined organic extracts were dried over MgSO₄, and concentrated. Chromatography (40-60% EtOAc/hexanes) provided 70 as a yellow oil (0.94 g, 76%).

Step 2:

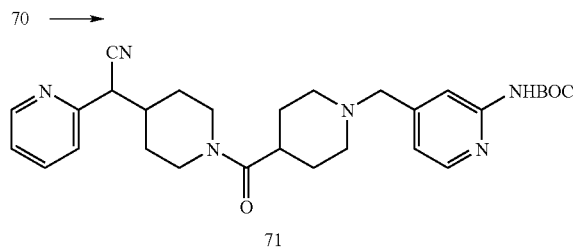

Compound 71 was prepared from compound 70 using the procedure of Example 2, Step 2.

EXAMPLE 44

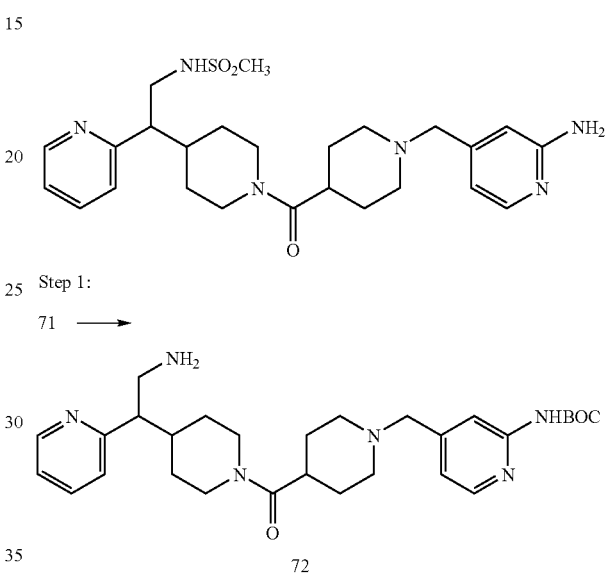

Step 1:

71 ⟶

A solution of 71 (0.54 g, 1.0 mmol) in NH₃-MeOH (1 M, 30 ml) was treated with Raney N₁ and H₂PtCl₆ and hydrogenated under 50 psi H₂ for 1 day. Chromatography (1 N NH₃-MeOH/EtOAc) provided 72 as a white solid (0.38 g, 70%).

Step 2:

72 ⟶

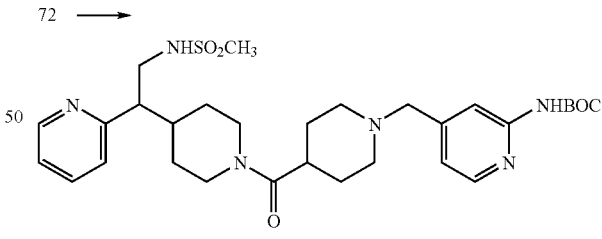

A suspension of 72 (0.37 g, 0.7 mmol) in CH₂Cl₂ (5 ml) was cooled to 0° C., treated with CH₃SO₂Cl (0.07 ml, 0.85 mmol) and Et₃N (0.2 ml, 1.4 mmol) and stirred overnight at 20° C. The resulting yellow suspension was diluted with CH₂Cl₂, washed with 10% aqueous NaOH, dried over MgSO₄, and concentrated. Chromatography (10% 1 N NH₃-MeOH/EtOAc) provided 73 as a white solid (0.25 g, 59%).

Step 3:

Compound 73 was deprotected to obtain the title compound. MS (M+H): 501.

EXAMPLE 45

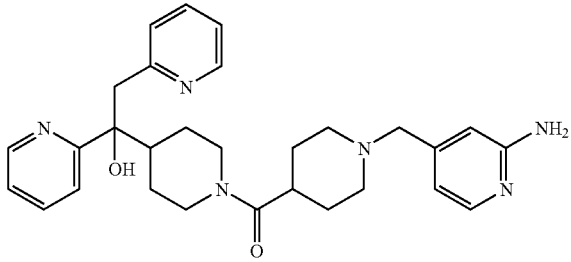

Step 1:

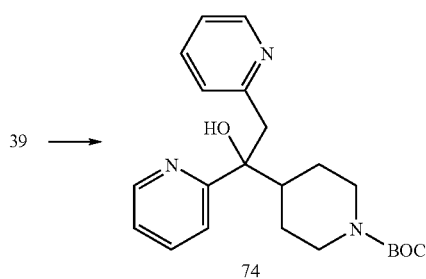

To a −20° C. solution of 2-picoline (0.687 g, 7.38 mmol) in anhydrous THF (5 ml) was slowly added BuLi (5.54 ml of 1.6M soln. in hexanes, 8.86 mmol), resulting in a dark orange solution. The reaction mixture was allowed to stir for 105 min at −20° C. The chilled reaction mixture was cannulated over a period of 2 h into a −40° C. solution of 39 (1.79 g, 6.2 mmol) in anhydrous THF (10 ml). The reaction mixture was allowed to stir for 2 h at −40° C., then was allowed to warm to rt. Saturated aqueous $NH_4Cl$ (20 ml), was added and the mixture was extracted with $CH_2Cl_2$ (2×40 ml). The organic layer was separated and dried over $Na_2SO_4$, followed by concentration and flash chromatography (0-20% acetone/$CH_2Cl_2$) to afford of 74 (0.968 g, 6.2 mmol; 41%) as a clear oil.

Step 2: The amine 74 was deprotected and coupled with carboxylic acid lithium salt 2c in a manner similar to that described in Example 2 to obtain the title compound.

MS (M+H): 501.

EXAMPLE 46

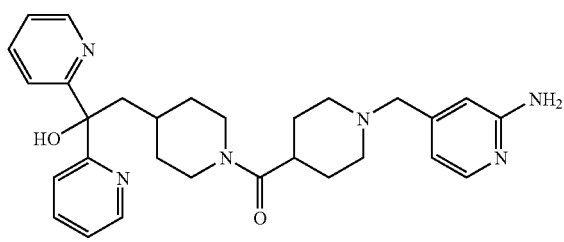

Step 1:

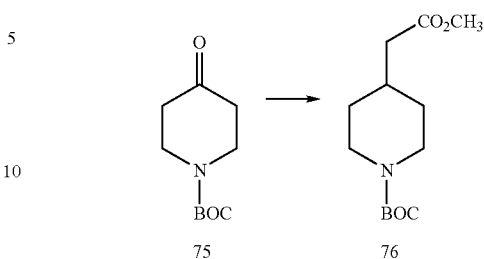

To a solution of KHMDS (10.3 g, 52 mmol) in anhydrous THF (30 ml) was added methyl diethyl phosphonoacetate (9.5 ml, 52 mmol). The reaction mixture was stirred for 1 h followed by the addition of 75 (8.58 g, 43 mmol). The reaction mixture was stirred overnight at 65° C. The mixture was quenched with saturated aqueous $NH_4Cl$, followed by extraction with $CH_2Cl_2$, concentration and flash chromatography (50-100% $CH_2Cl_2$/hexanes) to afford 6.01 g of the unsaturated ester as a white solid.

To a solution of unsaturated ester (6.01 g) in EtOH (100 ml) was added 10% Pd/C catalyst (500 mg). The reaction mixture was stirred at rt overnight under $H_2$ (1 atm). The filtrate was concentrated to yield 4.01 g of 76 as a clear oil.

Step 2:

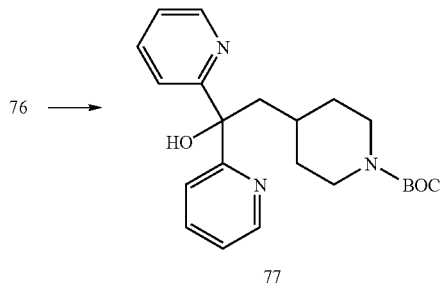

To a −78° C. solution of 2-bromopyridine (1.86 ml, 19.5 mmol) in anhydrous THF (30 ml) was slowly added 1.6 M BuLi soln. in hexanes (10.8 ml, 17.3 mmol), resulting in a dark orange solution. The reaction mixture was allowed to stir for 90 min. at −78° C. The cold reaction mixture was cannulated over a period of 2 h into a −78° C. solution of 76 (2.5 g (9.72 mmol) in anhydrous THF (20 ml). The reaction mixture was allowed to stir for 2.5 h at −78° C., then was allowed to reach rt. The reaction mixture was quenched with AcOH, followed by extraction with $CH_2Cl_2$ (3×70 ml). The organic layer was dried over $Na_2SO_4$, followed by concentration and flash chromatography (from 50% hexanes/$CH_2Cl_2$ to 10% acetone/$CH_2Cl_2$) to afford 0.41 g (2.83 g; 14%) of 77 as a yellow oil.

Step 3:

The amine 77 was deprotected and coupled with carboxylic acid lithium salt 2c in a manner similar to that described in Example 2 to obtain the title compound. MS (M+H): 501.

EXAMPLE 47

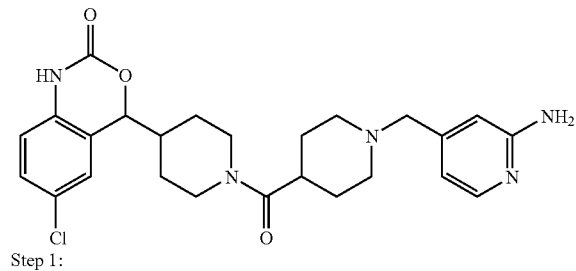

Step 1:

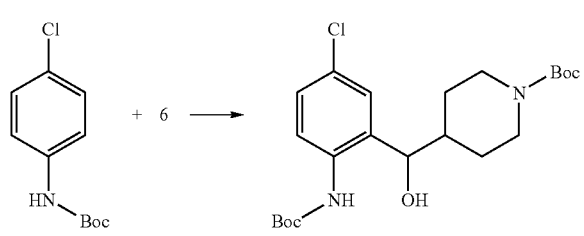

To a solution of compound 78 (1.00 g, 4.39 mmol) dissolved in dry THF (20 ml) and cooled to −50° C., was added sec-butyl lithium (1.3 M in cyclohexane, 7.1 ml, 9.22 mmol). The reaction mixture was stirred at 40° C. internal temperature for 60 min, then cooled to −78° C. Compound 6 (0.94 g, 4.39 mmol) dissolved in dry THF (5 ml) was added via syringe. The internal temperature was warmed to 40° C. and the mixture was stirred at −40° C. for 20 min. Glacial AcOH (0.75 ml) was added, and the resulting solution was warmed to rt. Saturated NH$_4$Cl (50 ml) was added, and the product was extracted with EtOAc. The combined organic extract was dried (MgSO$_4$), filtered, and concentrated. Purification by silica gel chromatography (eluant: 1%-2% MeOH—CH$_2$Cl$_2$) gave 1.35 g (3.06 mmol, 70%) of the product 79 as a yellow foam.

Step 2:

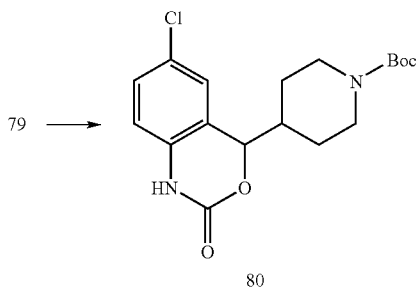

To a solution of compound 79 (1.34 g, 3.04 mmol) dissolved in toluene (20 ml) and cooled to 0° C. under N$_2$ was added n-butyl lithium (2.5 M in hexane, 1.28 ml, 3.19 mmol) dropwise via syringe. The reaction mixture was heated at reflux for 4 h. The solvent was evaporated. Purification by silica gel chromatography (eluant: 5% MeOH—CH$_2$Cl$_2$) gave 1.08 g (2.94 mmol, 97%) of the product 80 as a yellow foam.

The amine 80 was deprotected and coupled with carboxylic acid lithium salt 2c in a manner similar to that described in Example 2 to obtain the title compound. MS (M+H): 484.

EXAMPLE 48

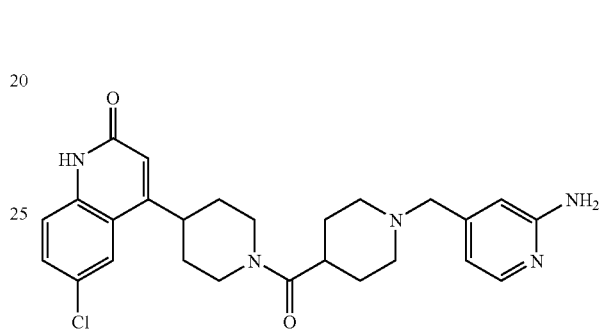

Step 1:

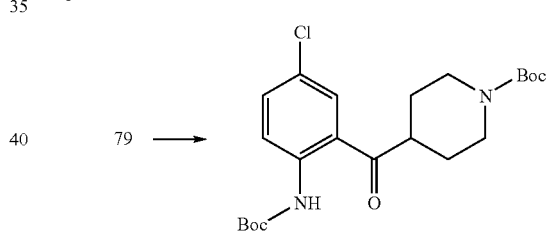

Compound 81 was prepared from compound 79 using the procedure of Example 5, Step 1.

The amine 81 was deprotected and coupled with carboxylic acid lithium salt 2c in a manner similar to that described in Example 47 to obtain the title compound. MS (M+H): 480.

Using procedures similar to those described above, the following compounds were prepared:

| Ex. | Structure | (M + H) |
|---|---|---|
| 47 | (structure shown) | 378 |

-continued
| Ex. | Structure | (M + H) |
|---|---|---|
| 48 | 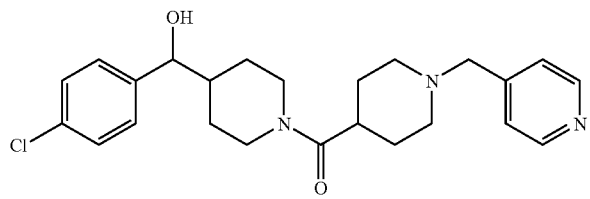 | 428 |
| 49 | 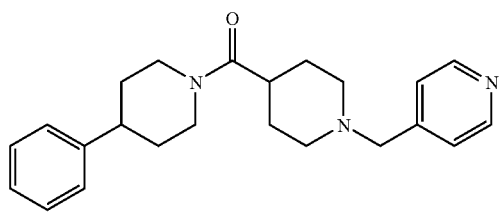 | 364 |
| 50 | 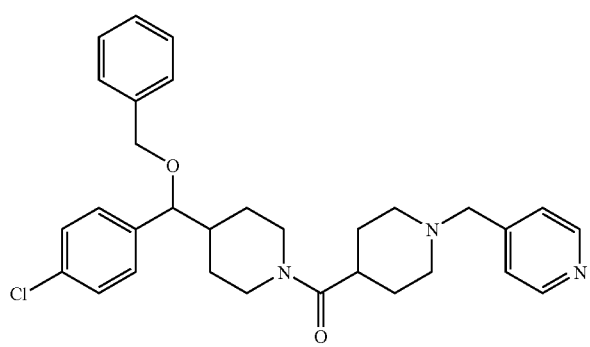 | 518 |
| 51 | 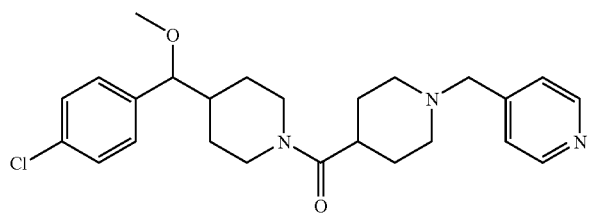 | 442 |
| 52 | 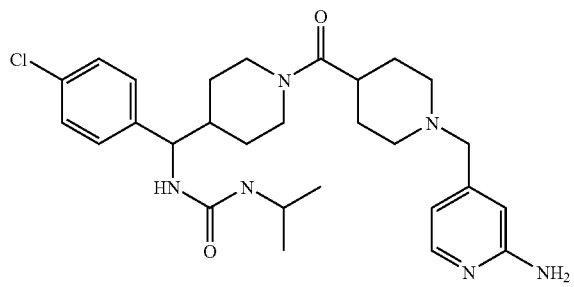 | 527 |
| 53 | 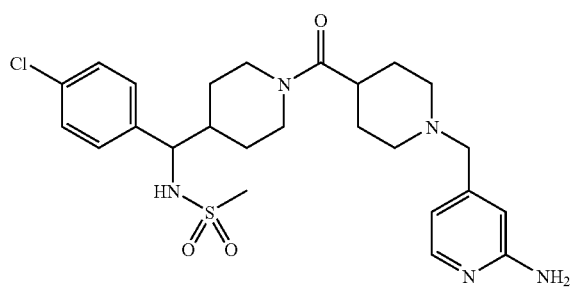 | 520 |

-continued

| Ex. | Structure | (M + H) |
|---|---|---|
| 54 | 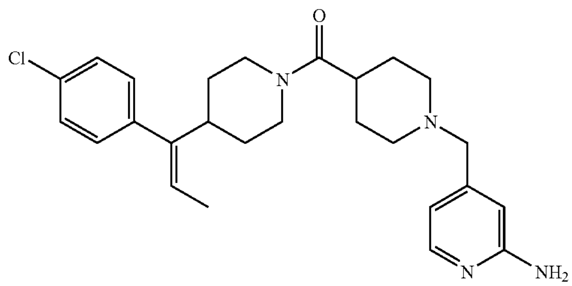 | 453 |
| 55 | 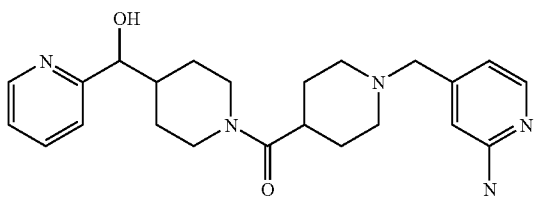 | 410 |
| 56 | 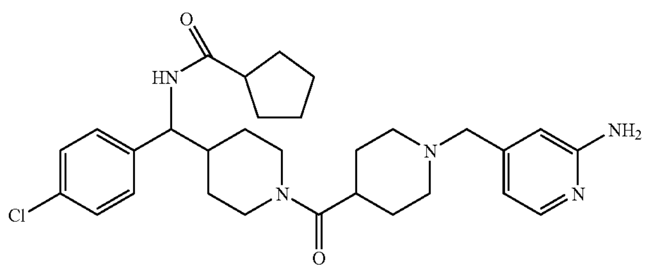 | 538 |
| 57 | 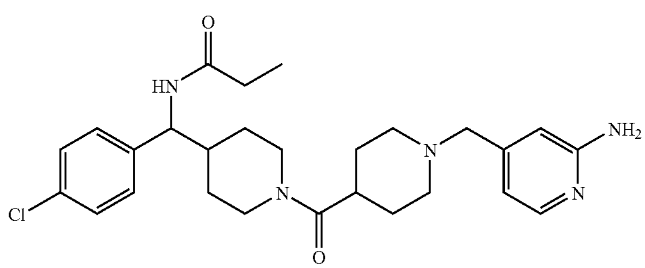 | 498 |
| 58 | 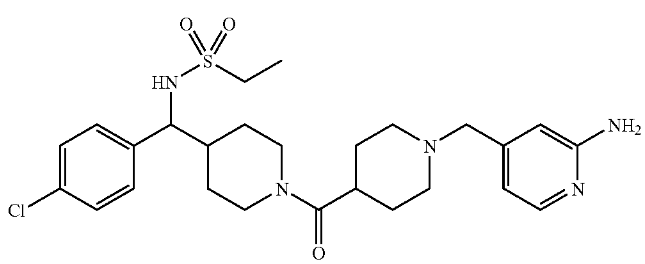 | 534 |
| 59 | 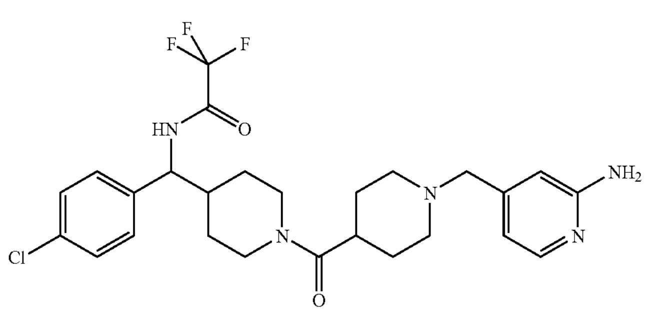 | 538 |

| Ex. | Structure | (M + H) |
|---|---|---|
| 60 | 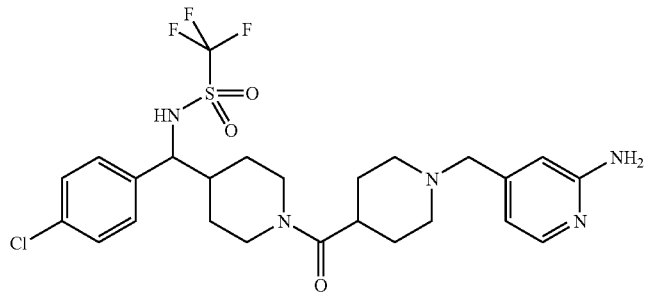 | 574 |
| 61 | 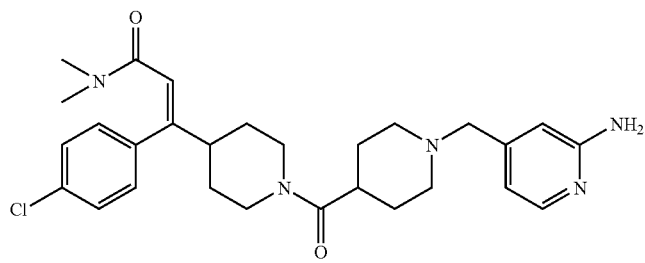 | 510 |
| 62 | 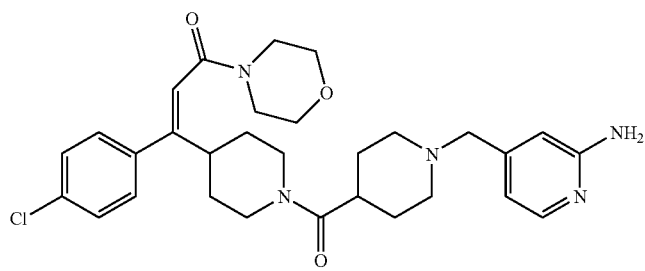 | 552 |
| 63 | 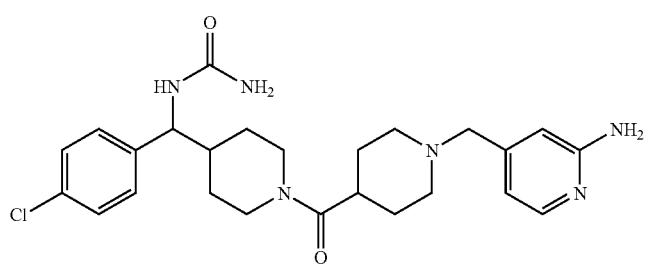 | 485 |
| 64 | 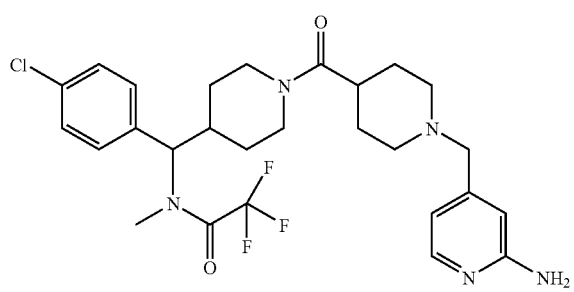 | 552 |

| Ex. | Structure | (M + H) |
|---|---|---|
| 65 | 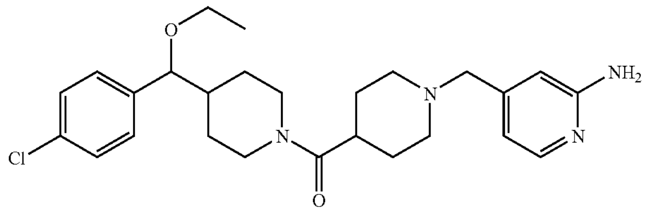 | 471 |
| 66 | 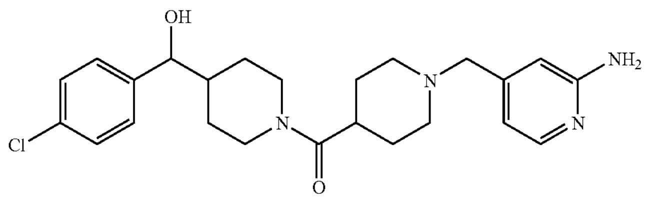 | 443 |
| 67 | 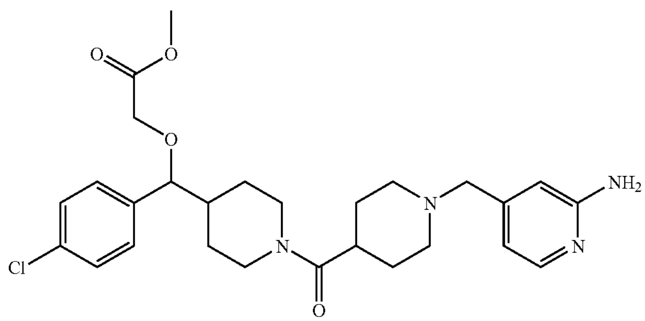 | 515 |
| 68 | 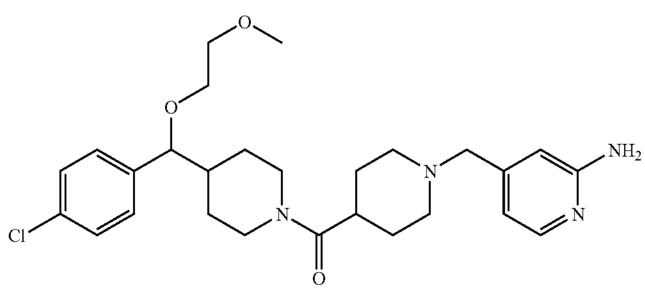 | 501 |
| 69 | 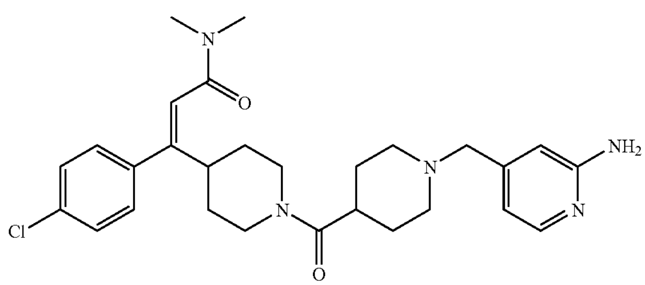 | 510 |
| 70 | 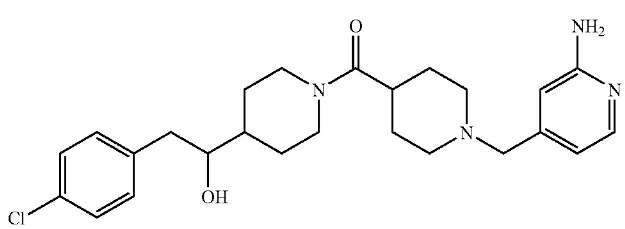 | 457 |

-continued
| Ex. | Structure | (M + H) |
|---|---|---|
| 71 | 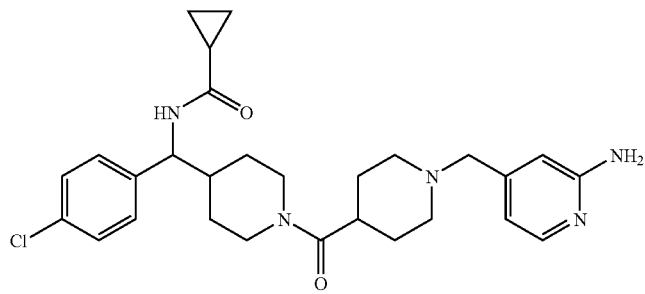 | 510 |
| 72 | 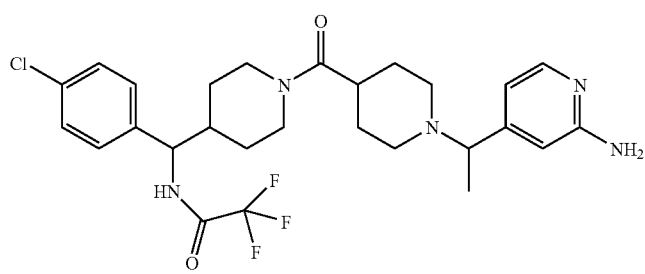 | 552 |
| 73 | 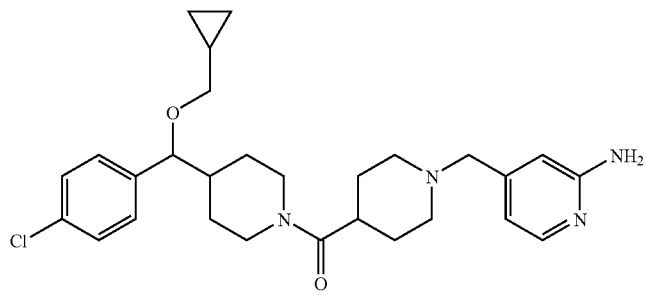 | 497 |
| 74 | 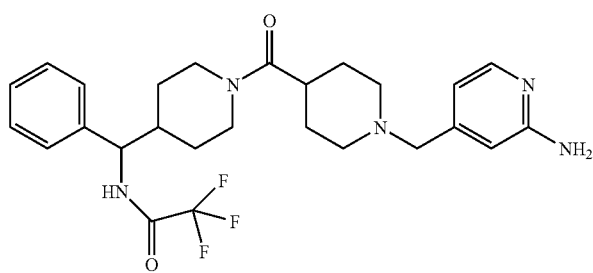 | 504 |
| 75 | 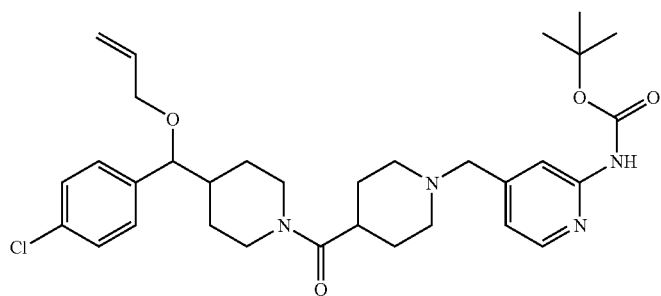 | 583 |

| Ex. | Structure | (M + H) |
|---|---|---|
| 76 | 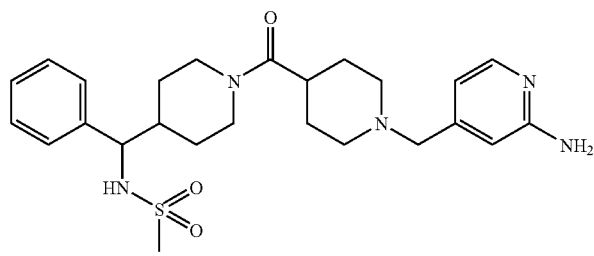 | 486 |
| 77 | 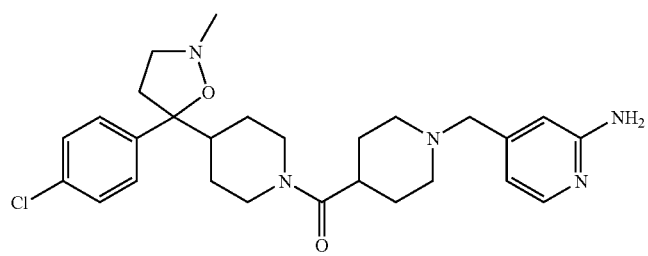 | 498 |
| 78 | 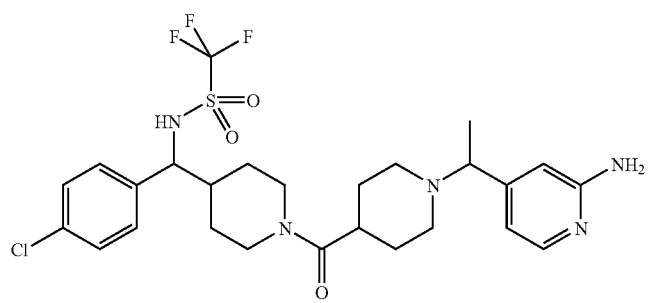 | 588 |
| 79 | 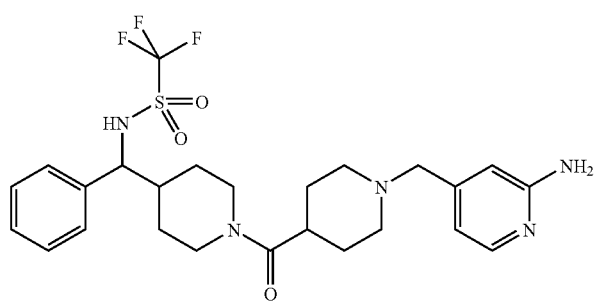 | 540 |
| 80 | 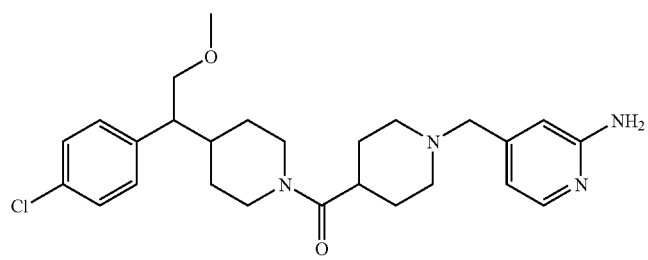 | 471 |

| Ex. | Structure | (M + H) |
|---|---|---|
| 81 | 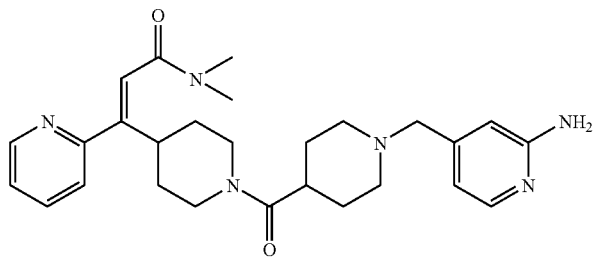 | 477 |
| 82 | 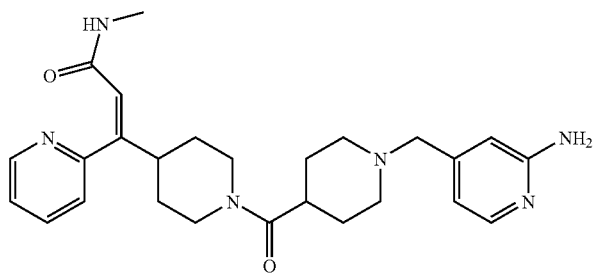 | 477 |
| 83 | 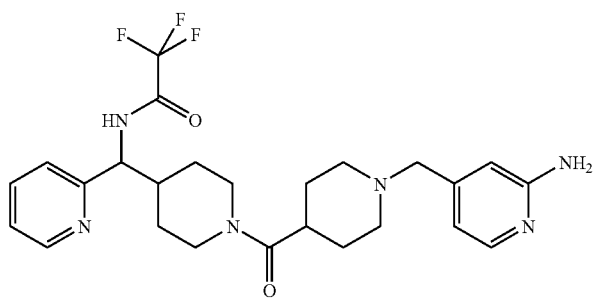 | 505 |
| 84 | 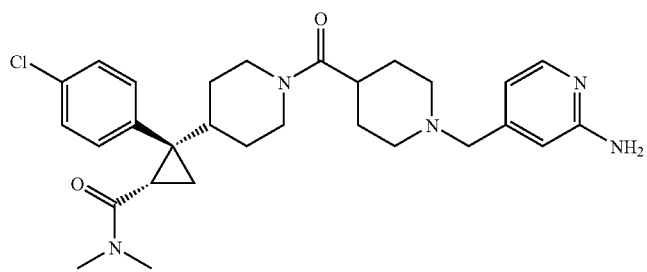 | 524 |
| 85 | 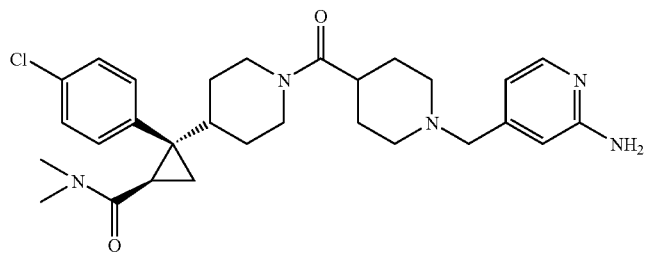 | 524 |

-continued

| Ex. | Structure | (M + H) |
|---|---|---|
| 86 | 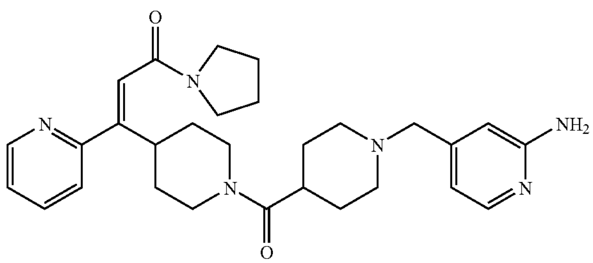 | 503 |
| 87 | 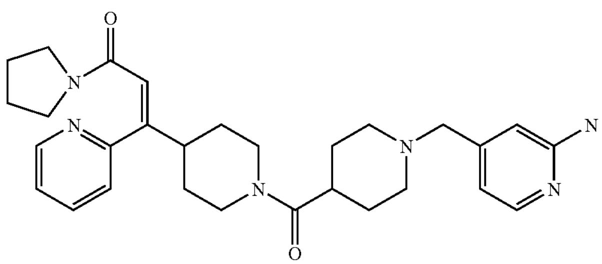 | 503 |
| 88 | 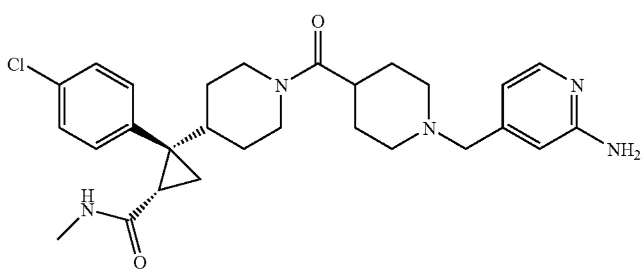 | 510 |
| 89 | 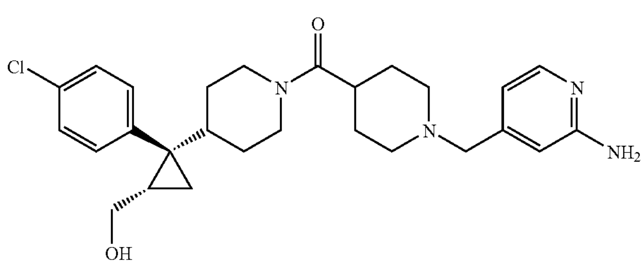 | 483 |
| 90 | 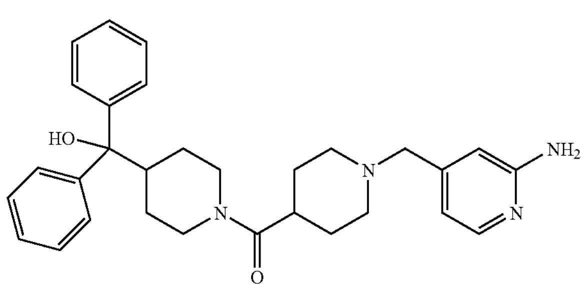 | 467 (M − OH) |
| 91 | 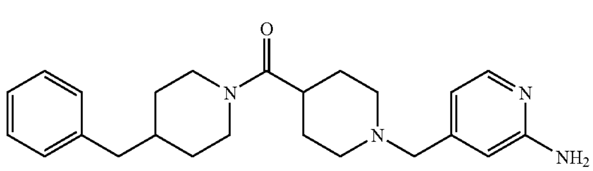 | 364 |

-continued

| Ex. | Structure | (M + H) |
|---|---|---|
| 92 | 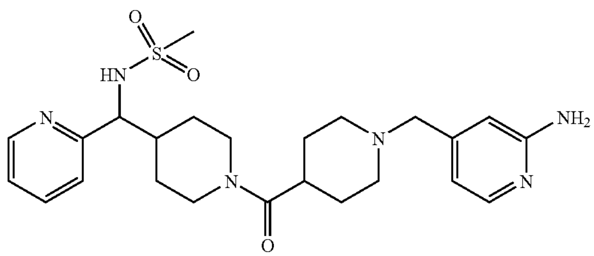 | 487 |
| 93 | 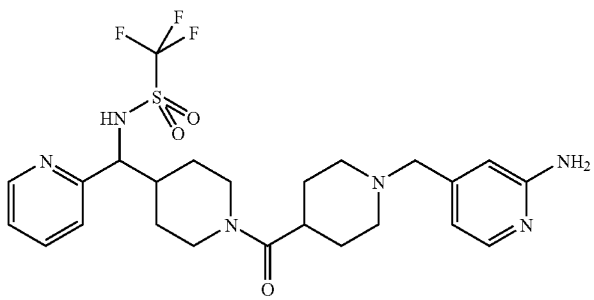 | 541 |
| 94 | 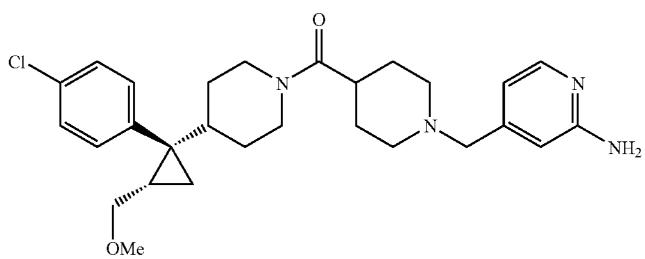 | 497 |
| 95 | 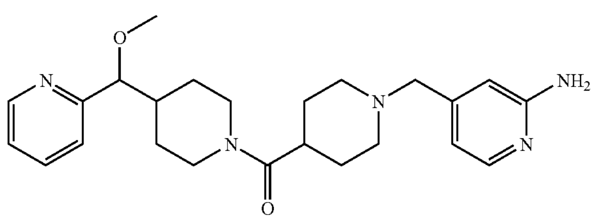 | 424 |
| 96 | 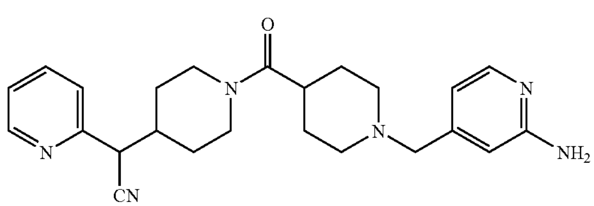 | 419 |
| 97 | 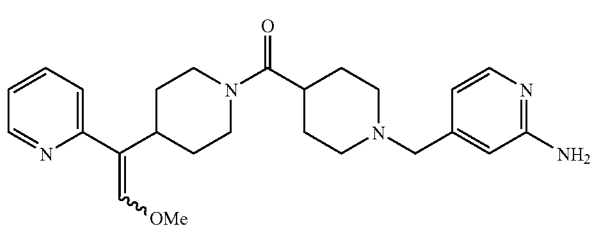 | 436 |

-continued

| Ex. | Structure | (M + H) |
|---|---|---|
| 98 | 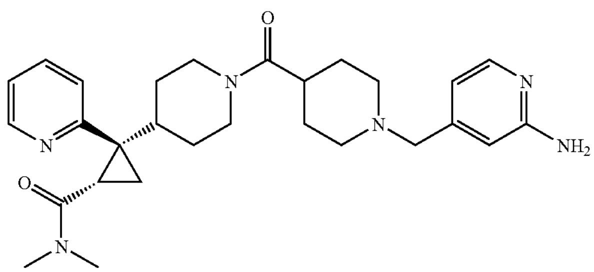 | 491 |
| 99 | 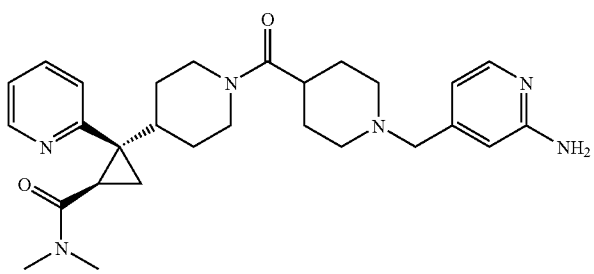 | 491 |
| 100 | 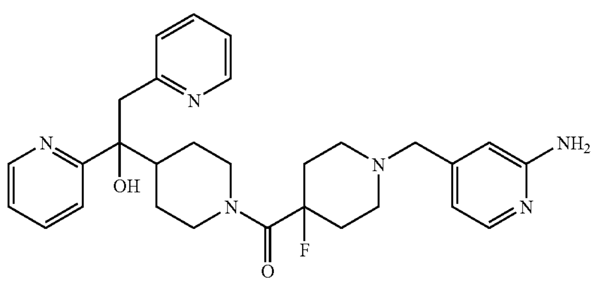 | 519 |
| 101 | 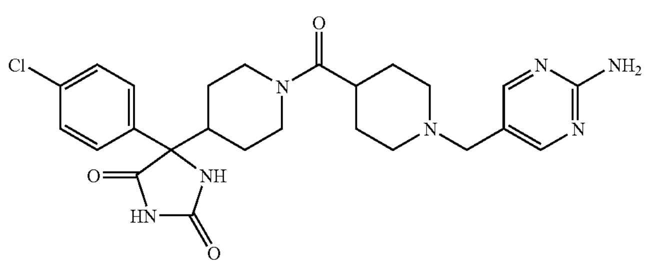 | 512 |
| 102 | 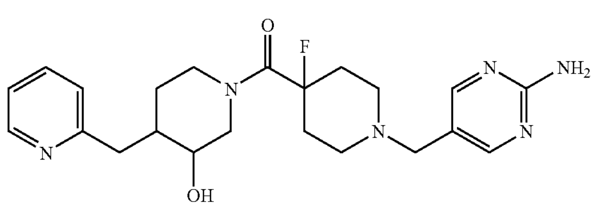 | 429 |
| 103 | 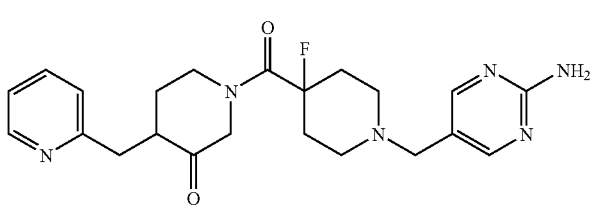 | 429 |

75

-continued

| Ex. | Structure | (M + H) |
|---|---|---|
| 104 | 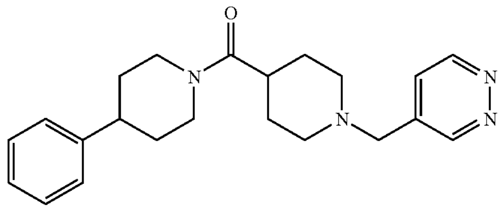 | 365 |
| 105 | 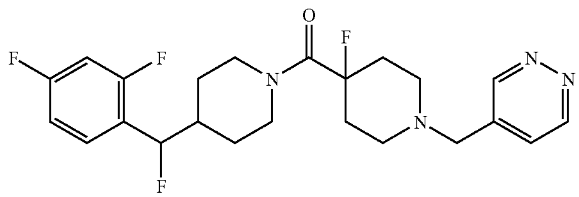 | 451 |
| 106 | 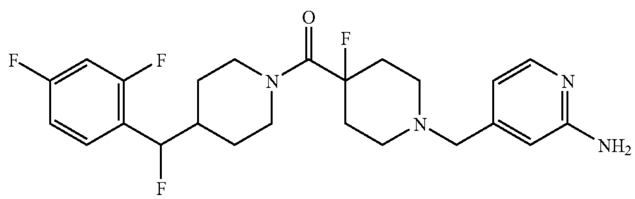 | 465 |
| 107 | 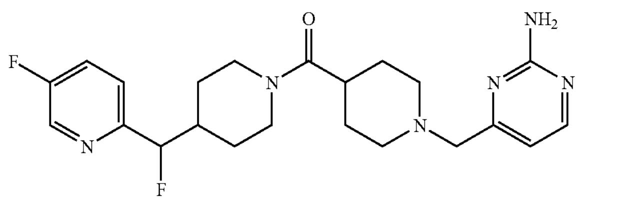 | 431 |
| 108 | 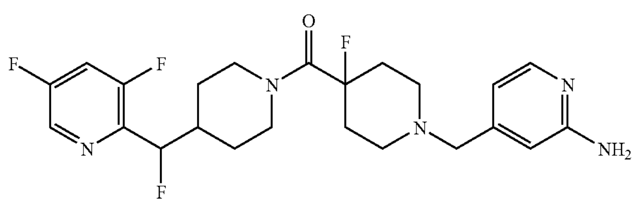 | 466 |

76

EXAMPLE 111

Step 1:

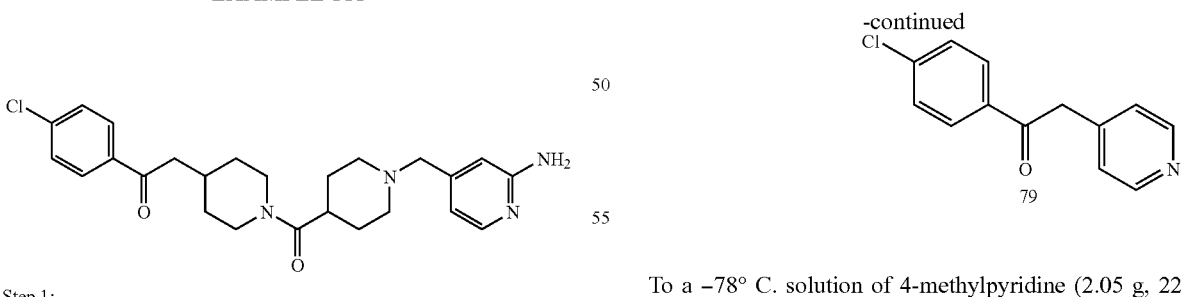

To a −78° C. solution of 4-methylpyridine (2.05 g, 22.0 mmol) in THF (50 ml) was added dropwise 2.5M BuLi solution in hexanes (9 ml, 22.5 mmol). The mixture was stirred at −78° C. for 30 min, then a solution of Weinreb amide 78 (4.00 g, 20.0 mmol) in THF (10 ml) was introduced. The mixture was allowed to warm to rt and was stirred overnight. The reaction mixture was quenched with aqueous NH$_4$Cl and extracted with ether. The organic phase was separated, dried over MgSO$_4$ and concentrated to a syrup, which crystallized upon standing. Crude material was recrystallized from isopropyl ether-hexanes to yield 2.5 g of ketone 79 as a yellow solid.

Step 2:

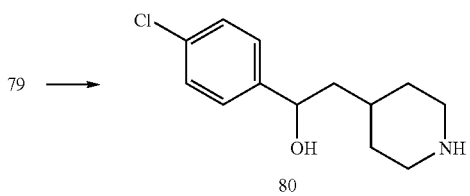

A solution of ketone 79 (2.4 g, 10.4 mmol) in AcOH (70 ml) was mixed with Pd/C catalyst (10%, 0.25 g), and the mixture was hydrogenated for 18 h at 30 psi. The catalyst was filtered off, the filtrate was concentrated, and the crude residue was treated with 7M HCl in isopropanol. Subsequent trituration with ethanol-ether provided 2.12 g of hydrochloride salt of 80 as a white solid, which was basified with 0.5M aqueous NaOH. Extraction with $CH_2Cl_2$, followed by concentration of the organic phase produced 1.5 g of alcohol 80 as an off-white solid.

Step 3:

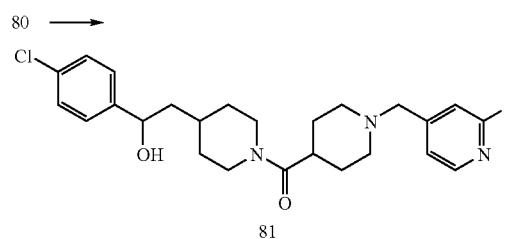

Compound 80 was converted into 81 using the procedure described in Example 1 for coupling the carboxylic acid lithium salt 2c with the amine 80.

Step 4:

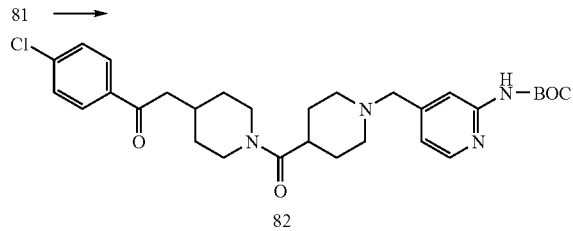

Compound 81 was converted into compound 82 using the procedure of Example 5, Step 1.

Step 5:

BOC-deprotection of 82 was carried out as described in Example 1, Step 2, to obtain the title compound. MS (M+H): 455.

EXAMPLE 112

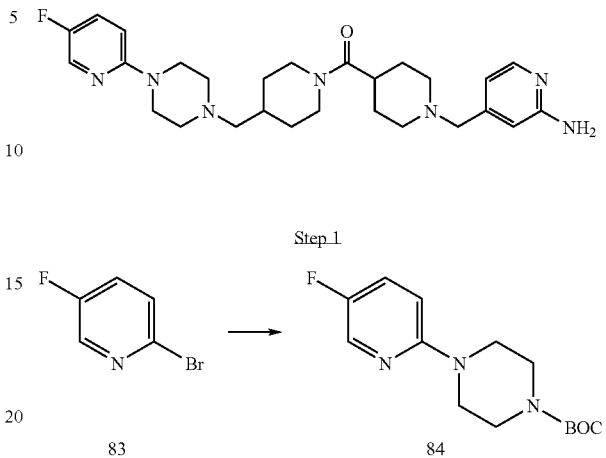

Step 1

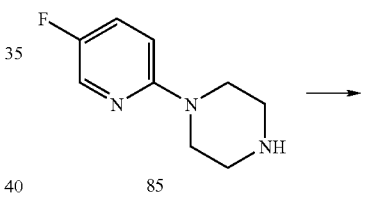

A mixture of bromopyridine 83 (1.5 g; 8.52 mmol), 1-BOC-piperazine (2.7 g; 14.5 mmol), $K_2CO_3$ (3.0 g; 21.7 mmol) in 5 mL of DMF was heated at 140° C. for 12 h. DMF was removed under vacuum. The residue was subjected to flash chromatography (20% ethyl acetate/hexanes) to produce 1.0 g of 84 as a yellow oil.

Step 2

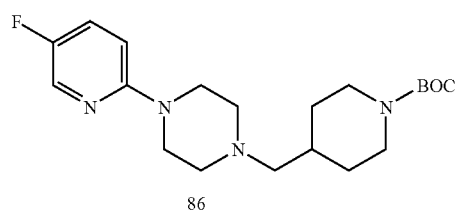

Compound 85 was prepared from compound 84 using TFA deprotection procedure described in step 2 of example 2.

Compound 85 was converted into compound 86 using the standard reductive amination procedure (NaBH(OAc)$_3$, CH$_2$Cl$_2$, room temperature) of the 4-formyl-N—BOC-piperidine, followed by the aqueous NaHCO$_3$ work-up and concentration of the organic phase. Crude 86 was purified by flash chromatography (20% ethyl acetate/hexanes).

Compound 86 was converted into the title compound 796453 using procedures described in steps 3 and 4 of example 14. MH$^+$=496

Using various procedures described above, the following compounds were prepared:

| Ex. | Structure | (M + H) |
|---|---|---|
| 113 | 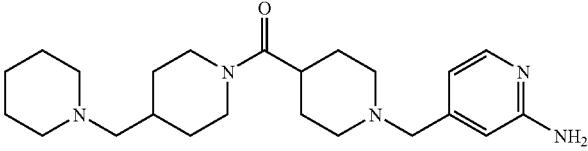 | 400 |

General Procedure for $H_3$-Receptor Binding Assay

The source of the $H_3$ receptors in this experiment was guinea pig brain. Alternatively, the source of $H_3$ receptors was recombinant human receptor, expressed in HEK-293 (human embryonic kidney) cells.

The animals weighed 400-600 g. The brain tissue was homogenized with a solution of 50 mM Tris, pH 7.5. The final concentration of tissue in the homogenization buffer was 10% w/v. The homogenates were centrifuged at 1,000×g for 10 min. in order to remove clumps of tissue and debris. The resulting supernatants were then centrifuged at 50,000×g for 20 min. in order to sediment the membranes, which were next washed three times in homogenization buffer (50,000×g for 20 min. each). The membranes were frozen and stored at −70° C. until needed.

All compounds to be tested were dissolved in DMSO and then diluted into the binding buffer (50 mM Tris, pH 7.5) such that the final concentration was 2 μg/ml with 0.1% DMSO. Membranes were then added (400 μg of protein, 5 μg in the case of recombinant human receptor) to the reaction tubes. The reaction was started by the addition of 3 nM [$^3$H]R-α-methyl histamine (8.8 Ci/mmol) or 3 nM [$^3$H]N$^α$-methyl histamine (80 Ci/mmol) and continued under incubation at 30° C. for 30 min. Bound ligand was separated from unbound ligand by filtration, and the amount of radioactive ligand bound to the membranes was quantitated by liquid scintillation spectrometry. All incubations were performed in duplicate and the standard error was always less than 10%. Compounds that inhibited more than 70% of the specific binding of radioactive ligand to the receptor were serially diluted to determine a $K_i$ (nM).

Compounds of formula I have a $K_i$ within the range of about 0.3 to about 2000 nM. Preferred compounds of formula I have a $K_i$ within the range of about 0.3 to about 100 nM. More preferred compounds of formula I have a $K_i$ within the range of about 0.3 to about 20 nM. The compound of Example 92 has a Ki of 0.35 nM in the guinea pig receptor assay, while the compound of Example 88 has a Ki of 1.1 nM in the recombinant human receptor assay.

In this specification, the term "at least one compound of formula I" means that one to three different compounds of formula I may be used in a pharmaceutical composition or method of treatment. Preferably one compound of formula I is used. Similarly, "at least one $H_1$ receptor antagonist" or "at least one other compound (or agent) fro treating obesity, metabolic syndrome or cognition deficit disorders" means that one to three different $H_1$ antagonists or other compounds may be used in a pharmaceutical composition or method of treatment. Preferably, one $H_1$ antagonist or one other compound for treating obesity, metabolic syndrome or cognition deficit disorders is used in the combinations.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *The Science and Practice of Pharmacy*, 20$^{th}$ Edition, (2000), Lippincott Williams & Wilkins, Baltimore, Md.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 150 mg, preferably from about 1 mg to about 75 mg, more preferably from about 1 mg to about 50 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 75 mg/day, in two to four divided doses.

When the invention comprises a combination of H₃ antagonist and H₁ antagonist compounds, the two active components may be co-administered simultaneously or sequentially, or a single pharmaceutical composition comprising a H₃ antagonist and an H₁ antagonist in a pharmaceutically acceptable carrier can be administered. The components of the combination can be administered individually or together in any conventional dosage form such as capsule, tablet, powder, cachet, suspension, solution, suppository, nasal spray, etc. The dosage of the H₁ antagonist can be determined from published material, and may range from 1 to 1000 mg per dose. When used in combination, the dosage levels of the individual components are preferably lower than the recommended individual dosages because of the advantageous effect of the combination.

When separate H₃ and H₁ antagonist pharmaceutical compositions are to be administered, they can be provided in a kit comprising in a single package, one container comprising an H₃ antagonist in a pharmaceutically acceptable carrier, and a separate container comprising an H₁ antagonist in a pharmaceutically acceptable carrier, with the H₃ and H₁ antagonists being present in amounts such that the combination is therapeutically effective. A kit is advantageous for administering a combination when, for example, the components must be administered at different time intervals or when they are in different dosage forms.

Similarly, when the invention comprises a combination of H₃ antagonist and at least one other compound for treating obesity, metabolic syndrome cognition deficit disorders, NAFLD, hepatic steatosis, NASH, cirrhosis, or hepatacellular carcinoma, the two active components may be co-administered simultaneously or sequentially, or a single pharmaceutical composition comprising a H₃ antagonist and another compound in a pharmaceutically acceptable carrier can be administered. The components of the combination can be administered individually or together in any conventional dosage form such as capsule, tablet, powder, cachet, suspension, solution, suppository, nasal spray, etc. The dosage of the other compound for treating obesity, metabolic syndrome or cognition deficit disorders can be determined from published material, and may range from 1 to 1000 mg per dose.

When separate pharmaceutical compositions comprising an H₃ antagonist and one other compound for treating obesity, metabolic syndrome or cognition deficit disorders are to be administered, they can be provided in a kit comprising in a single package, one container comprising an H₃ antagonist in a pharmaceutically acceptable carrier, and a separate container or containers comprising a compound for treating obesity, metabolic syndrome, cognition deficit disorders, NAFLD, hepatic steatosis, NASH, cirrhosis, or hepatacellular carcinoma in a pharmaceutically acceptable carrier, with the H₃ antagonists and other compounds being present in amounts such that the combination is therapeutically effective. A kit is advantageous for administering a combination when, for example, the components must be administered at different time intervals or when they are in different dosage forms.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound represented by the structural formula

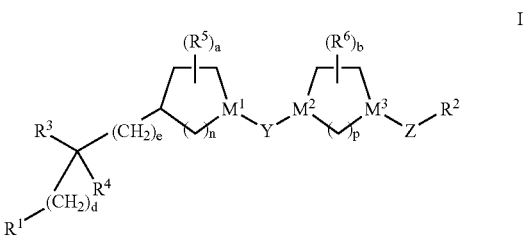

or a pharmaceutically acceptable salt thereof, wherein:
a is 0;
b is 0;
d is 0;
e is 0;
n is 2;
p is 2;
$M^1$ is N;
$M^2$ is CH or CF;
$M^3$ is N;
Y is —C(═O)—;
Z is CH2;
$R^1$ is H, alkyl, alkenyl, $R^{10}$-cycloalkyl, $R^{10}$-aryl, $R^{10}$-monoheteroaryl or $R^{10}$-heterocycloalkyl,
wherein said monocyclic heteroaryl ring has from 1 to 6 carbon atoms and 1 to 4 heteroatoms, each heteroatom independently selected from O, S and N;
R2 is a six-membered heteroaryl
$R^3$ and $R^4$ are independently selected from the group consisting of H, halo, alkyl, haloalkyl, hydroxyalkyl, alkoxyalkyl, hydroxyalkoxy, alkoxyalkoxy, aryl, arylalkyl, cycloalkyl, heterocycloalkyl, heteroaryl, heteroarylalkyl, —$OR^{12}$, —CN, —$(CH_2)_f$—$N(R^{12})_2$, —$(CH_2)_f$—$N(R^{19})$—$SO_2R^{12}$, —$(CH_2)_f$—$N(R^{19})$—C(O)$R^{12}$, —$(CH_2)_f$—NHC(O)NHR$^{12}$, —$(CH_2)_f$—NHC(O)OR$^{12}$, —O—C(O)NHR$^{12}$, —$(CH_2)_f$—C(O)OR$^{12}$ and —O—$(CH_2)_f$—C(O)OR$^{12}$, provided that when one of $R^3$ and $R^4$ is a heteroatom-linked substituent, the other is H, wherein f is 0, 1 or 2; or $R^3$ and $R^4$, together with the carbon to which they are attached, form —C(═C($R^{15}$)($R^{18}$))—, a 3- to 7-membered cycloalkyl ring substituted by $R^{13}$, a 3- to 7-membered heterocycloalkyl ring substituted by $R^{13}$, a $R^{13}$-phenyl ring, or a 5 to 6-membered heteroaryl ring substituted by $R^{13}$;
each $R^9$ is independently selected from the group consisting of H and alkyl;
$R^{10}$ is 1 to 4 substituents independently selected from the group consisting of H, halo, alkyl, —OH, alkoxy, $R^{10'}$-cycloalkyl, $R^{10'}$-aryl, $R^{10'}$-heteroaryl, $R^{10'}$-aryloxy, haloalkyl, haloalkoxy —$NO_2$, —$CO_2R^{11}$, —$N(R^{11})_2$, —$CON(R^{11})_2$, —NHC(O)$R^{11}$, —NHC(O)OR$^{11}$, —NHSO$_2R^{11}$, —$SO_2N(R^{11})_2$ and —CN;
each $R^{10'}$is 1 to 4 substituents independently selected from the group consisting of H, halo, alkyl, —OH, alkoxy, aryl, heteroaryl, aryloxy, haloalkyl, haloalkoxy, —$NO_2$, —$CO_2R^{11}$, —$N(R^{11})_2$, —$CON(R^{11})_2$, —NHC(O)$R^{11}$, —NHC(O)OR$^{11}$, —NHSO$_2R^{11}$, —$SO_2N(R^{11})_2$ and —CN;
each $R^{11}$ is independently selected from the group consisting of H, alkyl, haloalkyl, $R^{18}$-aryl, $R^{18}$-heteroaryl, $R^{18}$-arylalkyl, $R^{18}$-cycloalkyl and $R^{18}$-heterocycloalkyl;
each $R^{12}$ is independently selected from the group consisting of H, alkyl, alkenyl, haloalkyl, $R^{18}$-aryl, $R^{18}$-arylalkyl, $R^{18}$-heteroaryl, $R^{18}$-heteroarylalkyl, $R^{18}$-cycloalkyl, $R^{18}$-cycloalkylalkyl and $R^{18}$-heterocycloalkyl;

$R^{13}$ is 1 to 4 substituents independently selected form the group consisting of H, halo, alkyl, —OH, alkoxy, hydroxyalkyl, alkoxyalkyl, —CO$_2$R$^{14}$, —C(O)N(R$^{14}$)$_2$, haloalkyl, —CF$_3$, and —CN; or two $R^{13}$ substituents on the same carbon atom form =O;

each $R^{14}$ is independently selected from the group consisting of H and alkyl;

$R^{15}$ is H, alkyl, halo, aryl or haloalkyl;

$R^{16}$ is 1 to 3 substituents independently selected from the group consisting of H, halo, alkyl, —OH, alkoxy, $R^{10}$-aryl, $R^{10}$-aryloxy, haloalkyl, —CF$_3$, haloalkoxy, —NO$_2$, —CO$_2$R$^{17}$, —N(R$^{17}$)$_2$, —CON(R$^{17}$)$_2$, —NHC(O)R$^{17}$, —NHC(O)OR$^{17}$, —NHSO$_2$R$^{17}$, —SO$_2$N(R$^{17}$)$_2$ and —CN;

each $R^{17}$ is independently selected from the group consisting of H, alkyl, haloalkyl, $R^{10}$-aryl, $R^{10}$-heteroaryl, $R^{10}$-cycloalkyl and $R^{10}$-heterocycloalkyl;

$R^{18}$ is H, alkyl, halo, aryl, haloalkyl, alkoxy, heteroaryl, —O—C(O)R$^{12}$, —C(O)N(R$^{12}$)$_2$, —C(O)OR$^{12}$, —NO$_2$, —CN or —C(O)-heterocycloalkyl;

$R^{19}$ is H, alkyl or $R^{10}$-heterocycloalkylalkyl.

2. A compound of claim 1 wherein $R^1$ is $R^{10}$-pbenyl or $R^{10}$-pyridyl.

3. A compound of claim 2 wherein $R^1$ is $R^{10}$-phenyl or $R^{10}$-pyridyl and $R^{10}$ is 1 or 2 substituents independently selected from H, alkyl, halo, —CF$_3$, —CHF$_2$ and —CN.

4. A compound of claim 1 wherein $R^2$ is $R^{16}$-pyridyl, $R^{16}$-pyrimidinyl, $R^{16}$-pyridazinyl, $R^{16}$-thiazolyl, $R^{16}$-azetidinyl or $R^{16}$-tetrahydropyranyl, and R16 is 1 or 2 substituents independently selected from H, —CH$_3$, —NH$_2$ and —NHCH$_3$.

5. A compound of claim 1 wherein $R^3$ is hydrogen and $R^4$ is hydrogen, halo, —OH, alkoxyalkyl or —(CH$_2$)$_f$N(R$^{19}$)SO$_2$R$^{12}$, wherein $R^{19}$ is H and f is 0.

6. A compound of claim 5 wherein $R^3$ is H and $R^4$ is alkoxyalkyl.

7. A compound of claim 1 wherein $R^3$ and $R^4$ are joined together with the carbon to which they are attached to form —C(=C(R$^{15}$)(R$^{18}$))—, wherein $R^{15}$ and $R^{18}$ are each H, or wherein $R^{15}$ is H and $R^{18}$ is halo or alkoxy.

8. A compound of claim 1 wherein $R^3$, $R^4$ and the carbon to which they are attached form an $R^{13}$-suhstituted cycloalkyl ring.

9. A compound having the structure:

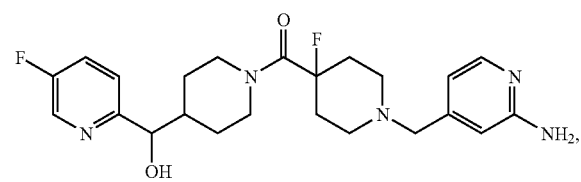

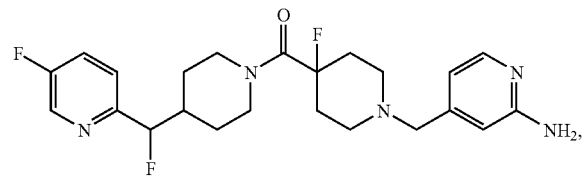

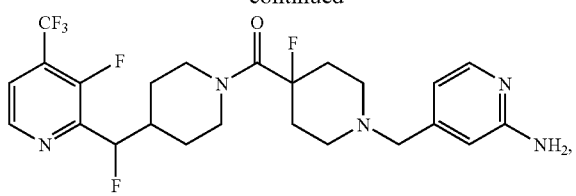

-continued

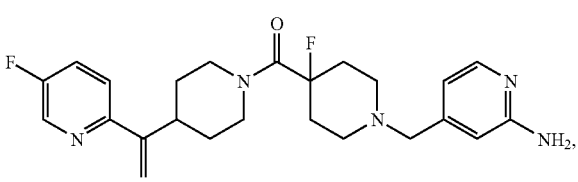

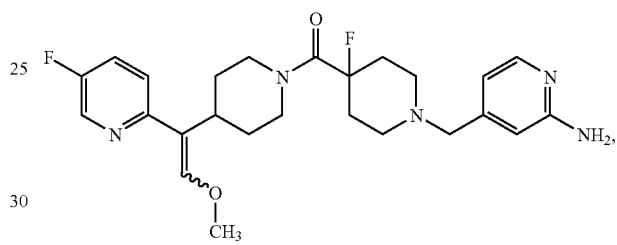

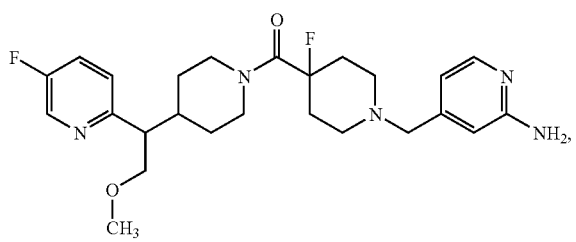

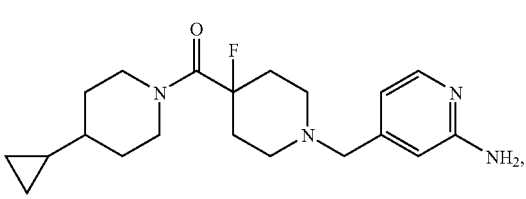

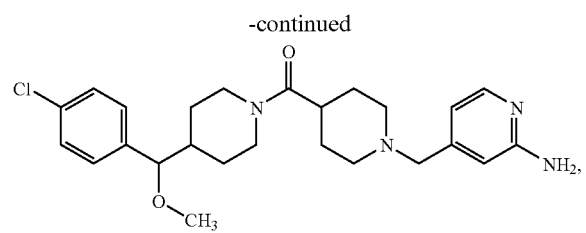
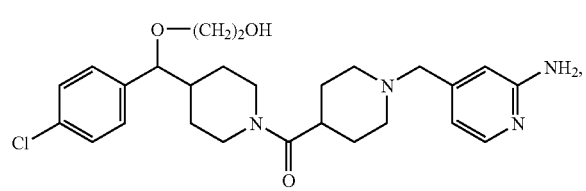
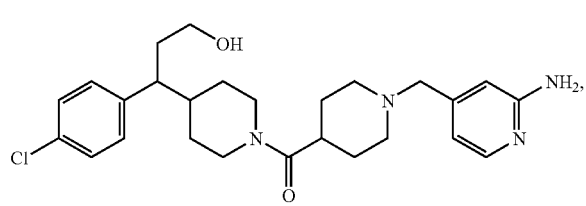
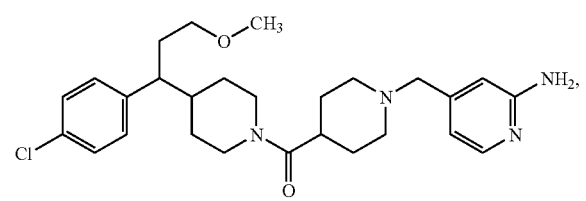
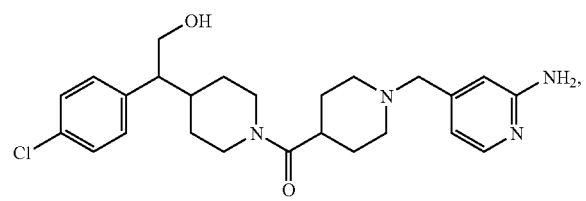
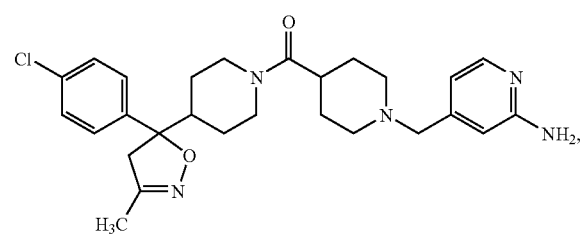
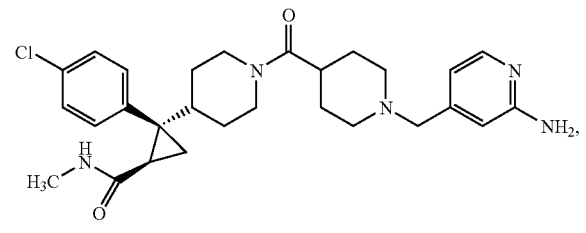
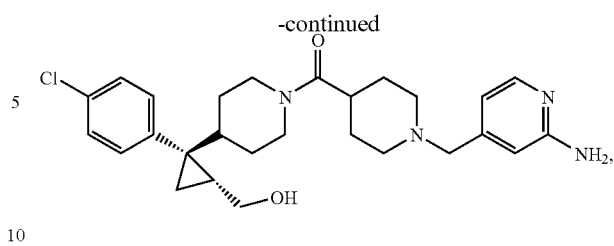
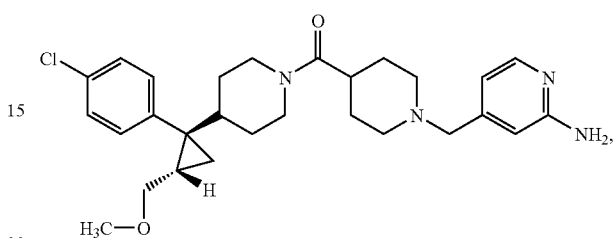
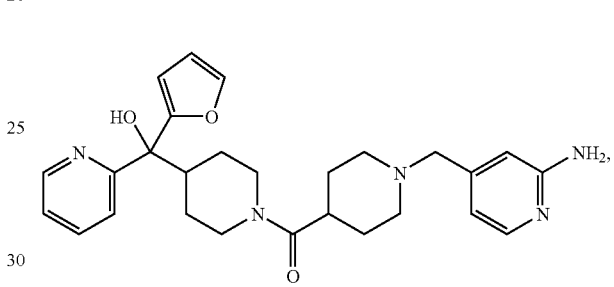
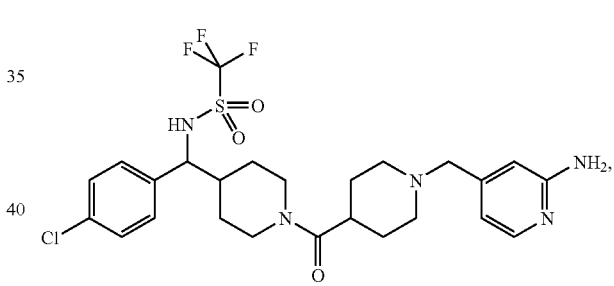
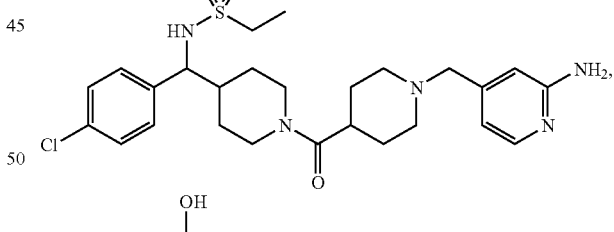
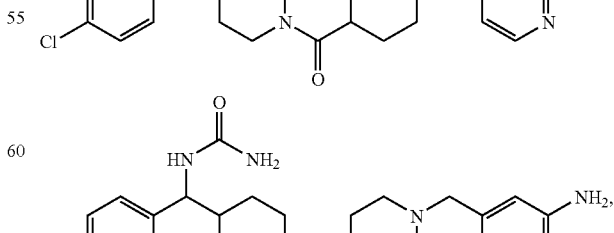
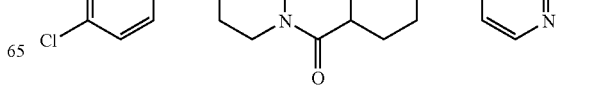

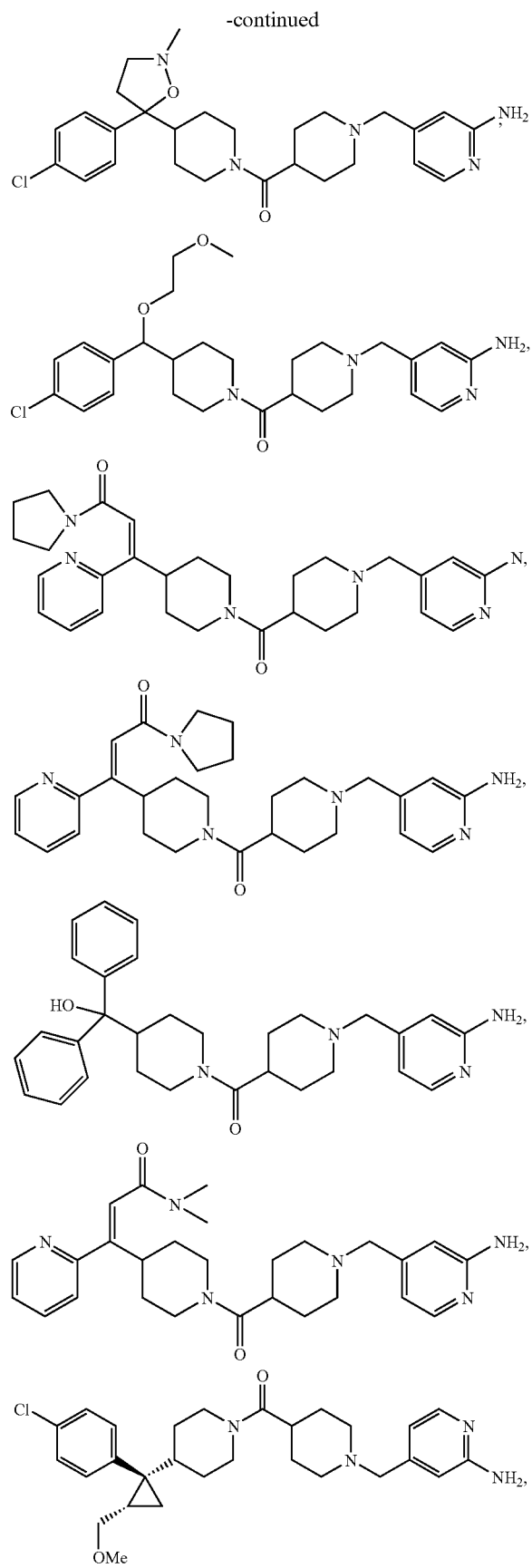
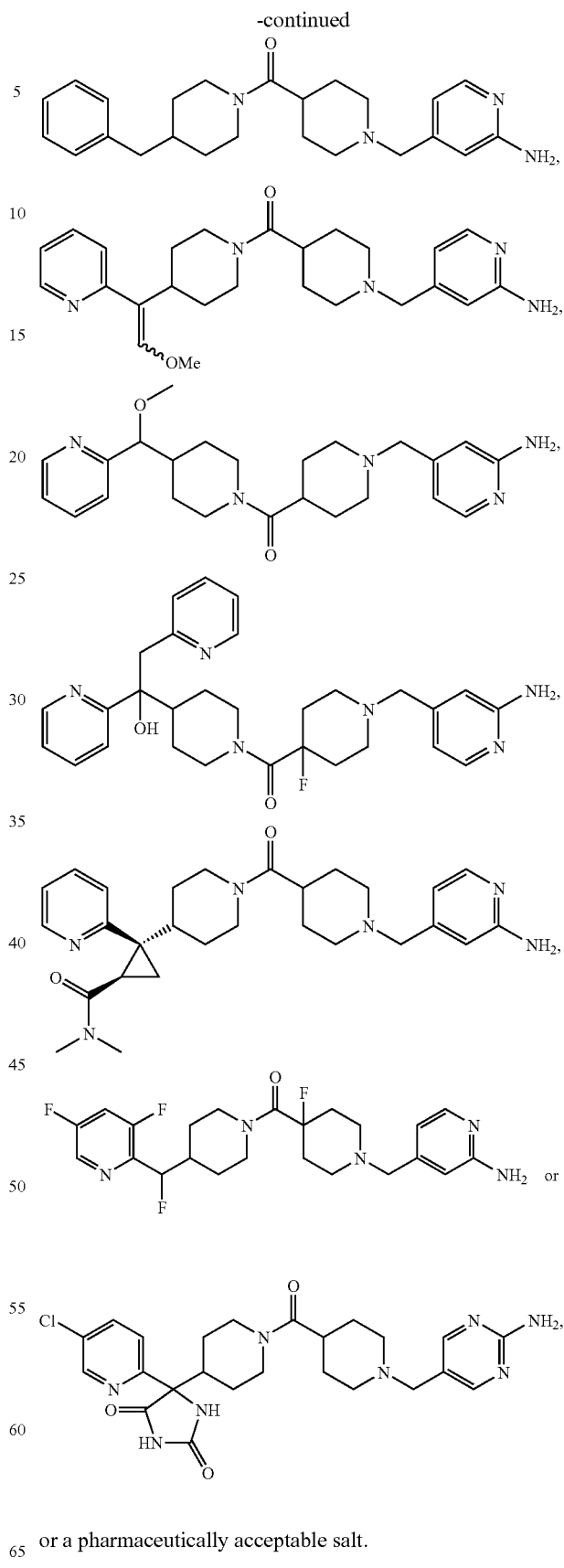
or a pharmaceutically acceptable salt.
* * * * *

UNITED STATES PATENT AND TRADEMARK OFFICE
CERTIFICATE OF CORRECTION

PATENT NO. : 7,408,066 B2
APPLICATION NO. : 11/455873
DATED : August 5, 2008
INVENTOR(S) : Robert G. Aslanian et al.

It is certified that error appears in the above-identified patent and that said Letters Patent is hereby corrected as shown below:

On the title page item (73) Assignee, Schering Corproation should read --Schering Corporation--.

On the title page item (56) References Cited, Foreign Patent Document WO 02/32693 A2 should read --WO 02/32893 A2--.

Claim 8, column 83, line 43: Replace "-suhstituted" with --substituted--.

Claim 9, column 88, line 65: Insert --thereof-- after salt.

Signed and Sealed this

Fifth Day of January, 2010

David J. Kappos
*Director of the United States Patent and Trademark Office*